(12) United States Patent
Weber et al.

(10) Patent No.: US 8,052,743 B2
(45) Date of Patent: Nov. 8, 2011

(54) ENDOPROSTHESIS WITH THREE-DIMENSIONAL DISINTEGRATION CONTROL

(75) Inventors: Jan Weber, Maastricht (NL); Liliana Atanasoska, Edina, MN (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 622 days.

(21) Appl. No.: 11/833,211

(22) Filed: Aug. 2, 2007

(65) Prior Publication Data

US 2008/0131479 A1 Jun. 5, 2008

Related U.S. Application Data

(60) Provisional application No. 60/821,260, filed on Aug. 2, 2006.

(51) Int. Cl.
*A61F 2/06* (2006.01)
(52) U.S. Cl. .................................. 623/1.38; 424/426
(58) Field of Classification Search .................. None
See application file for complete search history.

(56) References Cited

U.S. PATENT DOCUMENTS

| | | |
|---|---|---|
| 2,950,187 A | 8/1960 | Ototani |
| 3,560,362 A | 2/1971 | Kasamatsu et al. |
| 3,569,660 A | 3/1971 | Houldcroft |
| 3,687,135 A | 8/1972 | Stroganov et al. |
| 3,758,396 A | 9/1973 | Vieth et al. |
| 3,868,578 A | 2/1975 | Oldham |
| 3,910,819 A | 10/1975 | Rembaum et al. |
| 3,948,254 A | 4/1976 | Zaffaroni |
| 3,952,334 A | 4/1976 | Bokros et al. |
| 3,993,072 A | 11/1976 | Zaffaroni |
| 4,002,877 A | 1/1977 | Banas |
| 4,101,984 A | 7/1978 | MacGregor |
| 4,143,661 A | 3/1979 | LaForge et al. |
| 4,202,055 A | 5/1980 | Reiner et al. |
| 4,237,559 A | 12/1980 | Borom |
| 4,308,868 A | 1/1982 | Jhabvala |
| 4,334,327 A | 6/1982 | Lyman et al. |
| 4,401,546 A | 8/1983 | Nakamura et al. |
| 4,532,929 A | 8/1985 | Mattei et al. |
| 4,539,061 A | 9/1985 | Sagiv |
| 4,542,539 A | 9/1985 | Rowe et al. |
| 4,585,652 A | 4/1986 | Miller et al. |
| 4,634,502 A | 1/1987 | Callahan et al. |
| 4,655,771 A | 4/1987 | Wallsten |
| 4,657,544 A | 4/1987 | Pinchuk |
| 4,665,896 A | 5/1987 | LaForge et al. |
| 4,705,502 A | 11/1987 | Patel |
| 4,713,070 A | 12/1987 | Mano |
| 4,725,273 A | 2/1988 | Kira |
| 4,733,665 A | 3/1988 | Palmaz |
| 4,767,418 A | 8/1988 | Deininger et al. |
| 4,784,659 A | 11/1988 | Fleckenstein et al. |
| 4,800,882 A | 1/1989 | Gianturco |
| 4,804,382 A | 2/1989 | Turina et al. |
| 4,886,062 A | 12/1989 | Wiktor |
| 4,954,126 A | 9/1990 | Wallsten |
| 4,976,692 A | 12/1990 | Atad |
| 4,994,071 A | 2/1991 | MacGregor |
| 5,024,671 A | 6/1991 | Tu et al. |
| 5,059,211 A | 10/1991 | Stack et al. |
| 5,061,275 A | 10/1991 | Wallsten et al. |
| 5,061,914 A | 10/1991 | Busch et al. |
| 5,073,365 A | 12/1991 | Katz et al. |
| 5,079,203 A | 1/1992 | Pinnavaia |
| 5,091,024 A | 2/1992 | DeBold et al. |
| 5,091,205 A | 2/1992 | Fan |
| 5,102,403 A | 4/1992 | Alt |
| 5,120,322 A | 6/1992 | Davis et al. |
| 5,125,971 A | 6/1992 | Nonami et al. |
| 5,147,370 A | 9/1992 | McNamara et al. |
| 5,163,958 A | 11/1992 | Pinchuk |
| 5,195,969 A | 3/1993 | Wang et al. |
| 5,205,921 A | 4/1993 | Shirkanzadeh |
| 5,234,457 A | 8/1993 | Andersen |
| 5,236,413 A | 8/1993 | Feiring |
| 5,236,447 A | 8/1993 | Kubo et al. |
| 5,270,086 A | 12/1993 | Hamlin |
| 5,279,292 A | 1/1994 | Baumann et al. |
| 5,290,585 A | 3/1994 | Elton |
| 5,292,558 A | 3/1994 | Heller et al. |
| 5,302,414 A | 4/1994 | Alkhimov et al. |
| 5,304,121 A | 4/1994 | Sahatjian |
| 5,304,195 A | 4/1994 | Twyford, Jr. et al. |

(Continued)

FOREIGN PATENT DOCUMENTS

AU 739 507 11/1998

(Continued)

OTHER PUBLICATIONS

Soto et al, "Amporphous Magnesium Nitride Films Produced by Reactive Pulsed Laser Deposition", Journal of Non-crystalline solids, 342 (2004), p. 65-69.*
U.S. Appl. No. 10/849,742, filed May 20, 2004, Chen et al.
U.S. Appl. No. 60/8269,002, filed Sep. 18, 2006, Girton et al.
U.S. Appl. No. 60/862,318, filed Oct. 20, 2006, Atanasoska et al.
U.S. Appl. No. 60/845,136, filed Sep. 15, 2006, Weber et al.
"Galvanic cell" printout from wikipedia, 2 pgs, printed Oct. 28, 2005.
"Galvanic corrosion", http://www.corrosion-doctors.org/Aircraft/galvdefi.htm, 3 pgs., printed Oct. 28, 2005.
"Galvanic series" printout from Wikipedia, p. 1 of 2, printed Oct. 28, 2005.
"Best of the ACC Scientific Session 2002," *Rev. Cardiovasc. Med.*, 2002, 3(2):85-104.
"Corrosion Theory and Corrosion Protection," *EM 1110-2-3400*, 1995, 8 pages.
Aghion et al., "Newly Developed Magnesium Alloys for Powertrain Applications," *JOM*, 2003, p. 30.
Andión et al., "Corrosion behaviour at the interface of steel bars embedded in cement slurries. Effect of phenol polymer coatings," *Corrosion Science*, 2002, 44:2805-2816.

(Continued)

*Primary Examiner* — Robert A Wax
*Assistant Examiner* — Bethany Barham
(74) *Attorney, Agent, or Firm* — Fish & Richardson P.C.

(57) ABSTRACT

The present invention comprises a medical device having a support structure made from alternating layers. One or more layers may be made by direct metal laser sintering. One or more layers may be made by introducing nitrogen into a previously formed layer via excimer laser nitriding.

18 Claims, 14 Drawing Sheets

U.S. PATENT DOCUMENTS

| | | | |
|---|---|---|---|
| 5,306,286 A | 4/1994 | Stack et al. |
| 5,314,453 A | 5/1994 | Jeutter |
| 5,322,520 A | 6/1994 | Milder |
| 5,342,348 A | 8/1994 | Kaplan |
| 5,348,553 A | 9/1994 | Whitney |
| 5,356,433 A | 10/1994 | Rowland et al. |
| 5,360,440 A | 11/1994 | Andersen |
| 5,366,504 A | 11/1994 | Andersen et al. |
| 5,380,298 A | 1/1995 | Zabetakis et al. |
| 5,383,935 A | 1/1995 | Shirkhanzadeh |
| 5,385,776 A | 1/1995 | Maxfield et al. |
| 5,397,307 A | 3/1995 | Goodin |
| 5,405,367 A | 4/1995 | Schulman et al. |
| 5,421,955 A | 6/1995 | Lau et al. |
| 5,439,446 A | 8/1995 | Barry |
| 5,443,458 A | 8/1995 | Eury |
| 5,443,496 A | 8/1995 | Schwartz et al. |
| 5,443,500 A | 8/1995 | Sigwart |
| 5,449,373 A | 9/1995 | Pinchasik et al. |
| 5,449,382 A | 9/1995 | Dayton |
| 5,458,627 A | 10/1995 | Baranowski, Jr. et al. |
| 5,462,575 A | 10/1995 | Del Corso |
| 5,464,450 A | 11/1995 | Buscemi et al. |
| 5,464,650 A | 11/1995 | Berg et al. |
| 5,468,574 A | 11/1995 | Ehrenberg et al. |
| 5,474,797 A | 12/1995 | Sioshansi et al. |
| 5,500,013 A | 3/1996 | Buscemi et al. |
| 5,514,154 A | 5/1996 | Lau et al. |
| 5,527,337 A | 6/1996 | Stack et al. |
| 5,536,573 A | 7/1996 | Rubner et al. |
| 5,545,208 A | 8/1996 | Wolff et al. |
| 5,549,664 A | 8/1996 | Hirata et al. |
| 5,551,954 A | 9/1996 | Buscemi et al. |
| 5,578,075 A | 11/1996 | Dayton |
| 5,587,200 A * | 12/1996 | Lorenz et al. ............... 427/2.24 |
| 5,587,507 A | 12/1996 | Kohn et al. |
| 5,591,222 A | 1/1997 | Susawa et al. |
| 5,591,224 A | 1/1997 | Schwartz et al. |
| 5,599,352 A | 2/1997 | Dinh et al. |
| 5,603,556 A | 2/1997 | Klink |
| 5,605,696 A | 2/1997 | Eury et al. |
| 5,607,463 A | 3/1997 | Schwartz et al. |
| 5,609,629 A | 3/1997 | Fearnot et al. |
| 5,614,549 A | 3/1997 | Greenwald et al. |
| 5,624,411 A | 4/1997 | Tuch |
| 5,628,787 A | 5/1997 | Mayer |
| 5,629,077 A | 5/1997 | Turnland et al. |
| 5,632,771 A | 5/1997 | Boatman et al. |
| 5,632,840 A | 5/1997 | Campbell |
| 5,649,951 A | 7/1997 | Davidson |
| 5,658,327 A | 8/1997 | Altman et al. |
| 5,672,242 A | 9/1997 | Jen |
| 5,674,192 A | 10/1997 | Sahatjian et al. |
| 5,674,242 A | 10/1997 | Phan |
| 5,676,685 A | 10/1997 | Razavi |
| 5,679,440 A | 10/1997 | Kubota |
| 5,690,670 A | 11/1997 | Davidson |
| 5,693,085 A | 12/1997 | Buirge et al. |
| 5,693,928 A | 12/1997 | Egitto et al. |
| 5,697,967 A | 12/1997 | Dinh et al. |
| 5,700,286 A | 12/1997 | Tartaglia et al. |
| 5,716,981 A | 2/1998 | Hunter et al. |
| 5,721,049 A | 2/1998 | Marcolongo et al. |
| 5,725,570 A | 3/1998 | Heath |
| 5,733,925 A | 3/1998 | Kunz et al. |
| 5,741,331 A | 4/1998 | Pinchuk |
| 5,744,515 A | 4/1998 | Clapper |
| 5,749,809 A | 5/1998 | Lin |
| 5,749,880 A | 5/1998 | Banas et al. |
| 5,758,562 A | 6/1998 | Thompson |
| 5,759,192 A | 6/1998 | Saunders |
| 5,761,775 A | 6/1998 | Legome et al. |
| 5,769,883 A | 6/1998 | Buscemi et al. |
| 5,769,884 A | 6/1998 | Solovay |
| 5,773,925 A | 6/1998 | Kimura et al. |
| 5,776,184 A | 7/1998 | Tuch |
| 5,779,904 A | 7/1998 | Ruderman et al. |
| 5,780,807 A | 7/1998 | Saunders |
| 5,788,626 A | 8/1998 | Thompson |
| 5,788,687 A | 8/1998 | Batich et al. |
| 5,788,979 A | 8/1998 | Alt et al. |
| 5,797,898 A | 8/1998 | Santini, Jr. et al. |
| 5,800,511 A | 9/1998 | Mayer |
| 5,815,904 A | 10/1998 | Clubb et al. |
| 5,817,046 A | 10/1998 | Glickman |
| 5,824,045 A | 10/1998 | Alt |
| 5,824,048 A | 10/1998 | Tuch |
| 5,824,077 A | 10/1998 | Mayer |
| 5,830,217 A | 11/1998 | Ryan |
| 5,833,715 A | 11/1998 | Vachon et al. |
| 5,837,007 A | 11/1998 | Altman et al. |
| 5,837,275 A | 11/1998 | Burrell et al. |
| 5,840,387 A | 11/1998 | Berlowitz-Tarrant et al. |
| 5,843,089 A | 12/1998 | Sahatjian et al. |
| 5,843,172 A | 12/1998 | Yan |
| 5,852,277 A | 12/1998 | Gustafson |
| 5,854,382 A | 12/1998 | Loomis |
| 5,858,556 A | 1/1999 | Eckert et al. |
| 5,869,140 A | 2/1999 | Blohowiak et al. |
| 5,873,904 A | 2/1999 | Ragheb et al. |
| 5,876,756 A | 3/1999 | Takada et al. |
| 5,879,697 A | 3/1999 | Ding et al. |
| 5,880,661 A | 3/1999 | Davidson et al. |
| 5,882,335 A | 3/1999 | Leone et al. |
| 5,891,108 A | 4/1999 | Leone et al. |
| 5,891,191 A | 4/1999 | Stinson |
| 5,899,935 A | 5/1999 | Ding |
| 5,902,266 A | 5/1999 | Leone et al. |
| 5,906,759 A | 5/1999 | Richter |
| 5,907,893 A | 6/1999 | Zadno-Azizi et al. |
| 5,922,005 A | 7/1999 | Richter et al. |
| 5,922,021 A | 7/1999 | Jang |
| 5,928,247 A | 7/1999 | Barry et al. |
| 5,935,506 A | 8/1999 | Schmitz et al. |
| 5,938,903 A | 8/1999 | Broderick |
| 5,941,843 A | 8/1999 | Atanasoska et al. |
| 5,951,458 A | 9/1999 | Hastings et al. |
| 5,951,881 A | 9/1999 | Rogers et al. |
| 5,954,706 A | 9/1999 | Sahatjian |
| 5,957,975 A | 9/1999 | Lafont et al. |
| 5,958,440 A | 9/1999 | Burrell et al. |
| 5,961,547 A | 10/1999 | Razavi |
| 5,968,091 A | 10/1999 | Pinchuk et al. |
| 5,968,092 A | 10/1999 | Buscemi et al. |
| 5,972,027 A | 10/1999 | Johnson |
| 5,972,192 A | 10/1999 | Dubin et al. |
| 5,976,169 A | 11/1999 | Imran |
| 5,976,454 A | 11/1999 | Sterzel et al. |
| 5,977,204 A | 11/1999 | Boyan et al. |
| 5,980,554 A | 11/1999 | Lenker et al. |
| 5,980,564 A | 11/1999 | Stinson |
| 5,980,566 A | 11/1999 | Alt et al. |
| 6,001,125 A | 12/1999 | Golds et al. |
| 6,013,591 A | 1/2000 | Ying et al. |
| 6,017,553 A | 1/2000 | Burrell et al. |
| 6,017,577 A | 1/2000 | Hostettler et al. |
| 6,021,347 A | 2/2000 | Herbst et al. |
| 6,025,036 A | 2/2000 | McGill et al. |
| 6,027,742 A | 2/2000 | Lee et al. |
| 6,034,295 A | 3/2000 | Rehberg et al. |
| 6,056,776 A | 5/2000 | Lau et al. |
| 6,063,101 A | 5/2000 | Jacobsen et al. |
| 7,713,297 B2 | 5/2000 | Alt |
| 6,071,305 A | 6/2000 | Brown et al. |
| 6,080,190 A | 6/2000 | Schwartz |
| 6,086,773 A | 7/2000 | Dufresne et al. |
| 6,096,070 A | 8/2000 | Ragheb et al. |
| 6,096,175 A | 8/2000 | Roth |
| 6,099,561 A | 8/2000 | Alt |
| 6,099,562 A | 8/2000 | Ding et al. |
| 6,106,473 A | 8/2000 | Violante et al. |
| 6,107,004 A | 8/2000 | Donadio, III |
| 6,117,592 A | 9/2000 | Hoshino et al. |
| 6,120,260 A | 9/2000 | Jirele |
| 6,120,535 A | 9/2000 | McDonald et al. |
| 6,120,660 A | 9/2000 | Chu et al. |
| 6,123,861 A | 9/2000 | Santini, Jr. et al. |

| Patent | Date | Inventor |
|---|---|---|
| 6,132,463 A | 10/2000 | Lee et al. |
| 6,139,573 A | 10/2000 | Sogard et al. |
| 6,139,574 A | 10/2000 | Vacanti et al. |
| 6,139,913 A | 10/2000 | Van Steenkiste et al. |
| 6,140,740 A | 10/2000 | Porat et al. |
| 6,143,370 A | 11/2000 | Panagiotou et al. |
| 6,153,252 A | 11/2000 | Hossainy et al. |
| 6,159,142 A | 12/2000 | Alt |
| 6,162,238 A | 12/2000 | Kaplan et al. |
| 6,164,284 A | 12/2000 | Schulman et al. |
| 6,165,211 A | 12/2000 | Thompson |
| 6,167,307 A | 12/2000 | Hess |
| 6,168,602 B1 | 1/2001 | Ryan |
| 6,170,488 B1 | 1/2001 | Spillman, Jr. et al. |
| 6,174,329 B1 | 1/2001 | Callol et al. |
| 6,174,330 B1 | 1/2001 | Stinson |
| 6,180,222 B1 | 1/2001 | Schulz et al. |
| 6,185,455 B1 | 2/2001 | Loeb et al. |
| 6,185,457 B1 | 2/2001 | Kroll et al. |
| 6,190,404 B1 | 2/2001 | Palmaz et al. |
| 6,192,271 B1 | 2/2001 | Hayman |
| 6,201,991 B1 | 3/2001 | Chekanov |
| 6,203,536 B1 | 3/2001 | Berg et al. |
| 6,206,914 B1 | 3/2001 | Soykan et al. |
| 6,206,915 B1 | 3/2001 | Fagan et al. |
| 6,206,916 B1 | 3/2001 | Furst |
| 6,212,434 B1 | 4/2001 | Scheiner |
| 6,214,037 B1 | 4/2001 | Mitchell et al. |
| 6,214,042 B1 | 4/2001 | Jacobsen et al. |
| 6,217,607 B1 | 4/2001 | Alt |
| 6,231,597 B1 | 5/2001 | Deem et al. |
| 6,240,616 B1 | 6/2001 | Yan |
| 6,241,762 B1 | 6/2001 | Shanley |
| 6,245,103 B1 | 6/2001 | Stinson |
| 6,245,104 B1 | 6/2001 | Alt |
| 6,249,952 B1 | 6/2001 | Ding |
| 6,251,136 B1 | 6/2001 | Guruwaiya et al. |
| 6,251,980 B1 | 6/2001 | Lan et al. |
| 6,253,252 B1 | 6/2001 | Schofield |
| 6,253,443 B1 | 7/2001 | Johnson |
| 6,254,632 B1 | 7/2001 | Wu et al. |
| 6,258,117 B1 | 7/2001 | Camrud et al. |
| 6,264,687 B1 | 7/2001 | Tomonto |
| 6,270,831 B2 | 8/2001 | Kumar et al. |
| 6,273,908 B1 | 8/2001 | Ndondo-Lay |
| 6,273,913 B1 | 8/2001 | Wright et al. |
| 6,277,078 B1 | 8/2001 | Porat et al. |
| 6,280,385 B1 | 8/2001 | Melzer et al. |
| 6,280,411 B1 | 8/2001 | Lennox |
| 6,283,386 B1 | 9/2001 | Van Steenkiste et al. |
| 6,287,331 B1 | 9/2001 | Heath |
| 6,287,332 B1 | 9/2001 | Bolz |
| 6,287,335 B1 | 9/2001 | Drasler et al. |
| 6,287,628 B1 | 9/2001 | Hossainy et al. |
| 6,290,721 B1 | 9/2001 | Heath |
| 6,290,722 B1 | 9/2001 | Wang |
| 6,291,076 B1 | 9/2001 | Nakatsugawa |
| 6,299,604 B1 | 10/2001 | Ragheb et al. |
| 6,299,755 B1 | 10/2001 | Richter |
| 6,306,144 B1 | 10/2001 | Sydney et al. |
| 6,309,414 B1 | 10/2001 | Rolando et al. |
| 6,312,463 B1 | 11/2001 | Rourke et al. |
| 6,315,708 B1 | 11/2001 | Salmon et al. |
| 6,323,146 B1 | 11/2001 | Pugh et al. |
| 6,325,825 B1 | 12/2001 | Kula et al. |
| 6,327,504 B1 | 12/2001 | Dolgin et al. |
| 6,331,312 B1 | 12/2001 | Lee et al. |
| 6,335,029 B1 | 1/2002 | Kamath et al. |
| 6,337,076 B1 | 1/2002 | Studin |
| 6,338,739 B1 | 1/2002 | Datta et al. |
| 6,342,507 B1 | 1/2002 | Naicker et al. |
| 6,344,055 B1 | 2/2002 | Shukov |
| 6,348,960 B1 | 2/2002 | Etori et al. |
| 6,358,276 B1 | 3/2002 | Edwin |
| 6,364,823 B1 | 4/2002 | Garibaldi et al. |
| 6,364,856 B1 | 4/2002 | Ding et al. |
| 6,364,903 B2 | 4/2002 | Tseng et al. |
| 6,366,808 B1 | 4/2002 | Schroeppel et al. |
| 6,368,658 B1 | 4/2002 | Schwarz et al. |
| 6,369,355 B1 | 4/2002 | Saunders |
| 6,375,826 B1 | 4/2002 | Wang et al. |
| 6,379,379 B1 | 4/2002 | Wang |
| 6,379,382 B1 | 4/2002 | Yang |
| 6,379,383 B1 | 4/2002 | Palmaz et al. |
| 6,379,392 B1 | 4/2002 | Walak |
| 6,383,214 B1 | 5/2002 | Banas et al. |
| 6,387,121 B1 | 5/2002 | Alt |
| 6,387,124 B1 | 5/2002 | Buscemi et al. |
| 6,390,967 B1 | 5/2002 | Forman et al. |
| 6,391,033 B2 | 5/2002 | Ryan |
| 6,391,052 B2 | 5/2002 | Buirge et al. |
| 6,395,326 B1 | 5/2002 | Castro et al. |
| 6,398,806 B1 | 6/2002 | You |
| 6,409,754 B1 | 6/2002 | Smith et al. |
| 6,419,692 B1 | 7/2002 | Yang et al. |
| 6,423,092 B2 | 7/2002 | Datta et al. |
| 6,425,855 B2 | 7/2002 | Tomonto |
| 6,436,133 B1 | 8/2002 | Furst et al. |
| 6,440,166 B1 | 8/2002 | Kolluri |
| 6,440,487 B1 | 8/2002 | Delfino et al. |
| 6,440,503 B1 | 8/2002 | Merdan et al. |
| 6,447,540 B1 | 9/2002 | Fontaine et al. |
| 6,458,153 B1 | 10/2002 | Bailey et al. |
| 6,468,304 B1 | 10/2002 | Dubois-Rande et al. |
| 6,471,721 B1 | 10/2002 | Dang |
| 6,471,980 B2 | 10/2002 | Sirhan et al. |
| 6,475,477 B1 | 11/2002 | Kohn et al. |
| 6,478,815 B1 | 11/2002 | Alt |
| 6,479,146 B1 | 11/2002 | Caruso et al. |
| 6,486,588 B2 | 11/2002 | Doron |
| 6,488,702 B1 | 12/2002 | Besselink |
| 6,491,666 B1 | 12/2002 | Santini, Jr. et al. |
| 6,491,720 B1 | 12/2002 | Vallana et al. |
| 6,492,096 B1 | 12/2002 | Liu et al. |
| 6,503,556 B2 | 1/2003 | Harish et al. |
| 6,503,921 B2 | 1/2003 | Naicker et al. |
| 6,506,437 B1 | 1/2003 | Harish et al. |
| 6,506,972 B1 | 1/2003 | Wang |
| 6,514,283 B2 | 2/2003 | DiMatteo et al. |
| 6,517,571 B1 | 2/2003 | Brauker et al. |
| 6,517,888 B1 | 2/2003 | Weber |
| 6,524,274 B1 | 2/2003 | Rosenthal et al. |
| 6,524,334 B1 | 2/2003 | Thompson |
| 6,527,801 B1 | 3/2003 | Dutta |
| 6,527,938 B2 | 3/2003 | Bales et al. |
| 6,530,949 B2 | 3/2003 | Konya et al. |
| 6,530,951 B1 | 3/2003 | Bates et al. |
| 6,537,310 B1 | 3/2003 | Palmaz et al. |
| 6,537,312 B2 | 3/2003 | Datta et al. |
| 6,544,582 B1 | 4/2003 | Yoe |
| 6,545,097 B2 | 4/2003 | Pinchuk et al. |
| 6,549,811 B2 | 4/2003 | Stewart et al. |
| 6,554,854 B1 | 4/2003 | Flanagan |
| 6,558,422 B1 | 5/2003 | Baker et al. |
| 6,558,733 B1 | 5/2003 | Hossainy et al. |
| 6,565,602 B2 | 5/2003 | Rolando et al. |
| 6,569,489 B1 | 5/2003 | Li |
| 6,584,349 B1 | 6/2003 | Sage et al. |
| 6,585,764 B2 | 7/2003 | Wright et al. |
| 6,585,765 B1 | 7/2003 | Hossainy et al. |
| 6,586,705 B1 | 7/2003 | Schell |
| 6,589,286 B1 | 7/2003 | Litner |
| 6,599,558 B1 | 7/2003 | Al-Lamee et al. |
| 6,602,287 B1 | 8/2003 | Millare et al. |
| 6,607,598 B2 | 8/2003 | Schwarz et al. |
| 6,613,077 B2 | 9/2003 | Gilligan et al. |
| 6,613,083 B2 | 9/2003 | Alt |
| 6,613,432 B2 | 9/2003 | Zamora et al. |
| 6,616,765 B1 | 9/2003 | Kruzel et al. |
| 6,626,933 B1 | 9/2003 | Lau et al. |
| 6,626,936 B2 | 9/2003 | Stinson |
| 6,626,939 B1 | 9/2003 | Burnside et al. |
| 6,627,321 B1 | 9/2003 | Ellingsen et al. |
| 6,628,989 B1 | 9/2003 | Penner |
| 6,629,992 B2 | 10/2003 | Bigus et al. |
| 6,635,082 B1 | 10/2003 | Hossainy et al. |
| 6,638,302 B1 | 10/2003 | Curcio et al. |
| 6,641,607 B1 | 11/2003 | Hossainy et al. |

| Patent | Date | Name |
|---|---|---|
| 6,652,575 B2 | 11/2003 | Wang |
| 6,652,578 B2 | 11/2003 | Bailey et al. |
| 6,652,581 B1 | 11/2003 | Ding |
| 6,652,582 B1 | 11/2003 | Stinson |
| 6,660,034 B1 | 12/2003 | Mandrusov et al. |
| 6,663,662 B2 | 12/2003 | Pacetti et al. |
| 6,663,664 B1 | 12/2003 | Pacetti |
| 6,669,980 B2 | 12/2003 | Hansen |
| 6,673,105 B1 | 1/2004 | Chen |
| 6,673,385 B1 | 1/2004 | Ding et al. |
| 6,673,999 B1 | 1/2004 | Wang et al. |
| 6,676,987 B2 | 1/2004 | Zhong |
| 6,676,989 B2 | 1/2004 | Kirkpatrick et al. |
| 6,689,160 B1 | 2/2004 | Okuda et al. |
| 6,689,803 B2 | 2/2004 | Hunter |
| 6,695,865 B2 | 2/2004 | Boyle et al. |
| 6,696,666 B2 | 2/2004 | Merdan et al. |
| 6,696,667 B1 | 2/2004 | Flanagan |
| 6,699,281 B2 | 3/2004 | Vallana et al. |
| 6,699,282 B1 | 3/2004 | Sceusa |
| 6,709,379 B1 | 3/2004 | Brandau et al. |
| 6,709,397 B2 | 3/2004 | Taylor |
| 6,709,451 B1 | 3/2004 | Noble et al. |
| 6,710,053 B2 | 3/2004 | Naicker et al. |
| 6,712,844 B2 | 3/2004 | Pacetti |
| 6,712,845 B2 | 3/2004 | Hossainy |
| 6,713,671 B1 | 3/2004 | Wang et al. |
| 6,716,444 B1 | 4/2004 | Castro et al. |
| 6,719,987 B2 | 4/2004 | Burrell et al. |
| 6,720,402 B2 | 4/2004 | Langer et al. |
| 6,723,120 B2 | 4/2004 | Yan |
| 6,723,350 B2 | 4/2004 | Burrell et al. |
| 6,725,901 B1 | 4/2004 | Kramer et al. |
| 6,726,712 B2 | 4/2004 | Raeder-Devens |
| 6,730,117 B1 | 5/2004 | Tseng et al. |
| 6,730,120 B2 | 5/2004 | Berg et al. |
| 6,730,699 B2 | 5/2004 | Li et al. |
| 6,733,513 B2 | 5/2004 | Boyle et al. |
| 6,740,077 B1 | 5/2004 | Brandau et al. |
| 6,743,388 B2 | 6/2004 | Sridharan et al. |
| 6,752,826 B2 | 6/2004 | Holloway et al. |
| 6,752,829 B2 | 6/2004 | Kocur et al. |
| 6,753,071 B1 | 6/2004 | Pacetti |
| 6,758,859 B1 | 7/2004 | Dang et al. |
| 6,764,505 B1 | 7/2004 | Hossainy et al. |
| 6,764,579 B2 | 7/2004 | Veerasamy et al. |
| 6,764,709 B2 | 7/2004 | Flanagan |
| 6,765,144 B1 | 7/2004 | Wang et al. |
| 6,767,360 B1 | 7/2004 | Alt et al. |
| 6,770,086 B1 | 8/2004 | Girton |
| 6,770,729 B2 | 8/2004 | Van Antwerp |
| 6,774,278 B1 | 8/2004 | Ragheb et al. |
| 6,776,022 B2 | 8/2004 | Kula et al. |
| 6,776,094 B1 | 8/2004 | Whitesides et al. |
| 6,776,793 B2 | 8/2004 | Brown et al. |
| 6,780,424 B2 | 8/2004 | Claude |
| 6,783,543 B2 | 8/2004 | Jang |
| 6,790,228 B2 | 9/2004 | Hossainy et al. |
| 6,793,877 B1 | 9/2004 | Pettersen et al. |
| 6,796,435 B2 | 9/2004 | Izumi |
| 6,803,070 B2 | 10/2004 | Weber |
| 6,805,709 B1 | 10/2004 | Schaldach et al. |
| 6,805,898 B1 | 10/2004 | Wu et al. |
| 6,807,440 B2 | 10/2004 | Weber |
| RE38,653 E | 11/2004 | Igaki et al. |
| 6,815,609 B1 | 11/2004 | Wang et al. |
| 6,820,676 B2 | 11/2004 | Palmaz et al. |
| 6,827,737 B2 | 12/2004 | Hill et al. |
| 6,827,966 B2 | 12/2004 | Qiu et al. |
| 6,833,004 B2 | 12/2004 | Ishii et al. |
| 6,846,323 B2 | 1/2005 | Yip et al. |
| 6,846,841 B2 | 1/2005 | Hunter et al. |
| 6,847,837 B1 | 1/2005 | Melzer et al. |
| 6,849,085 B2 | 2/2005 | Marton |
| 6,849,089 B2 | 2/2005 | Stoll |
| 6,852,122 B2 | 2/2005 | Rush |
| 6,854,172 B2 | 2/2005 | Kaese et al. |
| 6,861,088 B2 | 3/2005 | Weber et al. |
| 6,865,810 B2 | 3/2005 | Stinson |
| 6,866,805 B2 | 3/2005 | Hong et al. |
| 6,869,443 B2 | 3/2005 | Buscemi et al. |
| 6,869,701 B1 | 3/2005 | Aita et al. |
| 6,875,227 B2 | 4/2005 | Yoon |
| 6,878,249 B2 | 4/2005 | Kouyama et al. |
| 6,884,429 B2 | 4/2005 | Koziak et al. |
| 6,887,270 B2 | 5/2005 | Miller et al. |
| 6,887,857 B2 | 5/2005 | Naimark et al. |
| 6,896,697 B1 | 5/2005 | Yip et al. |
| 6,899,731 B2 | 5/2005 | Li et al. |
| 6,899,914 B2 | 5/2005 | Schaldach et al. |
| 6,904,658 B2 | 6/2005 | Hines |
| 6,908,506 B2 | 6/2005 | Zimmermann |
| 6,908,622 B2 | 6/2005 | Barry et al. |
| 6,908,624 B2 | 6/2005 | Hossainy et al. |
| 6,913,617 B1 | 7/2005 | Reiss |
| 6,913,765 B2 | 7/2005 | Li et al. |
| 6,918,869 B2 | 7/2005 | Shaw et al. |
| 6,918,927 B2 | 7/2005 | Bates et al. |
| 6,921,390 B2 | 7/2005 | Bucay-Couto et al. |
| 6,923,996 B2 | 8/2005 | Epstein et al. |
| 6,926,735 B2 | 8/2005 | Henderson |
| 6,932,930 B2 | 8/2005 | DeSimone et al. |
| 6,936,066 B2 | 8/2005 | Palmaz et al. |
| 6,939,320 B2 | 9/2005 | Lennox |
| 6,945,993 B2 | 9/2005 | Kveen et al. |
| 6,951,053 B2 | 10/2005 | Padilla et al. |
| 6,953,560 B1 | 10/2005 | Castro et al. |
| 6,953,594 B2 | 10/2005 | Lee et al. |
| 6,954,977 B2 | 10/2005 | Maguire et al. |
| 6,955,661 B1 | 10/2005 | Herweck et al. |
| 6,955,685 B2 | 10/2005 | Escamilla et al. |
| 6,962,822 B2 | 11/2005 | Hart et al. |
| 6,964,817 B2 | 11/2005 | Date et al. |
| 6,971,813 B2 | 12/2005 | Shekalim et al. |
| 6,972,130 B1 | 12/2005 | Lee et al. |
| 6,973,718 B2 | 12/2005 | Sheppard, Jr. et al. |
| 6,979,346 B1 | 12/2005 | Hossainy et al. |
| 6,979,347 B1 | 12/2005 | Wu et al. |
| 6,979,348 B2 | 12/2005 | Sundar |
| 6,981,986 B1 | 1/2006 | Brown et al. |
| 6,984,404 B1 | 1/2006 | Talton et al. |
| 6,986,899 B2 | 1/2006 | Hossainy et al. |
| 6,989,156 B2 | 1/2006 | Gillis |
| 6,991,709 B2 | 1/2006 | Gopalraja et al. |
| 7,001,421 B2 | 2/2006 | Cheng et al. |
| 7,004,968 B2 | 2/2006 | Lootz et al. |
| 7,011,670 B2 | 3/2006 | Radisch, Jr. |
| 7,011,678 B2 | 3/2006 | Tenerz et al. |
| 7,011,680 B2 | 3/2006 | Alt |
| 7,018,408 B2 | 3/2006 | Bailey et al. |
| 7,022,334 B1 | 4/2006 | Ding et al. |
| 7,041,130 B2 | 5/2006 | Santini, Jr. |
| 7,048,767 B2 | 5/2006 | Namavar |
| 7,048,939 B2 | 5/2006 | Elkins et al. |
| 7,052,488 B2 | 5/2006 | Uhland |
| 7,056,338 B2 | 6/2006 | Shanley et al. |
| 7,056,339 B2 | 6/2006 | Elkins et al. |
| 7,060,051 B2 | 6/2006 | Palasis |
| 7,060,240 B2 | 6/2006 | Costa et al. |
| 7,063,748 B2 | 6/2006 | Talton |
| 7,067,606 B2 | 6/2006 | Mather et al. |
| 7,070,576 B2 | 7/2006 | O'Brien et al. |
| 7,078,108 B2 | 7/2006 | Zhang et al. |
| 7,099,091 B2 | 8/2006 | Taniguchi et al. |
| 7,101,391 B2 | 9/2006 | Scheuermann et al. |
| 7,101,394 B2 | 9/2006 | Hamm et al. |
| 7,105,018 B1 | 9/2006 | Yip et al. |
| 7,105,199 B2 | 9/2006 | Blinn et al. |
| 7,108,716 B2 | 9/2006 | Burnside et al. |
| 7,157,096 B2 | 1/2007 | Zhang et al. |
| 7,160,592 B2 | 1/2007 | Rypacek et al. |
| 7,163,715 B1 | 1/2007 | Kramer |
| 7,169,173 B2 | 1/2007 | Hossainy et al. |
| 7,169,178 B1 | 1/2007 | Santos et al. |
| 7,195,640 B2 | 3/2007 | Falotico et al. |
| 7,195,641 B2 | 3/2007 | Palmaz et al. |
| 7,198,675 B2 | 4/2007 | Fox et al. |
| 7,208,011 B2 | 4/2007 | Shanley et al. |

| | | |
|---|---|---|
| 7,208,172 B2 | 4/2007 | Birdsall et al. |
| 7,220,816 B2 | 5/2007 | Pacetti |
| 7,226,475 B2 | 6/2007 | Lenz et al. |
| 7,229,471 B2 | 6/2007 | Gale et al. |
| 7,235,096 B1 | 6/2007 | Van Tassel et al. |
| 7,235,098 B2 | 6/2007 | Palmaz |
| 7,238,199 B2 | 7/2007 | Feldman et al. |
| 7,241,295 B2 | 7/2007 | Maguire |
| 7,244,272 B2 | 7/2007 | Dubson et al. |
| 7,261,732 B2 | 8/2007 | Justino |
| 7,261,735 B2 | 8/2007 | Llanos et al. |
| 7,267,960 B2 | 9/2007 | Galibert et al. |
| 7,279,174 B2 | 10/2007 | Pacetti |
| 7,279,175 B2 | 10/2007 | Chen |
| 7,294,409 B2 | 11/2007 | Lye et al. |
| 7,311,727 B2 | 12/2007 | Mazumder et al. |
| 7,323,189 B2 | 1/2008 | Pathak |
| RE40,122 E | 2/2008 | Thompson |
| 7,331,993 B2 | 2/2008 | White |
| 7,335,375 B2 | 2/2008 | Li et al. |
| 7,344,560 B2 | 3/2008 | Gregorich et al. |
| 7,344,563 B2 | 3/2008 | Vallana et al. |
| 7,393,589 B2 | 7/2008 | Aharonov et al. |
| 7,402,173 B2 | 7/2008 | Scheuermann et al. |
| 7,416,558 B2 | 8/2008 | Yip et al. |
| 7,432,327 B2 | 10/2008 | Glasgow et al. |
| 7,462,366 B2 | 12/2008 | Lanphere |
| 7,498,385 B2 | 3/2009 | Swetlin et al. |
| 7,507,433 B2 | 3/2009 | Weber |
| 7,537,610 B2 | 5/2009 | Reiss |
| 7,547,445 B2 | 6/2009 | Chudzik et al. |
| 7,563,277 B2 | 7/2009 | Case et al. |
| 7,637,941 B1 | 12/2009 | Manicka et al. |
| 7,641,983 B2 * | 1/2010 | Stinson .................. 428/546 |
| 7,651,527 B2 | 1/2010 | Krivoruchko et al. |
| 7,691,401 B2 | 4/2010 | Castro et al. |
| 7,749,264 B2 | 7/2010 | Gregorich et al. |
| 7,758,635 B2 | 7/2010 | Parsonage |
| 7,771,773 B2 | 8/2010 | Namavar |
| 7,776,926 B1 | 8/2010 | Claude et al. |
| 2001/0001834 A1 | 5/2001 | Palmaz et al. |
| 2001/0002000 A1 | 5/2001 | Kumar et al. |
| 2001/0002435 A1 | 5/2001 | Berg et al. |
| 2001/0013166 A1 | 8/2001 | Yan |
| 2001/0021871 A1 | 9/2001 | Stinson |
| 2001/0021873 A1 | 9/2001 | Stinson |
| 2001/0027299 A1 | 10/2001 | Yang et al. |
| 2001/0029398 A1 | 10/2001 | Jadhav |
| 2001/0029660 A1 | 10/2001 | Johnson |
| 2001/0032011 A1 | 10/2001 | Stanford |
| 2001/0032013 A1 | 10/2001 | Marton |
| 2001/0032014 A1 | 10/2001 | Yang et al. |
| 2001/0044650 A1 | 11/2001 | Simso et al. |
| 2002/0000175 A1 | 1/2002 | Hintermaier et al. |
| 2002/0000406 A1 | 1/2002 | Izumi |
| 2002/0004060 A1 * | 1/2002 | Heublein et al. .............. 424/422 |
| 2002/0007102 A1 | 1/2002 | Salmon et al. |
| 2002/0007209 A1 | 1/2002 | Scheerder et al. |
| 2002/0010505 A1 | 1/2002 | Richter |
| 2002/0016623 A1 | 2/2002 | Kula et al. |
| 2002/0016624 A1 | 2/2002 | Patterson et al. |
| 2002/0028827 A1 | 3/2002 | Naicker et al. |
| 2002/0032477 A1 | 3/2002 | Helmus et al. |
| 2002/0035394 A1 | 3/2002 | Fierens et al. |
| 2002/0038146 A1 | 3/2002 | Harry |
| 2002/0042039 A1 | 4/2002 | Kim et al. |
| 2002/0049495 A1 | 4/2002 | Kutryk et al. |
| 2002/0051730 A1 | 5/2002 | Bodnar et al. |
| 2002/0051846 A1 | 5/2002 | Kirkpatrick et al. |
| 2002/0065553 A1 | 5/2002 | Weber |
| 2002/0082679 A1 | 6/2002 | Sirhan et al. |
| 2002/0087123 A1 | 7/2002 | Hossainy et al. |
| 2002/0090313 A1 | 7/2002 | Wang et al. |
| 2002/0091375 A1 | 7/2002 | Sahatjian et al. |
| 2002/0098278 A1 | 7/2002 | Bates et al. |
| 2002/0099434 A1 | 7/2002 | Buscemi et al. |
| 2002/0099438 A1 | 7/2002 | Furst |
| 2002/0103527 A1 | 8/2002 | Kocur et al. |
| 2002/0103528 A1 | 8/2002 | Schaldach et al. |
| 2002/0111694 A1 | 8/2002 | Ellingsen et al. |
| 2002/0121497 A1 | 9/2002 | Tomonto |
| 2002/0123801 A1 | 9/2002 | Pacetti et al. |
| 2002/0133222 A1 | 9/2002 | Das |
| 2002/0133224 A1 | 9/2002 | Bajgar et al. |
| 2002/0138100 A1 | 9/2002 | Stoll et al. |
| 2002/0138131 A1 | 9/2002 | Solovay et al. |
| 2002/0138136 A1 | 9/2002 | Chandresekaran et al. |
| 2002/0138154 A1 | 9/2002 | Li et al. |
| 2002/0144757 A1 | 10/2002 | Craig et al. |
| 2002/0155212 A1 | 10/2002 | Hossainy |
| 2002/0165265 A1 | 11/2002 | Hunter et al. |
| 2002/0165578 A1 | 11/2002 | Sawitowski et al. |
| 2002/0165600 A1 | 11/2002 | Banas et al. |
| 2002/0165607 A1 | 11/2002 | Alt |
| 2002/0169493 A1 | 11/2002 | Widenhouse et al. |
| 2002/0178570 A1 | 12/2002 | Sogard et al. |
| 2002/0182241 A1 | 12/2002 | Borenstein et al. |
| 2002/0183581 A1 | 12/2002 | Yoe et al. |
| 2002/0187260 A1 | 12/2002 | Sheppard, Jr. et al. |
| 2002/0193336 A1 | 12/2002 | Elkins et al. |
| 2002/0193682 A1 | 12/2002 | Torchia et al. |
| 2002/0193869 A1 | 12/2002 | Dang |
| 2002/0197178 A1 | 12/2002 | Yan |
| 2002/0198601 A1 | 12/2002 | Bales et al. |
| 2003/0003127 A1 | 1/2003 | Brown et al. |
| 2003/0003220 A1 | 1/2003 | Zhong et al. |
| 2003/0004563 A1 | 1/2003 | Jackson et al. |
| 2003/0004564 A1 | 1/2003 | Elkins et al. |
| 2003/0009214 A1 | 1/2003 | Shanley |
| 2003/0018380 A1 | 1/2003 | Craig et al. |
| 2003/0018381 A1 | 1/2003 | Whitcher et al. |
| 2003/0023300 A1 | 1/2003 | Bailey et al. |
| 2003/0028242 A1 | 2/2003 | Vallana et al. |
| 2003/0028243 A1 | 2/2003 | Bates et al. |
| 2003/0032892 A1 | 2/2003 | Erlach et al. |
| 2003/0033007 A1 | 2/2003 | Sirhan et al. |
| 2003/0044446 A1 | 3/2003 | Moro et al. |
| 2003/0044596 A1 | 3/2003 | Lazarov et al. |
| 2003/0050687 A1 | 3/2003 | Schwade et al. |
| 2003/0059640 A1 | 3/2003 | Marton et al. |
| 2003/0060871 A1 | 3/2003 | Hill et al. |
| 2003/0060873 A1 | 3/2003 | Gertner et al. |
| 2003/0064095 A1 | 4/2003 | Martin et al. |
| 2003/0068355 A1 | 4/2003 | Shanley et al. |
| 2003/0069631 A1 | 4/2003 | Stoll |
| 2003/0074053 A1 | 4/2003 | Palmaz et al. |
| 2003/0077200 A1 | 4/2003 | Craig et al. |
| 2003/0077310 A1 | 4/2003 | Pathak et al. |
| 2003/0083614 A1 | 5/2003 | Eisert |
| 2003/0083646 A1 | 5/2003 | Sirhan et al. |
| 2003/0083731 A1 | 5/2003 | Kramer et al. |
| 2003/0087024 A1 | 5/2003 | Flanagan |
| 2003/0088307 A1 | 5/2003 | Shulze et al. |
| 2003/0088312 A1 | 5/2003 | Kopia et al. |
| 2003/0099684 A1 | 5/2003 | Domb |
| 2003/0100815 A1 | 5/2003 | Da Silva et al. |
| 2003/0100830 A1 | 5/2003 | Zhong et al. |
| 2003/0104030 A1 | 6/2003 | Igaki et al. |
| 2003/0105511 A1 | 6/2003 | Welsh et al. |
| 2003/0108659 A1 | 6/2003 | Bales et al. |
| 2003/0114917 A1 | 6/2003 | Holloway et al. |
| 2003/0114921 A1 | 6/2003 | Yoon |
| 2003/0118692 A1 | 6/2003 | Wang et al. |
| 2003/0120339 A1 | 6/2003 | Banik et al. |
| 2003/0124055 A1 | 7/2003 | Li et al. |
| 2003/0125803 A1 | 7/2003 | Vallana |
| 2003/0130718 A1 | 7/2003 | Palmas et al. |
| 2003/0139799 A1 | 7/2003 | Ley et al. |
| 2003/0143330 A1 | 7/2003 | Loomis et al. |
| 2003/0144728 A1 | 7/2003 | Scheuermann et al. |
| 2003/0150380 A1 | 8/2003 | Yoe |
| 2003/0153901 A1 | 8/2003 | Herweck et al. |
| 2003/0158598 A1 | 8/2003 | Ashton et al. |
| 2003/0170605 A1 | 9/2003 | Long et al. |
| 2003/0181975 A1 | 9/2003 | Ishii et al. |
| 2003/0185895 A1 | 10/2003 | Lanphere |
| 2003/0190406 A1 | 10/2003 | Hossainy et al. |
| 2003/0195613 A1 | 10/2003 | Curcio et al. |

| | | | | | | |
|---|---|---|---|---|---|---|
| 2003/0204239 A1 | 10/2003 | Carlyle et al. | 2004/0220510 A1 | 11/2004 | Koullick et al. | |
| 2003/0211135 A1 | 11/2003 | Greenhalgh et al. | 2004/0220659 A1 | 11/2004 | Girton | |
| 2003/0216803 A1 | 11/2003 | Ledergerber | 2004/0220660 A1 | 11/2004 | Shanley et al. | |
| 2003/0219562 A1 | 11/2003 | Rypacek et al. | 2004/0220662 A1 | 11/2004 | Dang et al. | |
| 2003/0221307 A1 | 12/2003 | Kaese et al. | 2004/0224001 A1 | 11/2004 | Pacetti et al. | |
| 2003/0228523 A1 | 12/2003 | DeLongchamp et al. | 2004/0225346 A1 | 11/2004 | Mazumder et al. | |
| 2003/0236513 A1 | 12/2003 | Schwarz et al. | 2004/0228905 A1 | 11/2004 | Greenspan et al. | |
| 2004/0000046 A1 | 1/2004 | Stinson | 2004/0230176 A1 | 11/2004 | Shanahan et al. | |
| 2004/0000540 A1 | 1/2004 | Soboyejo et al. | 2004/0230225 A1 | 11/2004 | Penner et al. | |
| 2004/0004063 A1 | 1/2004 | Merdan | 2004/0230290 A1 | 11/2004 | Weber et al. | |
| 2004/0006382 A1 | 1/2004 | Sohier | 2004/0230293 A1 | 11/2004 | Yip et al. | |
| 2004/0018296 A1 | 1/2004 | Castro et al. | 2004/0234737 A1 | 11/2004 | Pacetti | |
| 2004/0019376 A1 | 1/2004 | Alt | 2004/0236415 A1 | 11/2004 | Thomas | |
| 2004/0022939 A1 | 2/2004 | Kim et al. | 2004/0236416 A1 | 11/2004 | Falotico | |
| 2004/0024448 A1 | 2/2004 | Chang et al. | 2004/0237282 A1 | 12/2004 | Hines | |
| 2004/0029303 A1 | 2/2004 | Hart et al. | 2004/0242106 A1 | 12/2004 | Rabasco et al. | |
| 2004/0030218 A1 | 2/2004 | Kocur et al. | 2004/0243217 A1 | 12/2004 | Andersen et al. | |
| 2004/0030377 A1 | 2/2004 | Dubson et al. | 2004/0243237 A1* | 12/2004 | Unwin et al. | 623/17.11 |
| 2004/0034409 A1 | 2/2004 | Heublein et al. | 2004/0243241 A1* | 12/2004 | Istephanous et al. | 623/17.14 |
| 2004/0039438 A1 | 2/2004 | Alt | 2004/0247671 A1 | 12/2004 | Prescott et al. | |
| 2004/0039441 A1 | 2/2004 | Rowland et al. | 2004/0249440 A1 | 12/2004 | Bucker et al. | |
| 2004/0044397 A1 | 3/2004 | Stinson | 2004/0249443 A1 | 12/2004 | Shanley et al. | |
| 2004/0047980 A1 | 3/2004 | Pacetti et al. | 2004/0249444 A1 | 12/2004 | Reiss | |
| 2004/0059407 A1 | 3/2004 | Escamilla et al. | 2004/0249445 A1 | 12/2004 | Rosenthal et al. | |
| 2004/0059409 A1 | 3/2004 | Stenzel | 2004/0249449 A1 | 12/2004 | Shanley et al. | |
| 2004/0067301 A1 | 4/2004 | Ding | 2004/0254419 A1 | 12/2004 | Wang et al. | |
| 2004/0071861 A1 | 4/2004 | Mandrusov et al. | 2004/0254635 A1 | 12/2004 | Shanley et al. | |
| 2004/0073155 A1 | 4/2004 | Laufer et al. | 2005/0004661 A1 | 1/2005 | Lewis et al. | |
| 2004/0073284 A1 | 4/2004 | Bates et al. | 2005/0010275 A1 | 1/2005 | Sahatjian | |
| 2004/0073293 A1 | 4/2004 | Thompson | 2005/0010279 A1 | 1/2005 | Tenerz et al. | |
| 2004/0073297 A1 | 4/2004 | Rohde et al. | 2005/0015142 A1 | 1/2005 | Austin et al. | |
| 2004/0073298 A1 | 4/2004 | Hossainy | 2005/0019265 A1 | 1/2005 | Hammer et al. | |
| 2004/0078071 A1 | 4/2004 | Escamilla et al. | 2005/0019371 A1 | 1/2005 | Anderson et al. | |
| 2004/0082682 A1 | 4/2004 | Loomis et al. | 2005/0021127 A1 | 1/2005 | Kawula | |
| 2004/0088038 A1 | 5/2004 | Dehnad et al. | 2005/0021128 A1 | 1/2005 | Nakahama et al. | |
| 2004/0088041 A1 | 5/2004 | Stanford | 2005/0022627 A1 | 2/2005 | Chen | |
| 2004/0093071 A1 | 5/2004 | Jang | 2005/0027350 A1 | 2/2005 | Momma et al. | |
| 2004/0093075 A1 | 5/2004 | Kuehne | 2005/0033407 A1 | 2/2005 | Weber et al. | |
| 2004/0093076 A1 | 5/2004 | White et al. | 2005/0033411 A1 | 2/2005 | Wu et al. | |
| 2004/0098089 A1 | 5/2004 | Weber | 2005/0033412 A1 | 2/2005 | Wu et al. | |
| 2004/0098108 A1 | 5/2004 | Harder et al. | 2005/0033417 A1 | 2/2005 | Borges et al. | |
| 2004/0098119 A1 | 5/2004 | Wang | 2005/0037047 A1 | 2/2005 | Song | |
| 2004/0106975 A1 | 6/2004 | Solovay et al. | 2005/0037050 A1 | 2/2005 | Weber | |
| 2004/0106984 A1 | 6/2004 | Stinson | 2005/0038134 A1 | 2/2005 | Loomis et al. | |
| 2004/0106985 A1 | 6/2004 | Jang | 2005/0038501 A1 | 2/2005 | Moore, Jr. et al. | |
| 2004/0111150 A1 | 6/2004 | Berg et al. | 2005/0042288 A1 | 2/2005 | Koblish et al. | |
| 2004/0116999 A1 | 6/2004 | Ledergerber | 2005/0042440 A1 | 2/2005 | Bach et al. | |
| 2004/0117005 A1 | 6/2004 | Gadde et al. | 2005/0055044 A1 | 3/2005 | Kangas | |
| 2004/0117008 A1 | 6/2004 | Wnendt et al. | 2005/0055080 A1 | 3/2005 | Istephanous et al. | |
| 2004/0122504 A1 | 6/2004 | Hogendijk | 2005/0055085 A1 | 3/2005 | Rivron et al. | |
| 2004/0126566 A1 | 7/2004 | Axen et al. | 2005/0060020 A1 | 3/2005 | Jenson | |
| 2004/0133270 A1 | 7/2004 | Grandt | 2005/0060021 A1 | 3/2005 | O'Brien et al. | |
| 2004/0134886 A1 | 7/2004 | Wagner et al. | 2005/0064088 A1 | 3/2005 | Fredrickson | |
| 2004/0137039 A1 | 7/2004 | Sukhishvili et al. | 2005/0069630 A1 | 3/2005 | Fox et al. | |
| 2004/0138738 A1 | 7/2004 | Stinson | 2005/0070989 A1 | 3/2005 | Lye et al. | |
| 2004/0142014 A1 | 7/2004 | Litvack et al. | 2005/0070990 A1 | 3/2005 | Stinson | |
| 2004/0143317 A1 | 7/2004 | Stinson et al. | 2005/0070996 A1 | 3/2005 | Dinh et al. | |
| 2004/0143321 A1 | 7/2004 | Litvack et al. | 2005/0071016 A1 | 3/2005 | Hausdorf et al. | |
| 2004/0148010 A1 | 7/2004 | Rush | 2005/0072544 A1 | 4/2005 | Palmaz et al. | |
| 2004/0148015 A1 | 7/2004 | Lye et al. | 2005/0074479 A1 | 4/2005 | Weber et al. | |
| 2004/0153138 A1 | 8/2004 | Murphy | 2005/0074545 A1 | 4/2005 | Thomas | |
| 2004/0157073 A1 | 8/2004 | Burrell et al. | 2005/0075714 A1 | 4/2005 | Cheng et al. | |
| 2004/0158308 A1 | 8/2004 | Hogendijk et al. | 2005/0077305 A1 | 4/2005 | Guevara | |
| 2004/0158310 A1 | 8/2004 | Weber et al. | 2005/0079132 A1 | 4/2005 | Wang et al. | |
| 2004/0167572 A1 | 8/2004 | Roth et al. | 2005/0079199 A1 | 4/2005 | Heruth et al. | |
| 2004/0167612 A1 | 8/2004 | Grignani et al. | 2005/0079356 A1 | 4/2005 | Rathenow et al. | |
| 2004/0172124 A1 | 9/2004 | Vallana et al. | 2005/0092615 A1 | 5/2005 | Birdsall et al. | |
| 2004/0181252 A1 | 9/2004 | Boyle et al. | 2005/0096731 A1 | 5/2005 | Looi et al. | |
| 2004/0181275 A1 | 9/2004 | Noble et al. | 2005/0100577 A1 | 5/2005 | Parker et al. | |
| 2004/0181276 A1 | 9/2004 | Brown et al. | 2005/0100609 A1 | 5/2005 | Claude | |
| 2004/0181278 A1 | 9/2004 | Tseng et al. | 2005/0102025 A1 | 5/2005 | Laroche et al. | |
| 2004/0182511 A1 | 9/2004 | Rakos et al. | 2005/0106212 A1 | 5/2005 | Gertner et al. | |
| 2004/0186553 A1 | 9/2004 | Yan | 2005/0107869 A1 | 5/2005 | Sirhan et al. | |
| 2004/0191293 A1 | 9/2004 | Claude | 2005/0107870 A1 | 5/2005 | Wang et al. | |
| 2004/0191404 A1 | 9/2004 | Hossainy et al. | 2005/0113936 A1 | 5/2005 | Brustad et al. | |
| 2004/0202692 A1 | 10/2004 | Shanley et al. | 2005/0119723 A1 | 6/2005 | Peacock | |
| 2004/0204750 A1 | 10/2004 | Dinh | 2005/0129727 A1 | 6/2005 | Weber et al. | |
| 2004/0211362 A1 | 10/2004 | Castro et al. | 2005/0129731 A1 | 6/2005 | Horres et al. | |
| 2004/0219214 A1 | 11/2004 | Gravett et al. | 2005/0131509 A1 | 6/2005 | Atanassoska et al. | |

| Pub. No. | Date | Inventor |
|---|---|---|
| 2005/0131521 A1 | 6/2005 | Marton |
| 2005/0131522 A1 | 6/2005 | Stinson et al. |
| 2005/0131527 A1 | 6/2005 | Pathak |
| 2005/0131528 A1 | 6/2005 | Buscemi et al. |
| 2005/0136090 A1 | 6/2005 | Falotico et al. |
| 2005/0137677 A1 | 6/2005 | Rush |
| 2005/0137679 A1 | 6/2005 | Changelian et al. |
| 2005/0137684 A1 | 6/2005 | Changelian et al. |
| 2005/0149169 A1 | 7/2005 | Wang et al. |
| 2005/0149170 A1 | 7/2005 | Tassel et al. |
| 2005/0149175 A1 | 7/2005 | Hunter et al. |
| 2005/0149177 A1 | 7/2005 | Weber et al. |
| 2005/0159804 A1 | 7/2005 | Lad et al. |
| 2005/0159805 A1 | 7/2005 | Weber et al. |
| 2005/0159809 A1 | 7/2005 | Hezi-Yamit et al. |
| 2005/0160600 A1 | 7/2005 | Bien et al. |
| 2005/0163821 A1 | 7/2005 | Sung et al. |
| 2005/0163954 A1 | 7/2005 | Shaw |
| 2005/0165301 A1 | 7/2005 | Smith et al. |
| 2005/0165468 A1 | 7/2005 | Marton |
| 2005/0165470 A1 | 7/2005 | Weber |
| 2005/0169969 A1 | 8/2005 | Li et al. |
| 2005/0171595 A1 | 8/2005 | Feldman et al. |
| 2005/0177226 A1 | 8/2005 | Banik et al. |
| 2005/0180919 A1 | 8/2005 | Tedeschi |
| 2005/0182361 A1 | 8/2005 | Lennox |
| 2005/0182478 A1 | 8/2005 | Holman et al. |
| 2005/0186250 A1 | 8/2005 | Gertner et al. |
| 2005/0187605 A1 | 8/2005 | Greenhalgh et al. |
| 2005/0187611 A1 | 8/2005 | Ding et al. |
| 2005/0192657 A1 | 9/2005 | Colen et al. |
| 2005/0192662 A1 | 9/2005 | Ward |
| 2005/0192664 A1 | 9/2005 | Eisert |
| 2005/0196424 A1 | 9/2005 | Chappa |
| 2005/0208098 A1 | 9/2005 | Castro et al. |
| 2005/0208100 A1 | 9/2005 | Weber et al. |
| 2005/0209680 A1 | 9/2005 | Gale et al. |
| 2005/0209681 A1 | 9/2005 | Curcio et al. |
| 2005/0211680 A1 | 9/2005 | Li et al. |
| 2005/0214951 A1 | 9/2005 | Nahm et al. |
| 2005/0216074 A1 | 9/2005 | Sahatjian |
| 2005/0216075 A1 | 9/2005 | Wang et al. |
| 2005/0220853 A1 | 10/2005 | Dao et al. |
| 2005/0221072 A1 | 10/2005 | Dubrow et al. |
| 2005/0222671 A1 | 10/2005 | Schaeffer et al. |
| 2005/0224003 A1 | 10/2005 | Yin et al. |
| 2005/0228477 A1 | 10/2005 | Grainger et al. |
| 2005/0228483 A1 | 10/2005 | Kaplan et al. |
| 2005/0228491 A1 | 10/2005 | Snyder et al. |
| 2005/0232968 A1 | 10/2005 | Palmaz et al. |
| 2005/0233965 A1 | 10/2005 | Schwartz et al. |
| 2005/0234538 A1 | 10/2005 | Litvack et al. |
| 2005/0244459 A1 | 11/2005 | DeWitt et al. |
| 2005/0251245 A1 | 11/2005 | Sieradzki et al. |
| 2005/0251249 A1 | 11/2005 | Sahatjian |
| 2005/0252893 A1 | 11/2005 | Shapovalov et al. |
| 2005/0255707 A1 | 11/2005 | Hart et al. |
| 2005/0261760 A1 | 11/2005 | Weber |
| 2005/0266039 A1 | 12/2005 | Weber |
| 2005/0266040 A1 | 12/2005 | Gerberding |
| 2005/0266041 A1 | 12/2005 | Gerold et al. |
| 2005/0267560 A1 | 12/2005 | Bates et al. |
| 2005/0267561 A1 | 12/2005 | Jones et al. |
| 2005/0271706 A1 | 12/2005 | Anderson et al. |
| 2005/0276837 A1 | 12/2005 | Anderson et al. |
| 2005/0278016 A1 | 12/2005 | Welsh et al. |
| 2005/0278021 A1 | 12/2005 | Bates et al. |
| 2005/0281863 A1 | 12/2005 | Anderson et al. |
| 2005/0283224 A1 | 12/2005 | King |
| 2005/0283229 A1 | 12/2005 | Dugan et al. |
| 2005/0287188 A1 | 12/2005 | Anderson et al. |
| 2006/0002979 A1 | 1/2006 | Ashammakhi et al. |
| 2006/0009839 A1 | 1/2006 | Tan |
| 2006/0013850 A1 | 1/2006 | Domb |
| 2006/0014039 A1 | 1/2006 | Zhang et al. |
| 2006/0015175 A1 | 1/2006 | Palmaz et al. |
| 2006/0015361 A1 | 1/2006 | Sattler et al. |
| 2006/0020742 A1 | 1/2006 | Au et al. |
| 2006/0025848 A1 | 2/2006 | Weber et al. |
| 2006/0035026 A1 | 2/2006 | Atanassoska et al. |
| 2006/0036281 A1 | 2/2006 | Patterson et al. |
| 2006/0036311 A1 | 2/2006 | Nakayama et al. |
| 2006/0038027 A1 | 2/2006 | O'Connor et al. |
| 2006/0040388 A1 | 2/2006 | Bromberg et al. |
| 2006/0041182 A1 | 2/2006 | Forbes et al. |
| 2006/0051397 A1 | 3/2006 | Maier et al. |
| 2006/0052744 A1 | 3/2006 | Weber |
| 2006/0052863 A1 | 3/2006 | Harder et al. |
| 2006/0052864 A1 | 3/2006 | Harder et al. |
| 2006/0058868 A1 | 3/2006 | Gale et al. |
| 2006/0062820 A1 | 3/2006 | Gertner et al. |
| 2006/0064160 A1 | 3/2006 | Gerold et al. |
| 2006/0067908 A1 | 3/2006 | Ding |
| 2006/0069427 A1 | 3/2006 | Savage et al. |
| 2006/0075044 A1 | 4/2006 | Fox et al. |
| 2006/0075092 A1 | 4/2006 | Kidokoro |
| 2006/0079958 A1 | 4/2006 | Stratford et al. |
| 2006/0085062 A1 | 4/2006 | Lee et al. |
| 2006/0085065 A1 | 4/2006 | Krause et al. |
| 2006/0088566 A1 | 4/2006 | Parsonage et al. |
| 2006/0088567 A1 | 4/2006 | Warner et al. |
| 2006/0088653 A1 | 4/2006 | Chappa et al. |
| 2006/0088666 A1 | 4/2006 | Kobrin et al. |
| 2006/0100696 A1 | 5/2006 | Atanasoska et al. |
| 2006/0115512 A1 | 6/2006 | Peacock et al. |
| 2006/0118236 A1 | 6/2006 | House et al. |
| 2006/0121080 A1 | 6/2006 | Lye et al. |
| 2006/0122694 A1* | 6/2006 | Stinson et al. ............... 623/1.34 |
| 2006/0122697 A1 | 6/2006 | Shanley et al. |
| 2006/0124472 A1 | 6/2006 | Rokicki |
| 2006/0127266 A1 | 6/2006 | Miura et al. |
| 2006/0129215 A1 | 6/2006 | Helmus et al. |
| 2006/0129222 A1 | 6/2006 | Stinson |
| 2006/0129225 A1 | 6/2006 | Kopia et al. |
| 2006/0136048 A1 | 6/2006 | Pacetti et al. |
| 2006/0136051 A1 | 6/2006 | Furst et al. |
| 2006/0141156 A1 | 6/2006 | Viel et al. |
| 2006/0149352 A1 | 7/2006 | Schlum |
| 2006/0153729 A1 | 7/2006 | Stinson et al. |
| 2006/0155361 A1 | 7/2006 | Schomig et al. |
| 2006/0167543 A1 | 7/2006 | Bailey et al. |
| 2006/0177480 A1 | 8/2006 | Sung et al. |
| 2006/0178727 A1 | 8/2006 | Richter |
| 2006/0184235 A1 | 8/2006 | Rivron et al. |
| 2006/0193886 A1 | 8/2006 | Owens et al. |
| 2006/0193887 A1 | 8/2006 | Owens et al. |
| 2006/0193888 A1 | 8/2006 | Lye et al. |
| 2006/0193889 A1 | 8/2006 | Spradlin et al. |
| 2006/0193890 A1 | 8/2006 | Owens et al. |
| 2006/0193892 A1 | 8/2006 | Furst et al. |
| 2006/0195142 A1 | 8/2006 | Shalaby |
| 2006/0198869 A1 | 9/2006 | Furst et al. |
| 2006/0199876 A1 | 9/2006 | Troczynski et al. |
| 2006/0200229 A1 | 9/2006 | Burgermeister et al. |
| 2006/0200231 A1 | 9/2006 | O'Brien et al. |
| 2006/0200232 A1 | 9/2006 | Phaneuf et al. |
| 2006/0200233 A1 | 9/2006 | Kujawski |
| 2006/0204441 A1 | 9/2006 | Atala et al. |
| 2006/0204445 A1 | 9/2006 | Atala et al. |
| 2006/0210595 A1 | 9/2006 | Singhvi et al. |
| 2006/0212108 A1 | 9/2006 | Tittelbach |
| 2006/0222679 A1 | 10/2006 | Shanley et al. |
| 2006/0222844 A1 | 10/2006 | Stinson |
| 2006/0224237 A1 | 10/2006 | Furst et al. |
| 2006/0229711 A1 | 10/2006 | Yan et al. |
| 2006/0229713 A1 | 10/2006 | Shanley et al. |
| 2006/0230476 A1 | 10/2006 | Atanasoska et al. |
| 2006/0233941 A1 | 10/2006 | Olson |
| 2006/0241739 A1 | 10/2006 | Besselink et al. |
| 2006/0251701 A1 | 11/2006 | Lynn et al. |
| 2006/0259133 A1 | 11/2006 | Sowinski et al. |
| 2006/0264138 A1 | 11/2006 | Sowinski et al. |
| 2006/0271156 A1 | 11/2006 | Ledergerber |
| 2006/0271168 A1 | 11/2006 | Kleine et al. |
| 2006/0271169 A1 | 11/2006 | Lye et al. |
| 2006/0271192 A1 | 11/2006 | Olsen et al. |
| 2006/0275554 A1 | 12/2006 | Zhao et al. |
| 2006/0276877 A1 | 12/2006 | Owens et al. |

| | | | | | | |
|---|---|---|---|---|---|---|
| 2006/0276878 A1 | 12/2006 | Owens et al. | | 2007/0281073 A1 | 12/2007 | Gale et al. |
| 2006/0276879 A1 | 12/2006 | Lye et al. | | 2007/0281117 A1 | 12/2007 | Kaplan et al. |
| 2006/0276884 A1 | 12/2006 | Lye et al. | | 2007/0282432 A1 | 12/2007 | Stinson et al. |
| 2006/0276885 A1 | 12/2006 | Lye et al. | | 2007/0299509 A1 | 12/2007 | Ding |
| 2006/0280770 A1 | 12/2006 | Hossainy et al. | | 2007/0299512 A1 | 12/2007 | Korzuschnik et al. |
| 2006/0287709 A1 | 12/2006 | Rao | | 2008/0003251 A1 | 1/2008 | Zhou |
| 2006/0292388 A1 | 12/2006 | Palumbo et al. | | 2008/0003256 A1 | 1/2008 | Martens et al. |
| 2007/0003589 A1 | 1/2007 | Astafieva et al. | | 2008/0003431 A1 | 1/2008 | Fellinger et al. |
| 2007/0003596 A1 | 1/2007 | Tittelbach et al. | | 2008/0004691 A1 | 1/2008 | Weber et al. |
| 2007/0020306 A1 | 1/2007 | Schultheiss | | 2008/0031765 A1 | 2/2008 | Gerold et al. |
| 2007/0027532 A1 | 2/2007 | Wang et al. | | 2008/0033522 A1 | 2/2008 | Grewe et al. |
| 2007/0032858 A1 | 2/2007 | Santos et al. | | 2008/0033530 A1 | 2/2008 | Zberg et al. |
| 2007/0032862 A1 | 2/2007 | Weber et al. | | 2008/0033531 A1 | 2/2008 | Barthel et al. |
| 2007/0032864 A1 | 2/2007 | Furst et al. | | 2008/0033533 A1 | 2/2008 | Borck |
| 2007/0034615 A1 | 2/2007 | Kleine | | 2008/0033536 A1 | 2/2008 | Wittchow |
| 2007/0036905 A1 | 2/2007 | Kramer | | 2008/0033537 A1 | 2/2008 | Tittelbach |
| 2007/0038176 A1 | 2/2007 | Weber et al. | | 2008/0033538 A1 | 2/2008 | Borck et al. |
| 2007/0038289 A1 | 2/2007 | Nishide et al. | | 2008/0033539 A1 | 2/2008 | Sternberg et al. |
| 2007/0038290 A1 | 2/2007 | Huang et al. | | 2008/0033576 A1 | 2/2008 | Gerold et al. |
| 2007/0045252 A1 | 3/2007 | Kleine et al. | | 2008/0038146 A1 | 2/2008 | Wachter et al. |
| 2007/0048350 A1 | 3/2007 | Falotico et al. | | 2008/0050413 A1 | 2/2008 | Horvers et al. |
| 2007/0050007 A1 | 3/2007 | Kondyurin et al. | | 2008/0051335 A1 | 2/2008 | Kleiner et al. |
| 2007/0050009 A1 | 3/2007 | Flanagan | | 2008/0051866 A1 | 2/2008 | Chen et al. |
| 2007/0052497 A1 | 3/2007 | Tada | | 2008/0051872 A1 | 2/2008 | Borck |
| 2007/0055349 A1 | 3/2007 | Santos et al. | | 2008/0051881 A1 | 2/2008 | Feng et al. |
| 2007/0055354 A1 | 3/2007 | Santos et al. | | 2008/0057105 A1 | 3/2008 | Atanasoska et al. |
| 2007/0055364 A1 | 3/2007 | Hossainy et al. | | 2008/0058919 A1 | 3/2008 | Kramer-Brown et al. |
| 2007/0059435 A1 | 3/2007 | Santos et al. | | 2008/0058921 A1 | 3/2008 | Lindquist |
| 2007/0065418 A1 | 3/2007 | Vallana et al. | | 2008/0058923 A1 | 3/2008 | Bertsch et al. |
| 2007/0073385 A1 | 3/2007 | Schaeffer et al. | | 2008/0069854 A1 | 3/2008 | Xiao et al. |
| 2007/0073390 A1 | 3/2007 | Lee | | 2008/0069858 A1 | 3/2008 | Weber |
| 2007/0077163 A1* | 4/2007 | Furst et al. .................. 419/28 | | 2008/0071348 A1 | 3/2008 | Boismier et al. |
| 2007/0100385 A1 | 5/2007 | Rawat et al. | | 2008/0071349 A1 | 3/2008 | Atanasoska et al. |
| 2007/0104753 A1 | 5/2007 | Flanagan | | 2008/0071350 A1 | 3/2008 | Stinson |
| 2007/0106347 A1 | 5/2007 | Lin | | 2008/0071351 A1 | 3/2008 | Flanagan et al. |
| 2007/0106363 A1 | 5/2007 | Weber | | 2008/0071352 A1 | 3/2008 | Weber et al. |
| 2007/0123131 A1 | 5/2007 | Nguyen et al. | | 2008/0071353 A1 | 3/2008 | Weber et al. |
| 2007/0123973 A1 | 5/2007 | Roth et al. | | 2008/0071355 A1 | 3/2008 | Weber et al. |
| 2007/0129789 A1 | 6/2007 | Cottone, Jr. et al. | | 2008/0071357 A1 | 3/2008 | Girton et al. |
| 2007/0129792 A1 | 6/2007 | Picart et al. | | 2008/0071358 A1 | 3/2008 | Weber et al. |
| 2007/0134288 A1 | 6/2007 | Parsonage et al. | | 2008/0082162 A1 | 4/2008 | Boismier et al. |
| 2007/0135908 A1 | 6/2007 | Zhao | | 2008/0086199 A1 | 4/2008 | Dave et al. |
| 2007/0141106 A1 | 6/2007 | Bonutti et al. | | 2008/0086201 A1 | 4/2008 | Weber et al. |
| 2007/0142897 A1 | 6/2007 | Consigny et al. | | 2008/0090097 A1 | 4/2008 | Shaw et al. |
| 2007/0142899 A1 | 6/2007 | Lootz et al. | | 2008/0097577 A1 | 4/2008 | Atanasoska et al. |
| 2007/0148251 A1 | 6/2007 | Hossainy et al. | | 2008/0103589 A1 | 5/2008 | Cheng et al. |
| 2007/0151093 A1 | 7/2007 | Curcio et al. | | 2008/0103594 A1 | 5/2008 | Loffler et al. |
| 2007/0156231 A1 | 7/2007 | Weber | | 2008/0107890 A1 | 5/2008 | Bureau et al. |
| 2007/0156248 A1 | 7/2007 | Marco et al. | | 2008/0109072 A1 | 5/2008 | Girton |
| 2007/0160641 A1 | 7/2007 | Jang | | 2008/0113083 A1 | 5/2008 | Sutermeister et al. |
| 2007/0168016 A1 | 7/2007 | Gronemeyer et al. | | 2008/0124373 A1 | 5/2008 | Xiao et al. |
| 2007/0173923 A1 | 7/2007 | Savage et al. | | 2008/0131479 A1 | 6/2008 | Weber et al. |
| 2007/0178129 A1 | 8/2007 | Flanagan | | 2008/0140172 A1 | 6/2008 | Carpenter et al. |
| 2007/0181433 A1 | 8/2007 | Birdsall et al. | | 2008/0140186 A1 | 6/2008 | Grignani et al. |
| 2007/0184083 A1 | 8/2007 | Coughlin | | 2008/0145400 A1 | 6/2008 | Weber et al. |
| 2007/0190104 A1 | 8/2007 | Kamath et al. | | 2008/0147175 A1 | 6/2008 | Krivoruchko et al. |
| 2007/0191923 A1 | 8/2007 | Weber | | 2008/0147177 A1 | 6/2008 | Scheuermann et al. |
| 2007/0191928 A1 | 8/2007 | Rolando et al. | | 2008/0148002 A1 | 6/2008 | Fleming |
| 2007/0191931 A1 | 8/2007 | Weber | | 2008/0152929 A1 | 6/2008 | Zhao |
| 2007/0191943 A1 | 8/2007 | Shrivastava et al. | | 2008/0160166 A1 | 7/2008 | Rypacek et al. |
| 2007/0197980 A1 | 8/2007 | Barry et al. | | 2008/0160259 A1 | 7/2008 | Nielson et al. |
| 2007/0202466 A1 | 8/2007 | Schwarz et al. | | 2008/0161906 A1 | 7/2008 | Atanasoska et al. |
| 2007/0207186 A1 | 9/2007 | Scanlon et al. | | 2008/0171929 A1 | 7/2008 | Katims |
| 2007/0208412 A1 | 9/2007 | Elmaleh | | 2008/0175885 A1 | 7/2008 | Asgari |
| 2007/0219626 A1 | 9/2007 | Rolando et al. | | 2008/0177378 A1 | 7/2008 | Asgari |
| 2007/0224116 A1 | 9/2007 | Chandrasekaran et al. | | 2008/0183269 A2 | 7/2008 | Kaplan et al. |
| 2007/0224244 A1 | 9/2007 | Weber et al. | | 2008/0183277 A1 | 7/2008 | Atanasoska et al. |
| 2007/0225799 A1 | 9/2007 | Doty | | 2008/0183278 A1 | 7/2008 | Atanasoska et al. |
| 2007/0244541 A1 | 10/2007 | Schulman | | 2008/0188927 A1 | 8/2008 | Rohde et al. |
| 2007/0244569 A1 | 10/2007 | Weber et al. | | 2008/0195170 A1 | 8/2008 | Asgari |
| 2007/0250155 A1 | 10/2007 | Simpson | | 2008/0195189 A1 | 8/2008 | Asgari |
| 2007/0250156 A1 | 10/2007 | Palmaz | | 2008/0195198 A1 | 8/2008 | Asgari |
| 2007/0250158 A1 | 10/2007 | Krivoruchko et al. | | 2008/0208308 A1 | 8/2008 | Allen et al. |
| 2007/0255388 A1 | 11/2007 | Rudakov et al. | | 2008/0208313 A1 | 8/2008 | Yu et al. |
| 2007/0255392 A1 | 11/2007 | Johnson | | 2008/0208352 A1 | 8/2008 | Krivoruchko et al. |
| 2007/0264199 A1 | 11/2007 | Labhasetwar et al. | | 2008/0213377 A1 | 9/2008 | Bhatia et al. |
| 2007/0264303 A1 | 11/2007 | Atanasoska et al. | | 2008/0215129 A1 | 9/2008 | Venturelli et al. |
| 2007/0270940 A1 | 11/2007 | Doty | | 2008/0215139 A1 | 9/2008 | McMorrow et al. |
| 2007/0270942 A1 | 11/2007 | Thomas | | 2008/0215140 A1 | 9/2008 | Borck et al. |

| | | | | | | |
|---|---|---|---|---|---|---|
| 2008/0241218 A1 | 10/2008 | McMorrow et al. | 2009/0196899 A1 | 8/2009 | Birdsall et al. |
| 2008/0243113 A1 | 10/2008 | Shastri et al. | 2009/0198320 A1 | 8/2009 | Mueller et al. |
| 2008/0243230 A1 | 10/2008 | Lootz et al. | 2009/0202610 A1 | 8/2009 | Wilson |
| 2008/0243231 A1 | 10/2008 | Flanagan et al. | 2009/0204203 A1 | 8/2009 | Allen et al. |
| 2008/0243234 A1 | 10/2008 | Wilcox | 2009/0208428 A1 | 8/2009 | Hill et al. |
| 2008/0243240 A1 | 10/2008 | Doty et al. | 2009/0208555 A1 | 8/2009 | Kuttler et al. |
| 2008/0243242 A1 | 10/2008 | Kappelt et al. | 2009/0214373 A1 | 8/2009 | Stinson et al. |
| 2008/0249600 A1 | 10/2008 | Atanasoska et al. | 2009/0220612 A1 | 9/2009 | Perera |
| 2008/0249615 A1 | 10/2008 | Weber | 2009/0228037 A1 | 9/2009 | Rego |
| 2008/0255508 A1 | 10/2008 | Wang | 2009/0240323 A1 | 9/2009 | Wilcox |
| 2008/0255509 A1 | 10/2008 | Wang | 2009/0254171 A1 | 10/2009 | Heikkila |
| 2008/0262589 A1 | 10/2008 | Nagura | 2009/0259300 A1 | 10/2009 | Dorogy, Jr. et al. |
| 2008/0268308 A1 | 10/2008 | Schilling et al. | 2009/0270979 A1 | 10/2009 | Adden |
| 2008/0269872 A1 | 10/2008 | Lootz et al. | 2009/0274737 A1 | 11/2009 | Borck |
| 2008/0288048 A1 | 11/2008 | Rolando et al. | 2009/0281613 A1 | 11/2009 | Atanasoska et al. |
| 2008/0290467 A1 | 11/2008 | Shue | 2009/0287301 A1 | 11/2009 | Weber |
| 2008/0294236 A1 | 11/2008 | Anand et al. | 2009/0287302 A1 | 11/2009 | Thomas et al. |
| 2008/0294246 A1 | 11/2008 | Scheuermann | 2009/0306584 A1 | 12/2009 | Schmidtlein et al. |
| 2008/0306584 A1 | 12/2008 | Kramer-Brown | 2009/0306756 A1 | 12/2009 | Cho et al. |
| 2009/0005862 A1 | 1/2009 | Nakatani et al. | 2009/0306765 A1 | 12/2009 | Weber |
| 2009/0012599 A1 | 1/2009 | Broome et al. | 2009/0306766 A1 | 12/2009 | Mcdermott et al. |
| 2009/0018639 A1 | 1/2009 | Kuehling | 2009/0311300 A1 | 12/2009 | Wittchow |
| 2009/0018647 A1 | 1/2009 | Benco et al. | 2009/0312807 A1 | 12/2009 | Boudreault et al. |
| 2009/0018648 A1 | 1/2009 | Wittchow | 2009/0319035 A1 | 12/2009 | Terry |
| 2009/0022771 A1 | 1/2009 | Lynn et al. | 2009/0324684 A1 | 12/2009 | Atanasoska et al. |
| 2009/0024199 A1 | 1/2009 | Birdsall et al. | 2009/0326638 A1 | 12/2009 | Atanasoska et al. |
| 2009/0024209 A1 | 1/2009 | Ozdil et al. | 2010/0008970 A1 | 1/2010 | O'Brien et al. |
| 2009/0024210 A1 | 1/2009 | Klocke et al. | 2010/0010621 A1 | 1/2010 | Klocke |
| 2009/0024211 A1 | 1/2009 | Wittchow | 2010/0010640 A1 | 1/2010 | Gerold et al. |
| 2009/0028785 A1 | 1/2009 | Clarke | 2010/0015206 A1 | 1/2010 | Flanagan et al. |
| 2009/0030494 A1 | 1/2009 | Stefanadis et al. | 2010/0016940 A1 | 1/2010 | Shokoohi et al. |
| 2009/0030500 A1 | 1/2009 | Weber et al. | 2010/0021523 A1 | 1/2010 | Scheuermann et al. |
| 2009/0030504 A1 | 1/2009 | Weber et al. | 2010/0023112 A1 | 1/2010 | Borck et al. |
| 2009/0030506 A1 | 1/2009 | Klocke et al. | 2010/0023116 A1 | 1/2010 | Borck et al. |
| 2009/0030507 A1 | 1/2009 | Klocke et al. | 2010/0028436 A1 | 2/2010 | Ohrlander et al. |
| 2009/0035351 A1 | 2/2009 | Berglund et al. | 2010/0030326 A1 | 2/2010 | Radhakrishnan et al. |
| 2009/0043330 A1 | 2/2009 | To | 2010/0034899 A1 | 2/2010 | Harder et al. |
| 2009/0043374 A1 | 2/2009 | Nakano | 2010/0042205 A1 | 2/2010 | Atanasoska et al. |
| 2009/0043380 A1 | 2/2009 | Blaha et al. | 2010/0042206 A1 | 2/2010 | Yadav et al. |
| 2009/0048660 A1 | 2/2009 | Adden | 2010/0047312 A1 | 2/2010 | Wittchow |
| 2009/0062905 A1 | 3/2009 | Moore, Jr. et al. | 2010/0047324 A1 | 2/2010 | Fritz et al. |
| 2009/0069884 A1 | 3/2009 | Mueller | 2010/0049146 A1 | 2/2010 | Nielsen et al. |
| 2009/0076588 A1 | 3/2009 | Weber | 2010/0049296 A1 | 2/2010 | Sarasam et al. |
| 2009/0076596 A1 | 3/2009 | Adden et al. | 2010/0049299 A1 | 2/2010 | Popowski et al. |
| 2009/0081293 A1 | 3/2009 | Murase et al. | 2010/0049300 A1 | 2/2010 | Harder |
| 2009/0081450 A1 | 3/2009 | Ascher et al. | 2010/0055151 A1 | 3/2010 | Flanagan |
| 2009/0088831 A1 | 4/2009 | Goto | 2010/0057188 A1 | 3/2010 | Weber |
| 2009/0088834 A1 | 4/2009 | Wang | 2010/0057197 A1 | 3/2010 | Weber et al. |
| 2009/0093871 A1 | 4/2009 | Rea et al. | 2010/0070024 A1 | 3/2010 | Venturelli et al. |
| 2009/0095715 A1 | 4/2009 | Sabaria | 2010/0075162 A1 | 3/2010 | Yang et al. |
| 2009/0118809 A1 | 5/2009 | Scheuermann et al. | 2010/0076544 A1 | 3/2010 | Hoffmann et al. |
| 2009/0118812 A1 | 5/2009 | Kokate et al. | 2010/0076556 A1 | 3/2010 | Tomantschger et al. |
| 2009/0118813 A1 | 5/2009 | Scheuermann et al. | 2010/0081735 A1 | 4/2010 | Mao et al. |
| 2009/0118814 A1 | 5/2009 | Schoenle et al. | 2010/0082092 A1 | 4/2010 | Gerold |
| 2009/0118815 A1 | 5/2009 | Arcand et al. | 2010/0087910 A1 | 4/2010 | Weber |
| 2009/0118818 A1 | 5/2009 | Foss et al. | 2010/0087911 A1 | 4/2010 | Mueller |
| 2009/0118819 A1 | 5/2009 | Merz et al. | 2010/0087914 A1 | 4/2010 | Bayer et al. |
| 2009/0118820 A1 | 5/2009 | Gregorich et al. | 2010/0087915 A1 | 4/2010 | Bayer et al. |
| 2009/0118821 A1 | 5/2009 | Scheuermann et al. | 2010/0087916 A1 | 4/2010 | Bayer et al. |
| 2009/0118822 A1 | 5/2009 | Holman et al. | 2010/0092535 A1 | 4/2010 | Cook et al. |
| 2009/0118823 A1 | 5/2009 | Atanasoska et al. | 2010/0106243 A1 | 4/2010 | Wittchow |
| 2009/0123517 A1 | 5/2009 | Flanagan et al. | 2010/0119576 A1 | 5/2010 | Harder et al. |
| 2009/0123521 A1 | 5/2009 | Weber et al. | 2010/0119581 A1 | 5/2010 | Gratz et al. |
| 2009/0124956 A1 | 5/2009 | Swetlin et al. | 2010/0121432 A1 | 5/2010 | Klocke et al. |
| 2009/0131540 A1 | 5/2009 | Hiromoto et al. | 2010/0125325 A1 | 5/2010 | Allen et al. |
| 2009/0143855 A1 | 6/2009 | Weber et al. | 2010/0125328 A1 | 5/2010 | Flanagan |
| 2009/0149942 A1 | 6/2009 | Edelman et al. | 2010/0131050 A1 | 5/2010 | Zhao |
| 2009/0157165 A1 | 6/2009 | Miller et al. | 2010/0131052 A1 | 5/2010 | Kappelt et al. |
| 2009/0157172 A1 | 6/2009 | Kokate et al. | 2010/0161031 A1 | 6/2010 | Papirov et al. |
| 2009/0164002 A1 | 6/2009 | Becher et al. | 2010/0217370 A1 | 8/2010 | Scheuermann et al. |
| 2009/0171452 A1 | 7/2009 | Yamamoto et al. | | | |
| 2009/0177273 A1 | 7/2009 | Piveteau et al. | FOREIGN PATENT DOCUMENTS | | |
| 2009/0182290 A1 | 7/2009 | Harder et al. | | | |
| 2009/0182337 A1 | 7/2009 | Stopek et al. | AU | 2003 203 722 | 11/2003 |
| 2009/0182425 A1 | 7/2009 | Duda et al. | CA | 2 235 031 | 10/1998 |
| 2009/0192571 A1 | 7/2009 | Stett et al. | CA | 2 346 857 | 5/2000 |
| 2009/0192594 A1 | 7/2009 | Borck | CA | 2 371 800 | 8/2000 |
| 2009/0192595 A1 | 7/2009 | Nagura et al. | DE | 198 11 033 | 8/1999 |
| 2009/0192596 A1 | 7/2009 | Adden | DE | 198 11 033 C 1 | 8/1999 |
| | | | DE | 198 56 983 | 12/1999 |

| | | |
|---|---|---|
| DE | 103 57 281 | 7/2005 |
| DE | 103 61 941 | 7/2005 |
| DE | 10 2006 38236 | 2/2008 |
| EP | 0 006 544 | 6/1979 |
| EP | 0 337 035 | 10/1989 |
| EP | 0 337 035 | 11/1993 |
| EP | 0 923 389 | 7/1998 |
| EP | 0 923 912 | 6/1999 |
| EP | 0 966 979 | 12/1999 |
| EP | 0 972 563 | 1/2000 |
| EP | 1 054 644 | 11/2000 |
| EP | 1 071 490 | 1/2001 |
| EP | 1 222 901 | 7/2002 |
| EP | 1 260 214 | 11/2002 |
| EP | 1 270 023 | 1/2003 |
| EP | 1 273 314 | 1/2003 |
| EP | 1 370 306 | 12/2003 |
| EP | 0 923 912 | 2/2004 |
| EP | 1 389 471 | 2/2004 |
| EP | 1 393 766 | 3/2004 |
| EP | 1 419 793 | 5/2004 |
| EP | 0 951 877 | 6/2004 |
| EP | 1 260 214 | 6/2004 |
| EP | 0 875 218 | 2/2005 |
| EP | 1 389 471 | 8/2006 |
| EP | 1 733 746 | 12/2006 |
| EP | 1 752 167 | 2/2007 |
| EP | 1 465 552 | 5/2007 |
| EP | 1 835 042 | 9/2007 |
| EP | 1 750 780 | 10/2007 |
| EP | 1 562 565 | 3/2008 |
| EP | 1 642 551 | 12/2008 |
| EP | 1 653 885 | 4/2009 |
| EP | 1 632 256 | 9/2009 |
| EP | 1 703 858 | 10/2009 |
| EP | 2 139 535 | 1/2010 |
| EP | 1 883 380 | 3/2010 |
| EP | 2 189 169 | 5/2010 |
| RU | 2 218 242 | 12/2003 |
| RU | 2 218 242 C2 | 12/2003 |
| WO | WO 93/04118 | 3/1993 |
| WO | WO 97/11724 | 4/1997 |
| WO | WO 98/48851 | 11/1998 |
| WO | WO 99/47077 | 9/1999 |
| WO | 99/64580 | 12/1999 |
| WO | WO 99/64580 | 12/1999 |
| WO | WO 00/25841 | 5/2000 |
| WO | WO 00/48660 | 8/2000 |
| WO | WO 00/51136 | 8/2000 |
| WO | WO 00/66190 | 11/2000 |
| WO | WO 01/49338 | 7/2001 |
| WO | WO 01/78906 | 10/2001 |
| WO | WO 02/45764 | 6/2002 |
| WO | WO 02/47739 | 6/2002 |
| WO | WO 02/053202 | 7/2002 |
| WO | WO 03/002243 | 1/2003 |
| WO | WO 03/013396 A1 | 2/2003 |
| WO | WO 03/035131 | 5/2003 |
| WO | WO 03/035278 | 5/2003 |
| WO | WO 03/063733 | 8/2003 |
| WO | WO 03/094990 | 11/2003 |
| WO | WO 2004/093643 | 11/2004 |
| WO | WO 2005/065576 | 7/2005 |
| WO | 05/079335 | 9/2005 |
| WO | WO 2005/110395 | 11/2005 |
| WO | WO 2005/118019 | 12/2005 |
| WO | WO 2006/008739 | 1/2006 |
| WO | WO 2006/060033 | 6/2006 |
| WO | WO 2006/065356 | 6/2006 |
| WO | WO 2006/077154 | 7/2006 |
| WO | WO 2006/060534 A1 | 8/2006 |
| WO | WO 2006/108065 | 10/2006 |
| WO | WO 2007/005806 | 1/2007 |
| WO | WO 2007/013102 | 2/2007 |
| WO | WO 2007/018931 | 2/2007 |
| WO | WO 2007/024552 | 3/2007 |
| WO | WO 2007/035791 | 3/2007 |
| WO | WO 2007/079636 | 7/2007 |
| WO | WO 2007/082147 | 9/2007 |
| WO | 08/036457 | 3/2008 |
| WO | 08/036548 | 3/2008 |
| WO | 08/036554 | 3/2008 |
| WO | WO 2008/062414 | 5/2008 |
| WO | WO 2008/117315 | 10/2008 |
| WO | 09/045773 | 4/2009 |

OTHER PUBLICATIONS

Antipov et al., "Polyelectrolyte Multilayer Capsule Permeability Control," *Colloids and Surfaces A: Physiochem. Eng. Aspects*, 2002, 198-200, 535-541.

Antipov et al., "Polyelectrolyte Multilayer Capsules as Vehicles with Tunable Permeability," *Advances in Colloid and Interface Science*, 2004, 111:49-61.

Arts et al., "Polyphenols and disease risk in epidemiologic studies," *Am. J. Clin. Nutr.*, 2005, 81:317S-325S.

Artyukhin et al., "Layer-by-Layer Electrostatic Self-Assembly of Polyelectrolyte Nanoshells on Individual Carbon Nanotube Templates," *Langmuir*, 2004, 20:1442-1448.

Bach et al., "Corrosion, Protection and Repassivation After the Deformation of Magnesium Alloys Coated With a Protective Magnesium Fluoride Layer," *JOM*, 2004, p. 343.

Bakkar et al., "Improving corrosion resistance of magnesium-based alloys by surface modification with hydrogen by electrochemical ion reduction (EIR) and by plasma immersion ion implantation (PIII)," *Corrosion Science*, 2005, 47:1211-1225.

Baurschmidt et al., "The Electrochemical Aspects of the Thrombogenicity of a Material," *J. Bioengineering*, 1977, 1:261-278.

Berkland et al., "Controlling Surface Nano-structure Using Flow-Limited Field-Injection Electrostatic Spraying (FFESS) of poly(D,L-lactide-co-glycolide)," *Biomaterials*, 2004, 25:5649-5658.

Berry et al., "Functionalisation of magnetic nanoparticles for applications in biomedicine," *J. Phys. D: Appl. Phy.*, 2003, 36:R198-R206.

Bolz et al., "Effect of smooth, porous and fractal surface structure on the properties of an interface," *J. Materials Science: Materials in Medicine*, 1995, 6:844-848.

Brandau et al., "Nanoporous Ceramic Coatings for Synthesis of Radioactive Implants," *Journal of Nuclear Medicine Abstract Book*, Jun. 7, 2000, p. 244P, Abstract No. 1076.

Brückner et al., "Metal plasma immersion ion implantation and deposition (MPIIID): chromium on magnesium," *Surface and Coatings Technology*, 1998, 103-104, pp. 227-230.

Buescher et al., "Characterization of Wet-Chemically Nanostructured Stainless Steel Surfaces," *Mat. Res. Soc. Symp. Proc.*, 2001, 676:1-6.

Caruso et al., "Ultrathin Molybdenum Polyoxometalate-Polyelectrolyte Multilayer Films," *Langmuir*, 1998, 14:3462-3465.

Casan-Pastor et al., "Polyoxometalates: From Inorganic Chemistry to Materials Science," *Frontiers in Bioscience*, 2004, 9:1759-1770.

Chaieb et al., "Inhibition of the corrosion of steel in 1 M HC1 by eugenol derivatives," *Applied Surface Science*, 2005, 246:199-206.

Changwen et al., "Polyoxometalate-based organic-inorganic hybrid materials"; http://www.solgel.com/articles/oct01/changwen.asp, Retrieved from the Internet on Nov. 1, 2004 (17 pages).

Clemente-Leon et al., "Hybrid Langmuir-Blodgett Films Formed by Alternating Layers of Magnetic Polyoxometalate Clusters and Organic Donor Molecules—Towards the Preparation of Multifunctional Molecular Materials," *Adv. Mater.*, 2001, 13:574-577.

International Search Report/Written Opinion in PCT/US05/16600 mailed May 4, 2006, 15 pages.

International Preliminary Report on Patentability in PCT/US05/16600 mailed Nov. 30, 2006, 7 pages.

International Preliminary Report on Patentability in PCT/US07/78476 mailed Mar. 26, 2009, 7 pages.

International Search Report/Written Opinion in PCT/US07/66568 mailed Oct. 8, 2007, 11 pages.

International Preliminary Report on Patentability in PCT/US07/66568 mailed Oct. 23, 2008, 10 pages.

International Search Report/Written Opinion in PCT/US07/78505 mailed Mar. 4, 2008, 10 pages.

International Preliminary Report on Patentability in PCT/US07/78505 mailed Mar. 26, 2009, 7 pages.
Authorized Officer Athina Nickitas-Etienne, International Search Report/Written Opinion in PCT/US07/78449, mailed Jan. 13, 2009, 24 pages.
Authorized Officer Athina Nickitas-Etienne, International Preliminary Report on Patentability in PCT/US07/78449 mailed Mar. 26, 2009, 9 pages.
Authorized Officer Simin Baharlou, International Preliminary Report on Patentability in PCT/US07/75072 mailed Feb. 12, 2009, 9 pages.
International Search Report/Written Opinion in PCT/US07/78429 mailed Mar. 28, 2008, 13 pages.
International Preliminary Report on Patentability in PCT/US07/78429 mailed Apr. 2, 2009, 8 pages.
International Search Report/Written Opinion in PCT/US07/78411 mailed Mar. 6, 2008, 12 pages.
International Preliminary Report on Patentability in PCT/US07/78411 mailed Feb. 4, 2009, 8 pages.
Authorized Officer Elisabeth Reinecke, International Search Report/Written Opinion in PCT/US07/60137 mailed Jul. 27, 2007, 20 pages.
International Preliminary Report on Patentability in PCT/US07/78412 mailed Apr. 2, 2009, 7 pages.
Authorized Officer Trudy Hinterwimmer, International Search Report/Written Opinion in PCT/US07/78412 mailed Mar. 3, 2008, 10 pages.
Authorized Officer Joëlle Gerber, International Search Report/Written Opinion in PCT/US07/78450 mailed Nov. 19, 2008, 17 pages.
International Preliminary Report on Patentability in PCT/US07/78450 mailed Mar. 26, 2009, 7 pages.
International Search Report/Written Opinion in PCT/US07/73839 mailed Apr. 16, 2008, 17 pages.
International Preliminary Report on Patentability in PCT/US07/73839 mailed Apr. 2, 2009, 10 pages.
Authorized Officer Cecilia Giel-Barragan Ramos, International Search Report/Written Opinion in PCT/US07/79841 mailed Feb. 4, 2009, 21 pages.
Authorized Officer Athina Nickitas-Etienne, International Preliminary Report on Patentability in PCT/US07/79841 mailed Apr. 30, 2009, 7 pages.
Authorized Officer Joëlle Gerber, International Search Report/Written Opinion in PCT/US07/88888 mailed Jul. 13, 2009, 24 pages.
Authorized Officer Nora Lindner, International Preliminary Report on Patentability in PCT/US07/88888 mailed Jul. 30, 2009, 11 pages.
Authorized Officer Véronique van Loon-Mégard, International Search Report/Written Opinion in PCT/US08/75976 mailed Nov. 25, 2008, 20 pages.
Authorized Officer Trudy Hinterwimmer, International Search Report/Written Opinion in PCT/US09/49422 mailed Aug. 24, 2009, 10 pages.
Damiani et al., "Vasorelaxant effects on eugenol on rat thoracic aorta," *Vascular Pharmacol.*, 2003, 40:59-66.
Dexter, "Galvanic Corrosion," MAS Note, University of Delaware Sea Grant Marine Advisory Service, 2003.
Di Mario et al., "Moonlight: a controlled registry of an iridium-oxide coated stent with angiographic follow up," *Int. J. Cardiol.*, 2004, 95:329-331.
Dowling et al., "Anti-bacterial silver coatings exhibiting enhanced activity through the addition of Platinum," *Surf. & Coatings Tech.*, 2003, 163-164:637-640.
Duygu, "Controlled Release Systems," http://www.biomed.metu.edu.tr/courses/term_papers/contr-rel-svs_duvgu.htm (Dec. 30, 2005).
Eniola and Hammer, "Characterization of biodegradable drug delivery vehicles with the adhesive properties of leukocytes II: effect of degradation on targeting activity," *Biomaterials*, 2005, 26:661-670.
Farhat et al., "Corrosion Control Using Polyelectrolyte Multilayers," *Electrochemical and Solid State Letters*, 2002, 5(4):B13-B15.
Ferrando, "Review of Corrosion and Corrosion Control of Magnesium Alloys and Composites," *J. Mater. Eng.*,1989, 11:299-313.
Fischer et al., "Hydrogen in magnesium alloys and magnesium interfaces: preparation, electronic properties and interdiffusion," *J. Less Common Metals*, 1991, 172:808-815.

Fontenier et al., "Study of a 'Platinum-Magnesium' Cell to Supply Current to a Pacemaker," *Bioelectrochemistry and Bioenergetics*, 1975, 2(2):106-123.
Frei, "On the Role of Vitamin C and Other Antioxidants in Atherogenesis and Vascular Dysfunction," *Proceedings—Society for Experimental Biology and Medicine*, 1999, 222:196-204.
Gomes et al., "Alternative tissue engineering scaffolds based on starch: processing methodologies, morphology, degradation and mechanical properties," *Materials Science and Engineering C*, 2002, 20:19-26.
Grassi et al., "Short-term administration of dark chocolate is followed by a significant increase in insulin sensitivity and a decrease in blood pressure in healthy persons," *Am. J. Clin. Nutr.*, 2005, 81(3):611-614.
Gray and Luan, "Protective coatings on magnesium and its alloys—a critical review," *J. Alloys Compounds*, 2002, 336:88-113.
Guo et al., "Multi-layer LB films of single-wall carbon nanotubes," *Physica B*, 2002, 323:235-236.
Guo et al., "Manipulation of single-wall carbon nanotubes into aligned molecular layers," *Chem. Phys. Lett.*, 2002, 362:314-318.
Gurib-Fakim, "Medicinal plants: Traditions of yesterday and drugs of tomorrow," *Molecular Aspects of Medicine*, 2006, 27:1-93.
Haferkamp et al., "Magnesium-Base-Alloys as Implant-Material Steps to the Production of Thin Components," *Magnesium*, 2000, 159-164.
Hau et al., "Surface-Chemistry Technology for Microfluidics," *J. Micromech. Microeng.*, 2003, 13:272-278.
Huang et al., "A Review on Polymer Nanofibers by Electro-spinning and their Applications in Nanocomposites," *Composites Science & Technology*, 2003, 63:2223-2253.
Heublein et al., "Biocorrosion of magnesium alloys: a new principle in cardiovascular implant technology?" *Heart*, 2003, 89:651-656.
Heublein et al., "Bio-corrosion—a new principle for temporary cardiovascular implants?" *European Heart Journal, Journal of the European Society of Cardiology*, 2000, vol. 21, p. 286, Abstract No. P1605.
Heublein et al., "Degradation of Metallic Alloys—A New Principle in Stent Technology?" *The American Journal of Cardiology, Eleventh Annual Symposium Transcatheter Cardiovascular Therapeutics Abstracts*, Sep. 22, 1999.
Heublein et al., "Local Tissue Engineering by Biocorrosion Vision or Reality?" *The American Journal of Cardiology, TCT Abstracts/Poster*, Oct. 16, 2000.
Ito et al., "Antioxidant action of eugenol compounds; role of metal ion in the inhibition of lipid peroxidation," *Food Chem. Toxicol.*, 2005, 43:461-466.
Ivanova and Ivanov, "Mechanisms of the extracellular antioxidant defend," *Experimental Pathology and Parasitology*, 2000, 4:49-59.
Jiang, "A review of wet impregnation—An alternative method for the fabrication of high performance and nano-structured electrodes of solid oxide fuel cells," *Materials Science and Engineering A*, 2006, 418:199-210.
Kean and Davies, "Cathodic Protection," 7 pages, 1981; http://www.npl.co.uk/upload/pdf/cathodic_protection.pdf.
Kim et al., "Comprehensive study on vitamin C equivalent antioxidant capacity (VCEAC) of various polyphenols in scavenging a free radical and its structural relationship," *Crit. Rev. Food Sci. Nutr.*, 2004, 44(4):253-273.
Kim et al., "Effect of Anti-Oxidant (Carvedilol and Probucol) Loaded Stents in a Porcine Coronary Restenosis Model," *Circ. J.*, 2005, 69:101-106.
Kong et al., "Polyelectrolyte-functionalized multiwalled carbon nanotubes: preparation, characterization and layer-by-layer self assembly," *Polymer*, 2005, 46:2472-2485.
Kumar et al., "Polyanhydrides: an overview," *Advanced Drug Delivery Reviews*, 2002, 54:889-910.
Kurth et al., "Multilayer on Solid Planar Substrates: From Structure to Function", *Multi-layer Thin Films Sequential Assembly of Nanocomposite Materials*, 2003, Chapter 14, pp. 393-426.
Kurth et al., "Ultrathin Composite Films Incorporating the Nanoporous Isopolyoxomolybdate 'Keplerate' $(NH_4)_{42}[Mo_{132}O_{372}(CH_3COO)_{30}(H_2O)_{72}]$," *Chem. Mater.*, 2000, 12:2829-2831.

Kutsenko et al., "Structural Changes in Mg Alloy induced by plasma immersion ion implantation of Ag," *Acta Materialia*, 2004, 52:4329-4335.

Lambert et al., "Inhibition of carcinogenesis by polyphenols: evidence from laboratory investigations," *Am. J. Clin. Nutr.*, 2005, 81:284S-291S.

Lee et al., "Retentive and compressive strengths of modified zinc oxide-eugenol cements," *J. Dentistry*, 2000,28:69-75.

Liao et al., "Fabrication of porous biodegradable polymer scaffolds using a solvent merging/particulate leaching method," *J. Biomed. Mater. Res.*, 2002, 59(4):676-681.

Lin et al., "Micropatterning proteins and cells on polylactic acid and poly(lactide-co-glycolide)," *Biomaterials*, 2005, 26:3655-3662.

Liu et al., "Sol-gel deposited TiO2 film on NiTi surgical alloy for biocompatibility improvement," *Thin Solid Films*, 2003, 429:225-230.

Liu, *Introduction to Corrosion and Protection*, Corrosion and Protection Centre, School of Materials, The University of Manchester, 2006, 36 pages.

Liu et al., "Layer-By-Layer Ionic Self-Assembly of Au Colloids Into Multilayer Thin-Films with Bulk Metal Conductivity," *Chemical Physics Letters*, 1998, 298:315-319.

Liu et al., "Functional Polyoxometalate Thin Films via Electrostatic Layer-by-Layer Self-Assembly," *Journal of Cluster Science*, 2003, 14:405-419.

Maier et al., "High concentrations of magnesium modulate vascular endothelial cell behaviour in vitro," *Biochim. Biophys. Acta*, 2004, 1689:6-12.

Mamedov et al., "Molecular Design of Strong Single-Wall Carbon Nanotube/Polyelectrolyte Multilayer Composites," *Nature Materials*, 2002, 1:190-194.

Matsuoka et al., "Hyperthermia Using Magnetite Cationic Liposomes for Hamster Osteosarcoma," *BioMagnetic Research and Technology*, 2004, 2:3-8.

Medical Device Daily, "Conor Cites Positive 12-month Results for Its CoStar Stent", May 2005 (1 page).

Middleton and Tipton, "Synthetic Biodegradable Polymers as Medical Devices," http://www.devicelink.com/mpb/archive/98/03/002.html, Mar. 1998, 9 pages.

Mihailovic et al., "Unusual Magnetic State in Lithium-Doped $MoS_2$ Nanotubes," *Phys. Rev. Lett.*, 2003, 90 146401-1-4.

Mikos and Temenoff, "Formation of highly porous biodegradable scaffolds for tissue engineering," *Electronic Journal of Biotechnology*, 2000, 3(2):1-6.

Mohanty et al., "Effect of *Curcuma longa* and *Ocimum sanctum* on myocardial apoptosis in experimentally induced myocardial ischemic-reperfusion injury," *BMC Complementary and Alternative Medicine*, 2006, 6:3-14.

Mohanty et al. "Evaluation of soft tissue response to a poly[urethane urea]," *Biomaterials*, 1992, 13(10):651-656.

Molnar and Garai, "Plant-derived anti-inflammatory compounds affect MIF tautomerase activity," *International Immunopharmacology*, 2005, 5:849-856.

Moskaug et al., "Polyphenols and glutathione synthesis regulation," *Am. J. Clin. Nut.*, 2005, 81:277S-283S.

Naderi et al., "Effect of some volatile oils on the affinity of intact and oxidized low-density lipoproteins for adrenal cell surface receptors," *Mol. Cell. Biochem.*, 2004, 267:59-66.

Niemeyer et al., "Magnesium alloys as biodegradable metallic implant materials for cardiovascularic and orthopaedic surgery," *Euromat 2001, 7th European Conference on Advanced Materials and Processes*, Jun. 10-14, 2001 (Abstract).

Nilsson et al., "Development of a dosage method for electrochemical treatment of tumours: a simplified mathematical model," *Bioelectrochemistry and Bioenergetics*, 1998, 47:11-18.

Ou et al., "Protective effects of eugenol against oxidized LDL-induced cytotoxicity and adhesion molecule expression in endothelial cells," *Food Chem. Toxicol.*, 2006, 44:1485-1495.

Park et al., "Microstructural change and precipitation hardening in melt-spun Mg-X-Ca alloys," *Science and Technology of Advanced Materials*, 2001, 2:73-78.

Peuster et al., "Long-term biocompatibility of a corrodible peripheral iron stent in the porcine of descending aorta," *Biomaterials*, 2006, 27:4955-4962.

Peuster et al., "A novel approach to temporary stenting: degradable cardiovascular stents produced from corrodible metal-results 6-18 months after implantation into New Zealand white rabbits," *Heart*, 2001, 86(5).

Prasse et al., "Electric Anisotropy of Carbon Nanofibre/Epoxy Resin Composites Due to Electric Field Induced Alignment," *Composites Science and Technology*, 2003, 63:1835-1841.

Ratnam et al., "Role of antioxidants in prophylaxis and therapy: A pharmaceutical perspective," *J. Controlled Release*, 2006, 113:189-207.

Remskar et al., "Self-Assembly of Subnanometer-Diameter Single-Wall $MoS_2$ Nanotubes," *Science*, 2001, 292:479-481.

Rezwan et al., "Biodegradable and bio active porous polymer/inorganic composite scaffolds for bone tissue engineering," *Biomaterials*, 2006, 27:3413-3431.

Rhule et al., "Polyoxometalates in Medicine," *Chem. Rev.*, 1998, 98:327-357.

Rutledge et al., "Electrostatic Spinning and Properties of Ultrafine Fibers," *National Textile Center Annual Report*, Nov. 2001, M01-D22, pp. 1-10.

Ryan et al., "Fabrication methods of porous metals for use in orthopaedic applications," *Biomaterials*, 2006, 27:2651-2670.

Sastry et al., "DNA-Mediated Electrostatic Assembly of Gold Nanoparticles into Linear Arrays by a Simple Drop-Coating Procedure," *Appl. Phys. Lett.*, 2001, 78:2943-2945.

Satoh et al., "Effect of Antioxidants on Radical Intensity and Cytotoxic Activity of Eugenol," *Anticancer Res.*, 1998, 18:1549-1552.

Sawitowski et al., "Nanoporous Alumina Coatings for Medical Implants and Stents—Radiotherapy, Drug Delivery, Biological Compatibility," *Materials Research Society Symposium Proceedings*, 1999, 581:523-528.

Sawitowski, "New Drug Delivery Systems—Examples of Applied Nanotechnology," *VDE World Microtechnologies Congress*, Sep. 25-27, 2000, Expo 2000, Hannover, Germany, Proveeds vol. 1, p. 343-346.

Sawyer et al., "Electrochemical Criteria in the Choice of Materials used in Vascular Prostheses," *Biophysical Mechanisms in Vascular Homeostasis and Intravascular Thrombosis*, 1965, pp. 337-348.

Schetky, "Shape Memory Alloys," *Encyclopedia of Chemical Technology* (3rd ed.), 1962, John Wiley & Sons, 20:726.

Shaw, "Corrosion Resistance of Magnesium Alloys," *ASM Handbook vol. 13A: Corrosion: Fundamentals, Testing, and Protection*, 2003, 5 pages.

Shenoy et al., "Role of Chain Entanglements on Fiber Formation During Electrospinning of Polymer Solutions: Good Solvent, Non-Specific Polymer-polymer Interaction Limit," *Polymer*, 2005, 46:3372-3384.

Shi et al., "A novel electrically conductive and biodegradable composite made of polypyrrole nanoparticles and polylactide," *Biomaterials*, 2004, 25:2477-2488.

Shin, "Experimental Characterization of Electrospinning: the Electrically Forced Jet and Instabilities," *Polymer*, 2001, 42:9955-9967.

Singh et al., "Electrocatalytic Activity of Electrodeposited Composite Films of Polypyrrole and $CoFe_2O_4$ Nanoparticles Towards Oxygen Reduction Reaction," *Electrochimica Acta*, 2004, 49:4605-4612.

Song et al., "Galvanic corrosion of magnesium alloy AZ91D in contact with an aluminium alloy, steel and zinc," *Corrosion Science*, 2004, 46:955-977.

Stoclet et al., "Vascular protection by dietary polyphenols," *Eur. J. Pharmacol.*, 2004, 500:299-313.

Straumal et al., "Vacuum arc deposition of protective layers on glass and polymer," *Thin Solid Films*, 2001, 383:224-226.

Suhaj, "Spice antioxidants isolation and their antiradical activity: a review," *J. Food Composition and Analysis*, 2006, 19:531-537.

Sukhorukov et al., "Comparative Analysis of Hollow and Filled Polyelectrolyte Microcapsules Templated on Melamine Formaldehyde and Carbonate Cores," *Macromol. Chem. Phys.*, 2004, 205:530-535.

Suslick et al., "The Photochemistry of Chromium, Manganese, and Iron Porphyrin Complexes," *J. Chem.*, 1992, 16:633-642.

Tada et al., "Distribution of pH during galvanic corrosion of a Zn/steel couple," Electrochimica Acta, 2004, 49:1019-1026.

Tan et al., "Systematic Parameter Study for Ultra-Fine Fiber Fabrication Via Electrospinning Process," *Polymer*, 2005, 46:6128-6134.

Tian et al., "Corrosion resistance improvement of magnesium alloy using nitrogen plasma ion implantation," *Surface & Coatings Technology*, 2005, 198:454-458.

Vermette et al., "Immobilized Liposome Layers for Drug Delivery Applications," *J. Controlled Release*, 2002, 80:179-195.

von Euler et al., "Cell proliferation and apoptosis in rat mammary cancer after electrochemical treatment (EChT)," *Bioelectrochemistry*, 2004, 62:57-65.

Vrbanic et al., "Air-Stable Monodispersed $Mo_6S_3I6$ Nanowires,"*Nanotechnology*, 2004, 15:635-638.

Wallerath et al., "A blend of polyphenols explains the stimulatory effect of red wine on human endothelial NO synthase," *Nitric Oxide*, 2005, 12(2):97-104.

Wan et al., "Influence of Plasma Immersion Ion Implantation on Corrosion Properties of Magnesium," South Jiaotong University, Chengdu, 2005.

Wang et al., "Nonlinear optical properties of thin iron films grown on MgO (100) by pulsed laser deposition," *Thin Solid Films*, 2005, 471:86-90.

Wang et al., "Characterisation of Severely Deformed Austenitic Stainless Steel Wire," *Materials Science and Technology*, 2005, 21:1323-1328.

Wang, "Recent development of non-platinum catalysts for oxygen reduction reaction," *J. Power Sources*, 2005, 152:1-15.

Weber et al., "Hardness and corrosion resistance of single-phase nitride and carbide on ion," *Materials Science and Engineering*, 1995, 99:205-210.

Weh et al., "Evolution of a fractal-like surface structures in layers of polyacrylonitrile solutions by interfacial dynamic processes," *J. Colloid and Interface Science*, 2004, 271:407-415.

Widmer et al., "Manufacture of porous biodegradable polymer conduits by an extrusion process for guided tissue regeneration," *Biomaterials*, 1998, 19:1945-1955.

Wieneke et al., "Stent Coating: A New Approach in Interventional Cardiology," *Herz*, 2002, 27(6):518-526.

Williamson et al., "Bioavailability and bioefficacy of polyphenols in humans. II. Review of 93 intervention studies," *Am. J. Clin. Nutr.*, 2005, 81:243S-255S.

Witte et al., "In vitro and in vivo corrosion measurements of magnesium alloys," *Biomaterials*, 2006, 27:1013-1018.

Yamaguchi et al., "Mg2Si Coating Technology on Magnesium Alloys to Improve Corrosion and Wear Resistance", *JOM*, 2004, p. 343.

Yi et al., "Characterization of a bioactive nanotextured surface created by controlled chemical oxidation of titanium," *Surface Science*, 2006, 600:4613-4621.

You et al., "The Effect of Calcium Additions on the Oxidation Behavior in Magnesium Alloys," *Scripta Mat.*, 2000, 42:1089-1094.

Yu and Uan, "Sacrificial Mg film anode for cathodic protection of die cast Mg-9-wt.%-1 wt.%Zn alloy in NaCl aqueous solution," *Scripta Mat.*, 2006, 54:1253-1257.

Yue et al., "Improvement in the Corrosion Resistance of Magnesium ZK60/SiC Composite by Excimer Laser Surface Treatment," *Scripta Materialia*, 1998, 38(2):191-198.

Zeta Potential-An Introduction in 30 Minutes, Technical Note; http://www.nbtc.cornell.edu/facilities/downloads/Zeta%20potential%20-%20An%20introduction%20in%2030%20minutes.pdf, Retrieved from the Internet on May 9, 2005 (6 pages).

Zhang et al., "Natural Polyelectrolyte Films Based on Layer-by-Layer Deposition of Collagen and Hyaluronic Acid," *Biomaterials*, 2005, 26:3353-3361.

Zhang et al., "Improving multilayer films endurance by photoinduced interaction between Dawson-type polyoxometalate and diazo resin," *Materials Chemistry and Physics*, 2005, 90:57-52.

Zhang et al., "Ways for fabricating stable layer-by layer self-assemblies: combined ionic self-assembly and post chemical reaction," *Colloids and Surfaces A: physiochemical and Engineering Aspects*, 2002, pp. 198-200, 439-442.

Zhou et al., "Drug-loaded, Magnetic, hollow silica nanocomposites for nanomedicine," *Nanomedicine: Nanotechnology, Biology and Medicine*, 2005, 1:233-237.

Zucchi et al., "Influence of a silane treatment on the corrosion resistance of a WE43 magnesium alloy," *Surface Coatings Technol.*, 2006, 200:4136-4143.

International Search Report and Written Opinion mailed Jan. 25, 2008 from International Application No. PCT/US2007/075072.

Aaltonen, "Atomic Layer Deposition of Noble Metal Thin Films," *University of Helsinki*, Apr. 8, 2005, pp. 1-71.

Albion Research Notes, Newsletter, Oct. 1994, 3(4): 1-4.

Anand et al., "Ion-exchange resins: carrying drug delivery forward," *DDT*, 2001, 6: 905-914.

Anderson et al., "A new conductive polymer as a replacement for chrome conversion coatings," *Aerospace Coatings Removel and Coatings Conference*, May 20-22, 2003, Colorado Springs, CO, 7pages.

Antipov et al., "Polyelectrolyte Multilayer Capsules as Vehicles with Tunable Permeability", *Advances in Colloid and Interface Science*, 2004, 111: 49-61.

Arts et al., "Polyphenols and disease risk in epidemiologic studies," *Am. J. Clin. Nutr.*, 2005, 81:317S-325S.

Artyukhin et al., "Layer-by-Layer Electrostatic Self-Assembly of Polyelectrolyte Nanoshells on Individual Carbon Nanotube Templates," *Langmuir*, 20:1442-1448.

Ashtari et al. "An efficient method for recovery of target ssDNA based on amino-modified silica-coated magnetic nanoparticles" *Talanta 67*. (2005). 548-554.

Atta, "Electrochemical synthesis, characterization and some properties of a polymer derived from thioflavin S.," *European Polymer Journal*, 2005, 41: 3018-3025.

Australian Government, Department of Health and Aging, "Horizon Scanning Technology Prioritising Summary-Biodegradable stents for coronary artery disease," *Australia and New Zealand Horizon Scanning Network (ANZHSN)*, Aug. 2007, pp. 1-13.

Authorized Officer Athina Nickitas-Etienne, International Preliminary Report on Patentability in PCT/US07/78449 mailed Mar. 26, 2009, 9 pages.

Authorized Officer Athina Nickitas-Etienne, International Preliminary Report on Patentability in PCT/US07/79841 mailed Apr. 30, 2009, 7 pages.

Authorized officer Athina Nickitas-Etienne, International Preliminary Report on Patentability in PCT/US08/86639 mailed Jun. 24, 2010, 2 pages.

Authorized Officer Cecilia Giel-Barragan Ramos, International Search Report/Written in PCT/US07/79841 mailed Feb. 4, 2009, 11 pages.

Authorized Officer Elisabeth Reinecke, International Search Report/Written Opinion in PCT/US07/60137 mailed Jul. 27, 2007, 20 pages (656W01).

Authorized Officer Joëlle Gerber, International Search Report/Written Opinion in PCT/US07/78450 mailed Nov. 19, 2008, 17 pages.

Authorized Officer Joëlle Gerber, International Search Report/Written Opinion in PCT/US07/88888 mailed 13 Jul. 2009, 24 pages.

Authorized Officer Nora Lindner, International Preliminary Report on Patentability in PCT/US07/88888 mailed Jul. 30, 2009, 11 pages.

Authorized Officer Simin Baharlou, International Preliminary Report on Patentability in PCT/US07/66568 mailed Oct. 23, 2008, 10 pages.

Authorized Officer Simin Baharlou, International Preliminary Report on Patentability in PCT/US07/75072 mailed Feb. 12, 2009, 9 pages.

Authorized Officer Trudy Hinterwimmer, International Search Report/Written Opinion in PCT/US07/78412 mailed Mar. 3, 2008, 10 pages.

Authorized Officer Trudy Hinterwimmer, International Search Report/Written Opinion in PCT/US09/49422 mailed Aug. 24, 2009, 10 pages.

Authorized Officer Véronique van Loon-Megard, International Search Report/Written Opinion in PCT/US08/75976 mailed Nov. 25, 2008 20 pages.

International Search Report/Written Opinion in PCT/US2009/43326 mailed Aug. 6, 2009, 9 pages.

Babapulle and Eisenberg, "Coatred stents for their prevention of restenosis: Part II," *Circulation*, 2021, 106: 2849-2866 Nov. 26, 2002.

Bach et al., "Corrosion, Protection and Repassivation After the Deformation of Magnesium Alloys Coated With a Protective Magnesium Fluoride Layer," *JOM*, 2004, p. 343.

Bakkar et al., "Improving corrosion resistance of magnesium-based alloys by surface modification with hydrogen by electrochemical ion reduction (EIR) and by plasma immersion ion implantation (PIII)," *Corrosion Science*, 2005, 47:1211-1225.

Balasubramanian et al. "Dispersion and Stability Studies of Resorcinarene-Encapsulated Gold Nanoparticles." *Langmuir*, 2002, 1676-3681.

Bao, Y. et al. "Preparation of functionalized and gold-coated cobalt nanocrystals for biomedical applications." *Journal of Magnetism and Magnetic Materials*, 2005, 293:15-19.

Baurschmidt et al., "The Electrochemical Aspects of the Thrombogenicity of a Material," *J. Bioengineering*, 1977, 1:261-278.

Bekesi et al., "Efficient Submircon Processing of Metals with Femto," *Appl. Phys. A.*, Published Oct. 25, 2002, pp. 355-357.

Ben-Hamu et al., "Influence of Si, Ca and Ag addition on corrosion behaviour of new wrought Mg-Zn alloys," *Materials Science and Technology*, 2006, vol. 22, No. 10, pp. 1213-1218.

Bereket et al., "Electrochemical synthesis and anti-corrosive properties of polyaniline, poly(2-anisidine), and poly(aniline-so-2-anisidine) films on stainless steel," *Progress in Organic Coatings*, 2005, 54: 63-72.

Berkland et al., "Controlling Surface Nano-structure Using Flow-Limited Field-Injection Electrostatic Spraying (FFESS) of poly(D,L-lactide-*co*-glycolide)," *Biomaterials*, 2004, 25:5649-5658.

Bernkop-Schnurch, "Chitosan and its derivatives: potential excipients for peroral peptide delivery systems," *International J. Of Pharmaceutics*, 2000, 194: 1-13.

Berry et al., "Functionalisation of magnetic nanoparticles for applications in biomedicine," *J. Phys. D: Appl. Phys.*, 2003, 36:R198-R206.

Biercuk et al., "Low-temperature atomic-layer-deposition lift-off method for microelectronic and nanoelectronic applications," *Applied Physics Letters*, vol. 83, No. 12, Sep. 22, 2003, pp. 2405-2407.

Blanusa et al., "Chelators as Antidotes of Metal Toxicity Therapeutic and Experimental Aspects," *Current Medicinal Chemistry*, 2005, vol. 12, pp. 2771-2794.

Bolz et al., "Effect of smooth, porous and fractal surface structure on the properties of an interface," *J. Materials Science: Materials in Medicine*, 1995, 844-848.

Bosiers et al., "Absorbable Metal stent for CLI in Infrapopliteal lesions: 1 year results," *CX 2005 Global Endovascular Forum*, Apr. 2005, pp. 1-23.

Brandau et al., "Nanoporous Ceramic Coatings for Synthesis of Radioactive Implants," *Journal of Nuclear Medicine Abstract Book*, Jun. 7, 2000, p. 244P, Abstract No. 1076.

Brückner et al., "Metal plasma immersion ion implantation and deposition (MPIIID): chromium on magnesium," *Surface and Coatings Technology*, 1998, 103-104, pp. 227-230.

Brunatto and Muzart, "Influence of the gas mixture flow on the processing parameters of hollow cathode discharge ion sintering," *J. Phys. D.: Appl. Phys.*, 2007, 40: 3937-3944.

Brunner et al., "Porosity Tailored Growth of Black Anodic Layers on Magnesium in an Organic Electrolyte," *Journal of the Electrochemical Society*, vol. 156 (2), Dec. 12, 2008, pp.C62-C66.

Buescher et al., "Characterization of Wet-Chemically Nanostructured Stainless Steel Surfaces," *Mat. Res. Soc. Symp. Proc.*, 2001, 676:1-6.

Caruso et al., "Ultrathin Molybdenum Polyoxometalate-Polyelectrolyte Multilayer Films," *Langmuir*, 1998, 14:3462-3465.

Casan-Pastor et al., "Polyoxometalates: From Inorganic Chemistry to Materials Science," *Frontiers in Bioscience*, 2004, 9:1759-1770.

Chaieb et al , "Inhibition of the corrosion of steel in 1 M HC1 by eugenol derivatives," *Applied.Surface Science*, 2005, 246:199-206

Chang et al., "Effect of Heat Treatment on Corrosion and Electrochemical behavior of Mg-3Nd-0.2Zn-0.4Zr (wt. %) alloy," *Science Direct, Electrochimica Acta 52*, 2007, 3160-3167.

Chang et al., "Templated sythesis of Gold-iron Alloy nanoparticles using pulsed laser deposition," *Nanotechnology*, vol. 17, 2006, pp. 5131-5135.

Changwen et al., "Polyoxometalate-based organic-inorganic hybrid materials," 2004, *Sol-Gel*, pg. 1.

Chen et al., "Laser Cladding of Mg20A18o Powder on ZM5 Magnesium Alloy," *Corrosion.Engineering, Science and Technology*, 2007, vol. 42, No. 2, pp. 130-136.

Cheng et al., "Electrogeneration and electrochemical properties of hybrid materials: polypyrrole doped with polyoxometalates $PW_{12-x}Mo_xO_{40}^{3-}$(x=0,3,6,12)," *Synthetic Metals*, 2002, 129: 53-59.

Cho et al., "Gold-coated iron nanoparticles: a novel magnetic resonance agent for $T_1$ and $T_2$ weighted imaging," *Nanotechnology*, vol. 17, 2006, pp. 640-644.

Chou et al., "Electrochemical treatment of mouse and rat fibrosarcomas with direct current," *Bioelectromagnetics*, 1997, 18:14-24.

Clemente-Leon et al., "Hybrid Langmuir-Blodgett Films Formed by Alternating Layers of Magnetic Polyoxometalate Clusters and Organic Donor Molecules — Towards the Preparation of Multifunctional Molecular Materials," *Adv. Mater.*, 2001, 13:574-577.

Cogger et al. "An Introduction to Electrochemical Impedance Measurement," *Solartron Analytical*, 1999, 2-14.

Conolly et al., "X-Ray microtomography studies of localized corrosion and transitions to stress corrosion cracking," *Materials Science and Technology*, 2006, vol. 22, No. 9, pp. 1076-1085.

Costa et al., "The effect of the magnetic field on the corrosion behavior of Nd-Fe-B permanent magnets." *Journal of Magnetism and Magnetic Materials*, 278, 2004, pp. 348-358.

Damen et al., "Paclitaxel esters of malic acid as prodrugs with improved water solubility," *Bioorganic & Medicinal Chemistry*, 2000, 8: 427-432.

Damiani et al., "Vasorelaxant effects on eugenol on rat thoracic aorta," *Vascular Pharmacol.*, 2003,.40:59-66.

Davies, "Changing the salt, changing the drug," *The Pharmaceutical Journal*, 2001, 266: 322-323.

De Geest et al., "Self-rupturing Microcapsules," *Adv. Mater.*, 2005, vol. 17, pp. 2357-2361.

de Witte, "Analysis of the principal component of external casing corrosion in deep wells," *J. Appl. Electrochem.*, 1985, 15: 325-334.

Dexter, "Galvanic Corrosion," MAS Note, University of Delaware Sea Grant Marine Advisory Service, 2003.

Di Mario et al., "Drug-eluting bioabsorbable magnesium stent," *J. Interventional Cardiol.*, 2004,.17(6): 391-395.

Di Mario et al., "Moonlight: a controlled registry of an iridium oxide-coated stent with angiographic follow-up," *Int. J. Cardiol.*, 2004, 95:329-331.

Dowling et al., "Anti-bacterial silver coatings exhibiting enhanced activity through the addition of Platinum," *Surf. & Coatings Tech.*, 2003, 163-164:637-640.

Duncan et al., "Polymer-drug conjugates, PDEPY and PELT: basic principles for design and transfer from the laboratory to clinic," *Journal of Controlled Release*, 2001, 74: 135-146.

Eggebrecht et al., "Novel Magnetic Resonance-Compatible Coronary Stent: The Absorbable Magnesium-Alloy Stent," *Circulation*, 2005, 112: 303-304.

Eniola et al., "Characterization of Biodegradable Drug Delivery Vehicles with the Adhesive Properties of Leukocytes II: Effect of Degradation on Targeting Activity," *Biomaterials*, 26:661-670 2005.

Erbel et al., "Absorbierbare Stents-Eine Vielversprechende Neuerung?" *Urban & Vogel*, No. 4,.2007, pp. 308-319.

Erbel et al., "Temporary scaffolding of coronary arteries with bioabsorbable magnesium stents: a prospective, non-randomised multicentre trial," *Lancet*, 2007, vol. 369, pp. 1869-75.

Erne et al., "The Road to Bioabsorbable Stents: Reaching Clinical Reality?" *Cardio Vascular and Interventional Radiology*, Sep. 26, 2005, pp. 11-16.

European Examiner Marie-France Weiss, International Preliminary report on Patentability received in PCT/US2007/078417, mailed Mar. 26, 2009, 8 pages.

European Examiner Melanie Geuer, International Preliminary Report on Patentability, received in PCT/US2007/078407, mailed Mar. 26, 2009, 6 pages.
European Search Report from EP 10159664.1, mailed Jun. 4, 2010, 3 pages.
Examiner Beate Giffo-Schmitt, International Preliminary Report on Patentability in PCT/US05/16600 mailed Nov. 30, 2006, 7 pages.
Examiner John De Bruijn, International Search Report/Written Opinion in PCT/US05/16600 mailed May 4, 2006, 15 pages.
Examiner M. Sierra Gonzalez, International Preliminary Report on Patentability in PCT/US07/78476 mailed Mar. 6, 2009, 7 pages.
Examiner Melanie Geuer, International Preliminary Report on Patentability in PCT/US07/78411 mailed Feb. 4, 2009, 8 pages.
Examiner Melanie Geuer, International Preliminary Report on Patentability in PCT/US07/78412 mailed Apr. 2, 2009, 7 pages.
Examiner Melanie Geuer, International Preliminary Report on Patentability in PCT/US07/78505 mailed Mar. 26, 2009, 7 pages.
Examiner Sierra Gonzalez, International Preliminary Report on Patentability in PCT/US07/78450 mailed Mar. 26, 2009, 7 pages.
Falotico, "Cordis Fully Bioabsorbable Stent Program," *Euro PCR09*, May 22, 2009, pp. 1-21.
Fan et al., "Influence of Lanthanum on the microstructure, mechanical property and corrosion resistance of magnesium alloy," *J. Mater Sci*, 2006, vol. 41, pp. 5409-5416.
Fan et al., "Metallic Stents Coated with Bioabsorable Polymers," *Cardiac Interventions Today*, Jun./Jul. 2009, pp. 42-49.
Feng et al., "Sonochemical preparation of photochromic nanocomposite thin film based on polyoxometalates well dispersed in polyacrylamide," *Journal of Solid State Chemistry*, 2002, 169: 1-5.
Feng et al., "Superplasticity and texture of SiC whiskers in a magnesium-based composite," *Scripta.Materialia*, 2005, 53: 361-365.
Ferguson et al., "Corrosion —Fatigue Performance of Magnesium Alloys," *International Journal of Modern Physics B*, vol. 17, Nos. 8 & 9, 2003, pp. 1601-1607.
Fernando, "Review of Corrosion and Corrosion Control of Magnesium Alloys and Composites," *J. Mater. Eng,*, 1989, 11:299-313.
Fischer et al., "Hydrogen in magnesium alloys and magnesium interfaces: preparation, electronic properties and interdiffusion," *J. Less-Common Metals*, 1991, 172:808-815.
Fontenier et al., "Study of a 'Platinum-Magnesium' Cell to Supply Current to a Pacemaker," *Bioelectrochemistry and Bioenergetics*, 1975, 2(2):106-123.
Fraunhofer EZRT, "Quantitative material analysis by dual energy computed tomography for industrial NDT applications," 2009, 1 pg.
Fraunhofer IIS - Poster (German), "Prinzip der hochauflösenden Comptuertomographie," 2009, 1 page.
Frei, "On the Role of Vitamin C and Other Antioxidants in Atherogenesis and Vascular Dysfunction," *Proceedings — Society for Experimental Biology and Medicine*, 1999, 222:196-204.
Gabrielli, Claude. "Use and Applications of Electrochemical Impedance Techniques," *Solartron.Analytical*, 1997, 1-102.
Garner et al., "Polypyrrole-heparin composites as stimulus-responsive substrates for endothelial cell growth," *J. Biomed. Mater. Res.*, 1999, 44: 121-129.
Gettleman et al., "Measurement of *in vivo* corrosion rates in baboons, and correlation with *in vitro* tests," Journal of Dental Research, 1980, 59: 689-707.
Gettleman et al., "Materials Science: Measurement of in vivo Corrosion Rates in Baboons, and Correlation with in vitro Tests," *Journal of Dental Research*, 1980, vol. 59, pp. 689-707.
Gomes et al., "Alternative tissue engineering scaffolds based on starch: processing methodologies, morphology, degradation and mechanical properties," *Materials Science and Engineering C*, 2002, 20:19-26.
Grassi et al., "Short-term administration of dark chocolate is followed by a significant increase in insulin sensitivity and a decrease in blood pressure in healthy persons," *Am. J. Clin. Nutr.*, 2005, 81(3):611-614.
Gray and Luan, "Protective coatings on magnesium and its alloys — a critical review," *J. Alloys. Compounds*, 2002, 336:88-113.
Griffiths et al., "Future devices: bioabsorbable stents," *Br. J. Cardiol. (Acute & Interventional.Cardiology)*, 2004, 11: AIC80-AIC84.

Grube, "Bioabsorbable Stents-The Boston Scientific & REVA Technology," *EuroPCR 2009*, 2009,.pp. 1-27.
Guo et al., "Manipulation of single-wall carbon nanotubes into aligned molecular layers," *Chem.Phys. Lett.*, 2002, 362:314-318.
Guo et al., "Multi-layer LB films of single-wall carbon nanotubes," *Physica B*, 2002, 323:235-236.
Gurib-Fakim, "Medicinal plants: Traditions of yesterday and drugs of tomorrow," *Molecular Aspects of Medicine*, 2006, 27:1-93.
Haferkamp et al., "Magnesium-Base-Alloys as Implant-Material Steps to the Production of Thin Components," *Magnesium*, 2000, 159-164.
Hau et al., "Surface-Chemistry Technology for Microfluidics," *J. Micromech, Microeng,*, 2003, 13:272-278.
Heublein et al., "Biocorrosion of magnesium alloys: a new principle in cardiovascular implant technology?" *Heart*, 2003, 89:651-656.
Heublein et al., "Degradation of Metallic Alloys - - A New Principle in Stent Technology?" *The American Journal of Cardiology, Eleventh Annual Symposium Transcatheter Cardiovascular Therapeutics Abstracts*, Sep. 22, 1999.
Heublein et al., "Bio-corrosion -- a new principle for temporary cardiovascular implants?" *European. Heart Journal, Journal of the European Society of Cardiology*, 2000, vol. 21, p. 286, Abstract No. P1605.
Heublein et al., "Local Tissue Engineering by Biocorrosion Vision or Reality?" *The American.Journal of Cardiology, TCT Abstracts/Poster*, Oct. 16, 2000.
Huang et al., "A Review on Polymer Nanofibers by Electro-spinning and their Applications in Nanocomposites," 2003, 63:2223-2253.
International Preliminary Report on Patentability in PCT/US07/73839 mailed Apr. 2, 2009.
International Preliminary Report on Patentability in PCT/US07/78429 mailed Apr. 2, 2009.
International Search Report and Written Opinion in PCT/US07/78449, mailed Jan. 13, 2009, 15 pages.
International Search Report and Written Opinion mailed Jan. 25, 2008 in PCT/US07/75072, 14 pages.
International Search Report for PCT/US07/66568 dated Oct. 8, 2007, 15 pages.
International Search Report/Written Opinion in PCT/US07/73839 mailed Apr. 16, 2008, 16 pages.
International Search Report/Written Opinion in PCT/US07/78411 mailed Mar. 6, 2008, 12 pages.
International Search Report/Written Opinion in PCT/US07/78429 mailed Mar. 28, 2008, 14 pages.
International Search Report/Written Opinion in PCT/US07/78505 mailed Mar. 4, 2008, 10 pages.
Ito et al., "Antioxidant action of eugenol compounds; role of metal ion in the inhibition of lipid peroxidation," *Food Chem. Toxicol.*, 2005, 43:461-466.
Ivanova and Ivanov, "Mechanisms of the extracellular antioxidant defend," *Experimental Pathology and Parasitology*, 2000, 4:49-59.
Jiang, "A review of wet impregnation —An alternatvie method for the fabrication of high performance and nano-structured electrodes of solid oxide fuel cells," *Materials Science and Engineering A*, 2006,418:199-210.
Kean and Davies, "Cathodic Protection," 7 pages, 1981; http://www.npl.co.uk/upload/pdf/cathodic_protection.
Kim et al., "Comprehensive study on vitamin C equivalent antioxidant capacity (VCEAC) of various polyphenols in scavenging a free radical and its structural relationship," *Crit. Rev. Food Sci. Nutr.*, 2004, 44(4):253-273.
Kim et al., "Effect of Anti-Oxidant (Carvedilol and Probucol) Loaded Stents in a Porcine Coronary Restenosis Model," *Circ. J.*, 2005, 69:101-106.
Kong et al., "Polyelectrolyte-functionalized multiwalled carbon nanotubes: preparation, characterization and layer-by-layer self assembly," *Polymer*, 2005, 46:2472-2485.
Kumar et al., "Polyanhydrides: an overview," *Advanced Drug Delivery Reviews*, 2002, 54:889-910.
Kurth et al., "Multilayer on Solid Planar Substrates: From Structure to Function" *Multi-layer Thins Films Sequential Assembly of Nanocomposite Materials*, 2003, Chapter 14, pp. 393-426.

Kurth et al., "Ultrathin Composite Films Incorporating the Nanoporous Isopolyoxomolybdate 'Keplerate' $(NH_4)_42[Mo_{132}O_{372}(CH_3COO)_{30}(H_2O)_{72}]$," *Chem. Mater.*, 2000, 12:2829-2831.

Kutsenko et al., "Structural Changes in Mg Alloy induced by plasma immersion ion implantation of Ag," *Acta Materialia*, 2004, 52:4329-4335.

Lambert et al., "Inhibition of carcinogenesis by polyphenols: evidence from laboratory investigations," *Am. J. Clin. Nutr.*, 2005, 81(suppl):2845-291S.

Lee et al., "Retentive and compressive strengths of modified zinc oxide-eugenol cements," *J. Dentistry*, 2000, 28:69-75.

Liao et al., "Fabrication of porous biodegradable polymer scaffolds using a solvent merging/particulate leaching method," *J. Biomed. Mater. Res.*, 2002, 59:676-681.

Lin et al., "Micropatterning proteins and cells on polylactic acid and poly(lactide-*co*-glycolide)," *Biomaterials*, 2005, 26:3655-3662.

Liu et al., "Characterizations of polypyrrole (PPy) nano-tubules made by templated ac electropolymerization," *European Polymer Journal*, 2005, 41: 2117-2121.

Liu et al., "Layer-By-Layer Ionic Self-Assembly of Au Colloids Into Multilayer Thin-Films with Bulk Metal Conductivity," *Chemical Physics Letters*, 1998, 298:315-319.

Liu et al., "Functional Polyoxometalate Thin Films via Electrostatic Layer-by-Layer Self-Assembly," *Journal of Cluster Science*, 2003, 14:405-419.

Liu et al., "Sol-gel deposited TiO2 film on NiTi surgical alloy for biocompatibility improvement," *Thin Solid Films*, 2003, 429:225-230.

Liu, *Introduction to Corrosion and Protection*, Corrosion and Protection Centre, School of Materials, The University of Machester, 2006, 36 pages.

Lu et al., "Theoretical analysis of calcium phosphate precipitation in simulated body fluid," *Biomaterials*, 2005, 26:1097-1108.

Macias et al., "Electrospun mesoporous metal oxide fibers" *Microporous and Mesoporous Material*, 2005, 86: 1-13.

Maier et al., "High concentrations of magnesium modulate vascular endothelial cell behaviour in vitro," *Biochim. Biophys. Acta*, 2004, 1689:6-12.

Matsuoka et al., "Hyperthermia Using Magnetite Cationic Liposomes for Hamster Osteosarcoma," *Biomagnetic Research and Technology*, Mar. 25, 2004, pp. 1-6.

Medical Device Daily, "Conor Cites Positive 12-month Results for Its CoStar Stent", May 2005 (1 page).

*Middleton and Tipton.* "*Synthetic Biodegradable Polymers as Medical ices*," http://www.devicelink.com/mpb/archive/98/03/002.html, Mar. 1998, 9 pages.

Mihailovic et al., "Unusual Magnetic State in Lithium-Doped MoS₂Nanotubes," *Phys. Rev. Lett.*, 2003, 90 146401-1-4.

Mikos and Temenoff, "Formation of highly porous biodegradable scaffolds for tissue engineering," *Electronic Journal of Biotechnology*, 2000, 3(2):114-119.

Mohanty et al. "Evaluation of soft tissue response to a poly[urethane urea]," *Biomaterials*, 1992, 13(10):651-656.

Mohanty et al., "Effect of *Curcuma longa* and *Ocimum sanctum* on myocardial apoptosis in experimentally induced myocardial ischemic-reperfusion injury," *BMC Complementary and Alternative Medicine*, 2006, 63:3-14.

Molnar and Garai, "Plant-derived anti-inflammatory compounds affect MIF tautomerase activity," *International Immunopharmacology*, 2005, 5:849-856.

Moskaug et al., "Polyphenols and glutathione synthesis regulation," *Am. J. Clin. Nutr.*, 2005,.81 (suppl):277S -283S.

Naderi et al., "Effect of some volatile oils on the affinity of intact and oxidized low-density lipoproteins for adrenal cell surface receptors," *Mol. Cell. Biochem.*, 2004, 267:59-66.

Niemeyer et al., "Magnesium alloys as biodegradable metallic implant materials for cardiovascularic and orthopaedic surgery," *Euromat 2001, 7ᵗʰ European Conference on Advanced Materials and Processes*Jun. 10-14, 2001 (Abstract).

Niinisto, "Atomic Layer deposition: A key technology for the controlled growth of oxide thin films for advanced applications," *Proc. Estonian Acad. Sci. Phys. Math.*, 2003, 52(3):266-276.

Nilsson et al., "Development of a dosage method for electrochemical treatment of tumours: a simplified mathematical model," *Bioelectrochemistry and Bioenergetics*, 1998, 47:11-18.

Ou et al., "Protective effects of eugenol against oxidized LDL-induced cytotoxicity and adhesion molecule expression in endothelial cells," *Food Chem. Toxicol.*, 2006, 44:1485-1495.

Park et al., "Microstructural change and precipitation hardening in melt-spun Mg-X-Ca alloys," *Science and Technology of Advanced Materials*, 2001, 2:73-78.

Peuster et al. "Long-term biocompatibility of a corrodible peripheral iron stent in the porcine of descending aorta," *Biomaterials*, 2006, 4955-4962.

Peuster et al., "A novel approach to temporary stenting: degradable cardiovascular stents produced from corrodible metal-results 6-18 months after implantation into New Zealand white rabbits," *Heart*, 2001, 86(5):563-569.

Prasse et al., "Electric Anisotropy of Carbon Nanofibre/Epoxy Resin Composites Due to Electric Field Induced Alignment," *Composites Science and Technology*, 2003, 63:1835-1841.

Ratnam et al., "Role of antioxidants in prophylaxis and therapy: A pharmaceutical perspective," *J. Controlled Release*, 2006, 113:189-207.

Remskar et al., "Self-Assembly of Subnanometer-Diameter Single-Wall MoS₂ Nanotubes " 2001, 292:479-481.

Rezwan et al., "Biodegradable and bio active porous polymer/inorganic composite scaffolds for bone tissue engineering, *Biomaterials*, 2006, 27:3413-3431.

Rhule et al., "Polyoxometalates in Medicine," *Chem. Rev.*, 1998, 98:327-357.

Rutledge et al., "Electrostatic Spinning and Properties of Ultrafine Fibers," *National Texile Center Annual Report*, Nov. 2001, M01-D22, pp. 1-10.

Ryan et al., "Fabrication methods of porous metals for use in orthopaedic applications," *Biomaterials*, 2006, 27:2651-2670.

Sastry et al., "DNA-Mediated Electrostatic Assembly of Gold Nanoparticles into Linear Arrays by a Simple Drop-Coating Procedure," *Appl. Phys. Lett.*, 2001, 78:2943-2945.

Satoh et al., "Effect of Antioxidants on Radical Intensity and Cytotoxic Activity of Eugenol," *Anticancer Res.*, 1998, 18:1549-1552.

Sawitowski et al., "Nanoporous Alumina Coating for Medial Implants and Stents — Radiotherapy, Drug Delivery, Biological Compatibility," *Materials Research Society Symposium Proceedings*, 1999, 581:523-528.

Sawitowski, "New Drug Delivery Systems — Examples of Applied Nanotechnoloby," *VDE World Microtechnologies Congress*, Sep. 25-27, 2000 Expo 2000, Hannover, Germany, Proveeds vol. 1, p. 343-346.

Sawyer et al., "Electrochemical Criteria in the Choice of Materials used in Vascular Prostheses," *Biophysical Mechanisms in Vascular Homeostasis and Intravascular Thrombosis*, 1965, pp. 337-348.

Schetky, "Shape Memory Alloys," *Encyclopedia of Chemical Technology* (3rd ed.), 1982, John Wiley & Sons, 20:726.

Shaw, "Corrosion Resistance of Magnesium Alloys, " *ASM Handbook vol. 13A: Corrosion: Fundamentals, Testing, and Protection.* 2003, 5 pages.

Shenoy et al., "Role of Chain Entanglements on Fiber Formation During Electrospinning of Polymer Solutions: Good Solvent, Non-Specific Polymer-polymer Interaction Limit," *Polymer*, 2005, 46:3372-3384.

Shi et al., "A novel electrically conductive and biodegradable composite made of polypyrrole nanoparticles and polylactide," *Biomaterials*, 2004, 25:2477-2488.

Shin, "Experimental Characterization of Electrospinning. the Electrically Forced Jet and Instabilities," *Polymer*, 2001, 42:9955-9967.

Singh et al., "Electrocatalytic Activity of Electrodeposited Composite Films of Polypyrrole and $CoFe_2O_4$ Nanoparticles Towards Oxygen Reduction Reaction," *Electrochimica Acta*, 2004, 49:4605-4612.

Song et al., "Galvanic corrosion of magnesium alloy AZ9ID in contact with an aluminium alloy, steel and zinc," *Corrosion Science*, 2004, 46:955-977.

Stoclet et al., "Vascular protection by dietary polyphenols," *Eur. J. Pharmacol.*, 2004, 500:299-313.

Straumal et al., "Vacuum arc deposition of protective layers on glass and polymer" *Thin Solid Films*, 2001, 383:224-226.
Suhaj, "Spice antioxidants isolation and their antiradical activity: a review,"*J. Food Composition and Analysis*, 2006, 19:531-537.
Sukhorukov et al., "Comparative Analysis of Hollow and Filled Polyelectrolyte Microcapsules Templated on Melamine Formaldehyde and Carbonate Cores," *Macromol. Chem. Phys.*, 2004, 205:530-535.
Suslick et al., "The photochemistry of chromium, manganese, and iron porphytin complexes," J. Chem., 1992, 16:633-642.
Tada et al., "Distribution of pH during galvanic corrosion of a Zn/steel couple," *Electrochimica Acta*, 2004, 48:1019-1026.
Tan et al., "Systematic Parameter Study for Ultra-Fine Fiber Fabrication Via Electrospinning Process," *Polymer*, 2005, 46:6128-6134.
Tian et al., "Corrosion resistance improvement of magnesium alloy using nitrogen plasma ion implantation," *Surface & Coatings Technology*, 2005, 198:454-458.
Vermette et al., "Immobilized Liposome Layers for Drug Delivery Applications," *J. Controlled Release*, 2002, 80:179-195.
von Euler et al., "Cell proliferation and apoptosis in rat mammary cancer after electrochemical treatment (EChT)," *Bioelectrochemistry*, 2004, 62:57-65.
Vrbanic et al., "Air-Stable Monodispersed $Mo_6S_3I_6$ Nanowires," *Nanotechnology*, 2004, 15:635-638.
Wallerath et al., "A blend of polyphenolic compounds explains the stimulatory effect of red wine on human endothelial NO synthase," *Nitric Oxide*, 2005, 12:97-104.
Wan et al., "Influence of Plasma Immersion Ion Implantation on Corrosion Properties of Magnesium," *Southwest Jiaotong University*, 2005, Chengu, 11 pages.
Wang et al., "Nonlinear optical properties of thin iron films grown on MgO (100) by uplsed laser deposition," *Thin Solid Films*, 2005, 471:86-90.
Wang et al., "Characterisation of Severely Deformed Austenitic Stainless Steel WIre" *Materials Science and Technology*, 21(11):1323-1328 2005.
Wang, "Recent development of non-platinum catalysts for oxygen reduction reaction," *J. Power Sources*, 2005, 152:1-15.
Weber et al., "Hardness and corrosion resistance of single-phase nitride and carbide on ion," *Materials Science and Engineering*, 1995, 99:205-210.
Weh et al., "Evolution of afractal-like surface structures in layers of polyacrylonitrile solutions by interfacial dynamic processes," *J. Colloid and Interface Science*, 2004, 271: 407-415.
Widmer et al., "Manufacture of porous biodegradable polymer conduits by an extrusion process for guided tissue regeneration," *Biomaterials*, 1998, 19:1945-1955.
Wieneke et al., "Stent Coating: A New Approach in Interventional Cardiology," *Herz*, 2002, 27(6):518-526.
Williamson and Manach, "Bioavailability and bioefficacy of polyphenols in humans. II. Review of 93 intervention studies,"*Am. J. Clin. Nutr.*, 2005, 81(suppl):2435-2555.
Witte et al., "In vitro and in vivo corrosion measurements of magnesium alloys," *Biomaterials*, 2006,27:1013-1018.
Yamaguchi et al., "Mg2Si Coating Technology on Magnesium Alloys to Improve Corrosion and Wear Resistance", *JOM*, 2004, p. 343.
Yi et al., "Characterization of a bioactive nanotextured surface created by controlled chemical oxidation of titanium," *Surface Science*, 2006, 600:4613-4621.
You et al., "The Effect of Calcium Additions on the Oxidation Behavior in Magnesium Alloys," *Scripta mater.*, 2000, 42:1089-1094.
Yu and Uan, "Sacrificial Mg film anode for cathodic protection of die cast Mg-9-wt.%-1 wt.%Zn alloy in NaC1 aqueous solution," *Scripta Mat.*, 2006, 54:1253-1257.
Yue et al., "Improvement in the Corrosion Resistance of Magnesium ZK60/SiC Composite by Excimer Laser Surface Treatment," *Scripta Materialia*, 1998, 38(2):191-198.

*Zeta Potential-An Introduction in 30 Minutes, Technical Note: http://www.nbtc.cornell.edu/facilities/downloads/Zeta%20potential%20-%20introduction%20in%2030%20tninutes.pdf, Retrieved from the Internet on May 9, 2005 (6 pages)*.
Zhang et al., "Improving multilayer films endurance by photoinduced interaction between Dawson-type polyoxometalate and diazo resin," *Materials Chemistry and Physics*, 2005, 90:47-52.
Zhang et al., "Natural Polyelectrolyte Films Based on Layer-by-Layer Deposition of Collagen and Hyaluronic Acid," *Biomaterials*, 2005, 26:3353-3361.
Zhang et al., "Ways for fabricating stable layer-by layer self-assemblies: combined ionic self-assembly and post chemical reaction," *Colloids and Surfaces A: physiochemical and Engineering Aspects*, 2002, pp. 198-200, 439-442.
Zhou et al., "Drug-loaded, Magnetic, hollow silica nanocomposites for nanomedicine," *Nanomedicine: Nanotechnology, Biology and Medicine*, 2005, 1:233-237.
Zucchi et al., "Influence of a silane treatment on the corrosion resistance of a WE43 magnesium alloy," *Surface Coatings Technol.*, 2006, 200:4136-4143.
Li et al., "The corrosion inhibition of the self assembled Au, and Ag nonoparticles films on the surface of copper," Colloids and Surfaces A: Physiochem. Eng. Aspects," 2006, 273: 16-23.
International Preliminary Report on Patentability from PCT/US08/75976 dated Mar. 25, 2010, mailed Nov. 25, 2008, 8 pages.
Viswanathamurthi et al., "Preparation and morphology of niobuim oxide fibres by electrospinning," *Chemical Physics Letters*, 2003, 374: 79-84.
Authorized Officer Henrique Amaro, International Preliminary Report on Patentability from PCT/US09/043326 mailed Nov. 18, 2010, 7 pages.
Authorized Officer Jasmine Messemanne, International Search Report from PCT/US09/051965 mailed Aug. 20, 2010, 13 pages.
Authorized Officer Jasmine Messemanne, International Preliminary Report on Patentability from PCT/US09/051965 mailed Feb. 10, 2011, 8 pages.
Authorized Officer Antonio Espuch, International Preliminary Report on Patentability in PCT/US09/49422 mailed 13 Jan. 2011, 7 pages.
Authorized Officer Aurore Schneider, International Preliminary Report on Patentability from PCT/US2010/042772 mailed Feb. 4, 2011, 9 pages.
Authorized Officer Henrique Amaro, International Preliminary Report on Patentability in PCT/US2009/43326 mailedNov. 18, 2010, 7 pages.
Authorized Officer Antoine Laurent, International Preliminary Report on Patentability in PCT/US09/046750 mailed Dec. 23,2010, 8 pages.
Deepwater, "Galvanic Series," http://corrosion-doctors.org/definitions/galvanic-series.htm> on Mar. 11, 2011, 5 pages.
Wikipedia, the Free Encyclopedia, "Galvanic Corrosion." <http://en.wikipedia.org/wiki/Galvanic_corrosion> on Mar. 11, 2011, 7 pages.
Authorized Officer Mary Celine, International Search Report from PCT/US2010/060412 mailed Feb. 21, 2011, 10 pages.
Dumas et al., "Characterization of magnesium fluoride thin films produced by argon ion beam-assisted deposition," *Thin Solid Films*, 2001, pp. 61-68.
Authorized Officer Razik Menidjel, International Preliminary Report on Patentability from PCT/US09/059424, mailed May 5, 2011, 8 pages.
Authorized Officer Aurore Schneider, International Preliminary Report on Patentability from PCT/US2010/042772 mailed Feb. 4, 2011, 9 pages.
US 6,533,715, 03/2003, Hossainy et al. (withdrawn)

* cited by examiner

ENDOPROSTHESIS WITH THREE-DIMENSIONAL DISINTEGRATION CONTROL

CLAIM OF PRIORITY

This application claims the benefit of priority under 35 U.S.C. §119(e) to U.S. provisional application Ser. No. 60/821,260, filed Aug. 2, 2006, which is incorporated herein by reference in its entirety.

FIELD OF THE INVENTION

This invention relates to medical devices, such as endoprostheses, and methods of making such devices.

BACKGROUND

The body includes various passageways including blood vessels such as arteries, and other body lumens. These passageways sometimes become occluded or weakened. For example, they can be occluded by a tumor, restricted by plaque, or weakened by an aneurysm. When this occurs, the passageway can be reopened or reinforced, or even replaced, with a medical endoprosthesis. An endoprosthesis is an artificial implant that is typically placed in a passageway or lumen in the body. Many endoprostheses are tubular members, of which examples include stents, stent-grafts, and covered stents.

Many endoprostheses can be delivered inside the body by a catheter. Typically the catheter supports a reduced-size or compacted form of the endoprosthesis as it is transported to a desired site in the body, for example the site of weakening or occlusion in a body lumen. Upon reaching the desired site the endoprosthesis is installed so that it can contact the walls of the lumen.

One method of installation involves expanding the endoprosthesis. The expansion mechanism used to install the endoprosthesis may include forcing it to expand radially. For example, the expansion can be achieved with a catheter that carries a balloon in conjunction with a balloon-expandable endoprosthesis reduced in size relative to its final form in the body. The balloon is inflated to deform and/or expand the endoprosthesis in order to fix it at a predetermined position in contact with the lumen wall. The balloon can then be deflated, and the catheter withdrawn.

In another delivery technique, the endoprosthesis is formed of an elastic material that can be reversibly compacted and expanded (e.g., elastically or through a reversible phase transition of its constituent material). Before and during introduction into the body until it reaches the desired implantation site, the endoprosthesis is restrained in a compacted condition. Upon reaching the desired site, the restraint is removed, for example by retracting a restraining device such as an outer sheath, enabling the endoprosthesis to self-expand by its own internal elastic restoring force.

To support or keep a passageway open, endoprostheses are sometimes made of relatively strong materials, such as stainless steel or Nitinol (a nickel-titanium alloy), formed into struts or wires. The material from which an endoprosthesis is made can impact not only the way in which it is installed, but its lifetime and efficacy within the body.

SUMMARY

A method of making a support structure for a medical device, wherein the support structure has a shape, the method comprising: constructing a first layer of a first material by direct metal laser sintering, wherein the first layer has a shape that corresponds to the shape of the support structure; and introducing a first nitrogen content into a first part of the first layer by excimer laser nitriding.

A method of controlling disintegration of a medical device in an organism, comprising: constructing a support structure by building up alternating layers by direct metal laser sintering, and by excimer nitriding; and implanting the device into the organism, wherein the corrosion of the support structure occurs over a first period of time inside the organism.

A support structure for a medical device, wherein the support structure comprises alternating layers, wherein at least a first layer is formed by direct metal laser sintering, and at least a second layer, adjacent to the first layer, has a nitrogen content introduced into it by laser excimer nitriding.

A medical device for implantation into an organism, comprising: a support structure, wherein the support structure is configured to ensure steady biodisintegration thereof over a period of time inside the organism.

A method of using a medical device that comprises a support structure, wherein the support structure is biodisintegrable, the method comprising implanting the medical device in a body passageway of an organism.

The various details of one or more embodiments of the invention are set forth in the accompanying drawings and the description hereinbelow. Other aspects, features, and advantages of the invention will be apparent from the description and drawings, and from the claims.

BRIEF DESCRIPTION OF THE DRAWINGS

Like reference symbols in the various drawings indicate like elements.

DETAILED DESCRIPTION

Figure 1A:
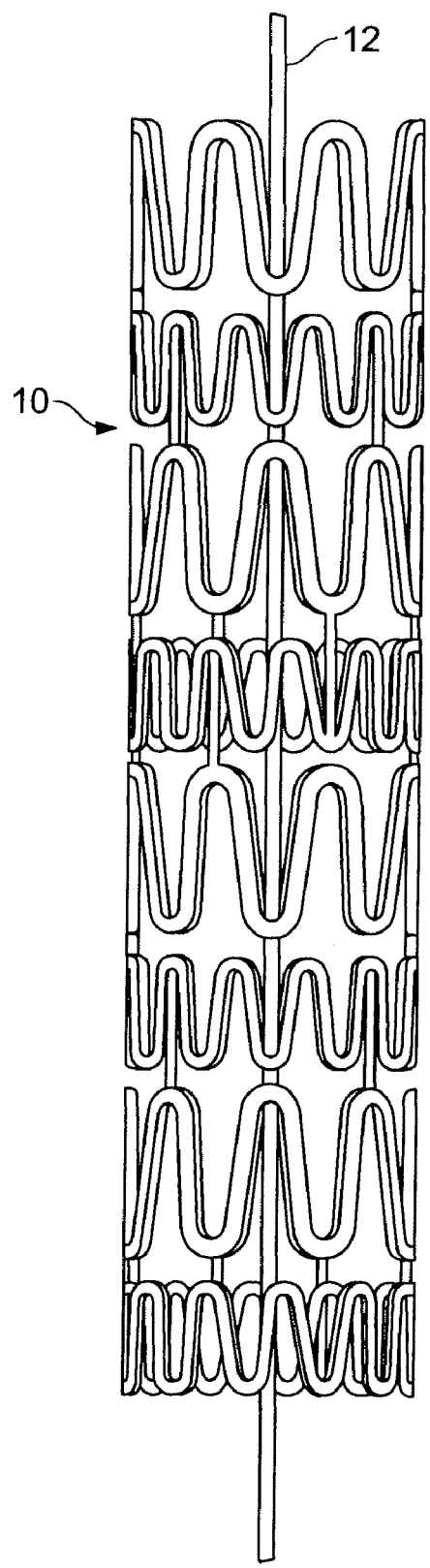
FIGS. 1A-1H and 1J-1L are respectively, perspective views of exemplary endoprostheses.
Figure 1B:
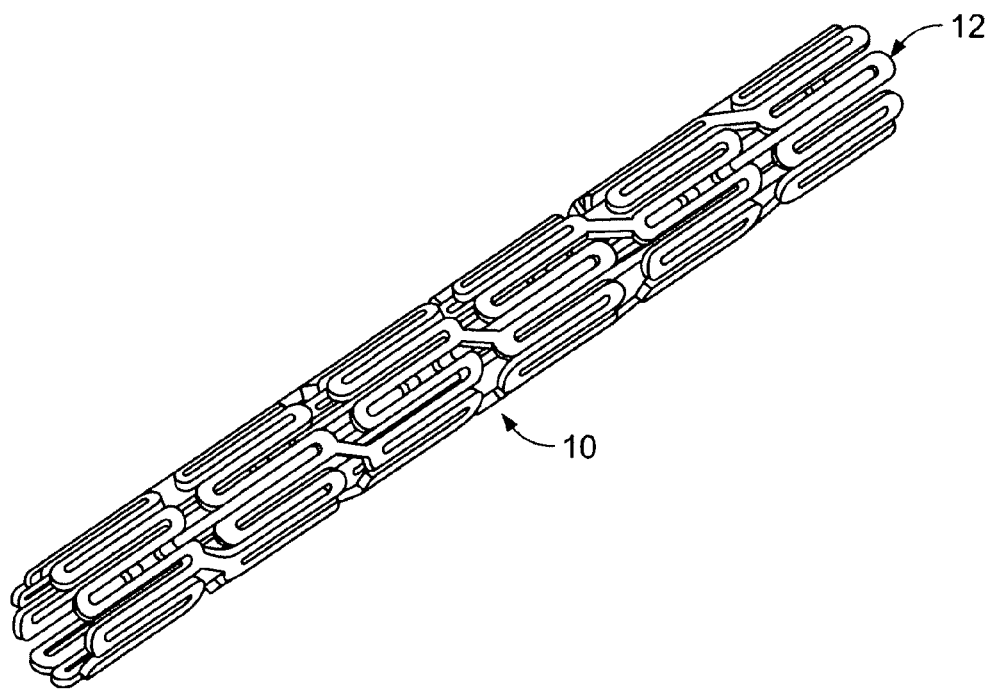
Figure 1C:
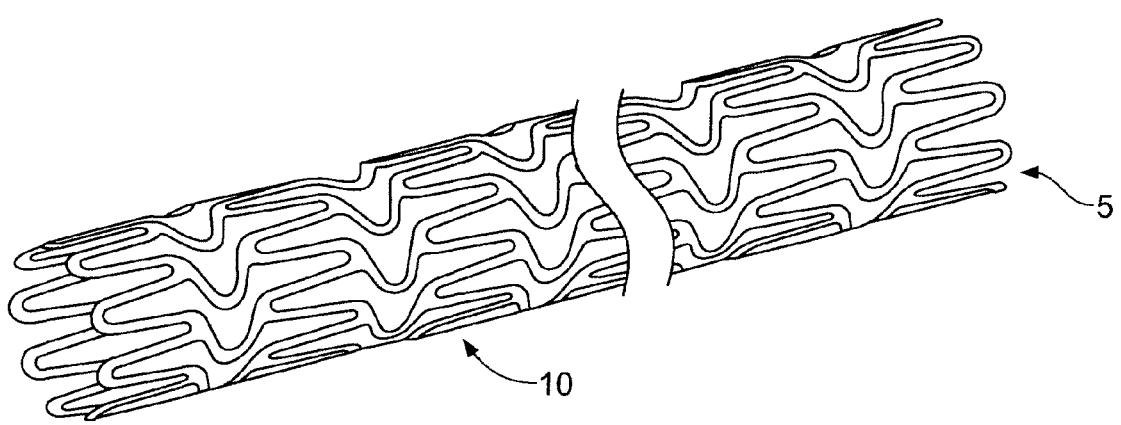

Although endoprostheses have been highly effective at removing restrictions in body passageways, a number of problems have emerged that arise from their long-term placement. Restenosis is one; another is that, over time, microbes and other material can build up on a structure such as a stent and cause their own obstruction to free passage of body fluids through the lumen. Recently, there has been a move towards making endoprostheses out of bio-absorbable materials, such as magnesium, or iron alloys and biodegradable polymers, that ensure that the device structure naturally degrades over time. Alternatively, magnesium layers may be treated with HF to create layers of Magnesium Fluoride. Such materials may, however, disintegrate too quickly for the useful life of an endoprosthesis—the mechanical performance of the endoprosthesis typically has to be maintained for at least three weeks—thus requiring endoprostheses to be made out of thicker elements than would be preferred. Uneven degradation is also a significant problem. Slight variations in a number of uncontrollable environmental parameters such as temperature, fluid flow-rate, and local concentrations of critical agents, can cause a huge difference in the degradation course of different regions of exposed surface area. In many instances, the endoprosthesis disintegrates in a non-uniform manner, potentially releasing large fragments that can migrate and cause boli and secondary blockages in narrower vessels at other locations.

Accordingly, the devices herein address such issues by making the support structures by processes, and from materials, that ensure that the support structures break down evenly across the entire structures, and over time, and significantly reduce the chance for large fragments being released.

Definitions

A biocompatible material is a material that can be introduced into living tissue or a living system, and is non-toxic or non-injurious to the tissue or system, and does not cause an immunological reaction or rejection in the concentrations in which it is deployed. The devices and methods described herein may be used with both materials that are biocompatible and those that are not.

As used herein, a "biodisintegrable material" is a material that undergoes at least one of dissolution, degradation, absorption, erosion, corrosion, resorption, chemical transformation, or other disintegration processes over the period that a device formed at least in part from the biodisintegrable material is designed to reside in an organism. Chemical transformation can include oxidation or other chemical reactions of the material. In some embodiments a biodisintegrable material is also biocompatible.

In specific embodiments, a biodisintegrable material is a material that exhibits substantial mass or density reduction by one or more of dissolution, degradation, absorption, erosion, corrosion, resorption, decomposition, degeneration, chemical transformation and/or other disintegration processes after it is introduced into an organism. The disintegration occurs to a desirable extent in a timeframe that can provide a clinical benefit. Mass reduction of a biodisintegrable device can also occur, but in some cases does not occur, by fragmentation of the material. The disintegration can be the result of the chemical and biological interaction of the material with the physiological environment into which it is implanted and/or can be initiated by applying a suitable triggering influence, such as a chemical reactant or source of energy to the device.

In some embodiments, a biodisintegrable material for use with the present invention exhibits substantial mass reduction after a period of time for which a function of the material, such as support of a lumen wall or delivery of a therapeutic agent in the immediate vicinity of the device, is no longer needed or desirable. By "a substantial reduction" is meant that the biodisintegrable material exhibits a mass reduction through biodisintegration of at least about 10%, at least about 20%, at least about 25%, at least about 30%, at least about 50%, at least about 75%, or at least about 90%, after a period of implantation. The period of implantation over which the mass reduction through biodisintegration takes place can be chosen to be one day or more, 14 days or more, 30 days or more, 60 days or more, 90 days or more, 180 days or more, 300 days or more, 600 days or more, or about 1,000 days or less. Thus, it would be understood that the level of biodisintegrability can be tailored to achieve a given level of mass reduction over a certain desired duration. For example, a medical device may be required to have reached a 75% reduction in mass in 30 days. In another embodiment, it may be required to have attained a 30% reduction in mass in 180 days. It would also be understood by one of ordinary skill in the art that a period of days, such as 300 days, as used herein, entails a level of imprecision such that periods of 3-5 days either shorter or longer than the period in question are also acceptable equivalent timescales for measuring levels of biodisintegrability.

In certain embodiments of the present invention, only portions of the device exhibit biodisintegrability. For example, an exterior layer or coating may be non-biodisintegrable, while an interior layer or body is biodisintegrable. It is also consistent with the methods and devices described herein that biodisintegrable elements are included within a polymeric matrix that is biostable (as defined hereinbelow), such that upon disintegration of the matrix, the device containing the matrix, such as a support structure, becomes less stiff.

A degradable material is a material that can dissociate, depolymerize, or otherwise reduce in molecular weight from its starting molecular weight, such that a resulting compound is soluble in an aqueous medium such as water or, if insoluble, can be suspended in a body fluid and transported away from an implantation site without obstructing the flow of the body fluid. A biodegradable material is one that will degrade into biocompatible compounds as part of a biological process.

In some embodiments, a biodegradable material exhibits substantial mass reduction after a period of time for which a function of the material, such as support of a lumen wall or delivery of a therapeutic agent in the immediate vicinity of the device, is no longer needed or desirable. By "a substantial reduction" is meant that the biodegradable material exhibits a mass reduction through biodegradation of at least about 10%, at least about 20%, at least about 25%, at least about 30%, at least about 50%, at least about 75%, or at least about 90%, after a period of implantation. The period of implantation over which the mass reduction through biodegradation takes place can be chosen to be one day or more, 14 days or more, 30 days or more, 60 days or more, 90 days or more, 180 days or more, 300 days or more, 600 days or more, or about 1,000 days or less. Thus, it would be understood that the level of biodegradability can be tailored to achieve a given level of mass reduction over a certain desired duration. For example, a material may be required to have reached a 25% reduction in mass in 600 days. In another embodiment, it may be required to have attained a 30% reduction in mass in 300 days. It would also be understood by one of ordinary skill in the art that a period of days, such as 180 days, as used herein, entails a level of imprecision such that periods of 3-5 days either shorter or longer than the period in question are also acceptable equivalent timescales for measuring levels of biodegradability.

A resorbable material is a material that is soluble, biodisintegrable as defined herein, or is an aggregate of soluble and/or disintegrable material(s) with insoluble material(s) such that, with the resorption of the soluble and/or disintegrable materials, the residual insoluble materials are of sufficiently fine size that they can be suspended in a body fluid and transported away from the implantation site without obstructing the flow of the body fluid. Ultimately, the particles are eliminated from the body either by excretion in fluids such as perspiration, urine or feces, or are themselves dissolved, degraded, corroded or otherwise metabolized into soluble components that are then excreted from the body. A bioresorbable material is a resorbable material that is biocompatible.

In certain embodiments, as further described herein, biostable materials, e.g., polyelectrolytes, may be utilized. As used herein, a "biostable material" is a material that does not undergo substantial dissolution, degradation, absorption, erosion, decomposition, corrosion, chemical transformation, resorption and/or other disintegration processes over the period that the material is designed to reside in an organism.

The term "body fluid" as used herein refers to fluids in the body of an organism—especially a mammal—including, but not limited to, blood, urine, saliva, lymph, plasma, gastric, biliary, or intestinal fluids, seminal fluids, and mucosal fluids or humors.

The terms "therapeutic agent", "pharmaceutically active agent", "pharmaceutically active material", "pharmaceutically active ingredient", "drug" and other related terms may be used interchangeably herein and include, but are not limited to, small organic molecules, peptides, oligopeptides, proteins, nucleic acids, oligonucleotides, genetic therapeutic agents, non-genetic therapeutic agents, vectors for delivery of genetic therapeutic agents, cells, and therapeutic agents identified as candidates for vascular treatment regimens, for example, as agents targeting restenosis.

By small organic molecule is meant an organic molecule having 50 or fewer carbon atoms, and fewer than 100 non-hydrogen atoms in total.

As used herein, an "antimicrobial agent" is any agent that is harmful to microbes, especially pathogenic bacteria.

As used herein, "treatment" includes an amelioration of a disease or condition, including the prevention of a disease or condition, the reduction or elimination of symptoms associated with a disease or condition, or the substantial or complete elimination of a disease or condition.

Overview

Medical devices having a mechanical support structure that has controllable biodisintegrability, and methods of making the devices, are disclosed.

The support structure of the medical device can be generally tubular in shape and can be a part of a stent. Endoprostheses such as stents come in a variety of shapes. Simple tubular structures having a single tube, or with complex structures, such as branched tubular structures, can be used.

Devices, such as stents, may be formed from many known constructions such as cross-hatched or mesh filaments or interlocking loops. Almost all have a complex and delicate structure that permits them to deform in a manner necessary for implantation, as well as to be inflated into the configuration that they adopt in situ. Exemplary stents 10 having a lattice, or cage-like, framework are shown in FIGS. 1A-1H and 1J -1L. The structures in FIGS. 1A-1C, and 1E-1L are all made of a single piece of metal. The structure in FIG. 1D is made of a helically wound wire 4, and may comprise several interlocking pieces, arranged in a wave-like configuration 12 and having gaps 5.

Figure 1D:
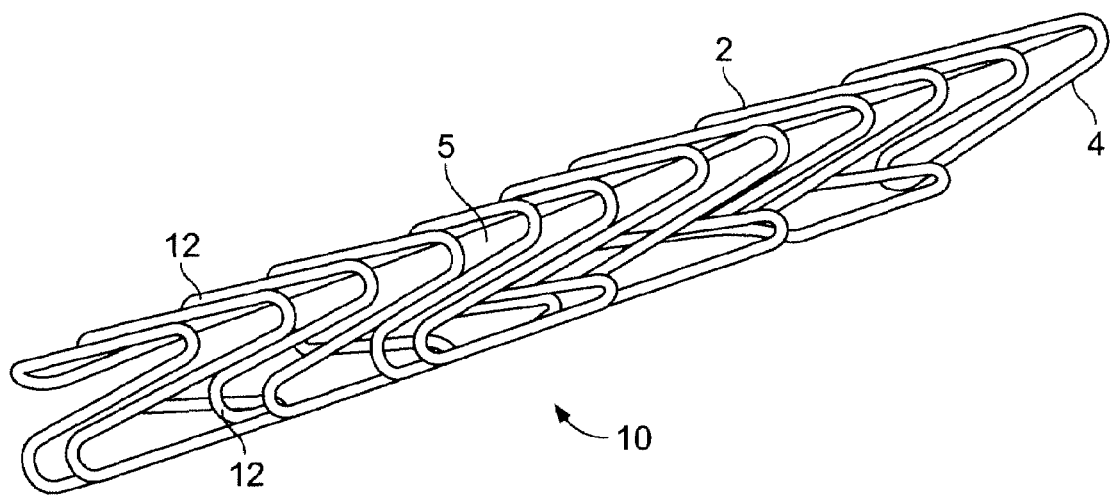
Figure 1E:
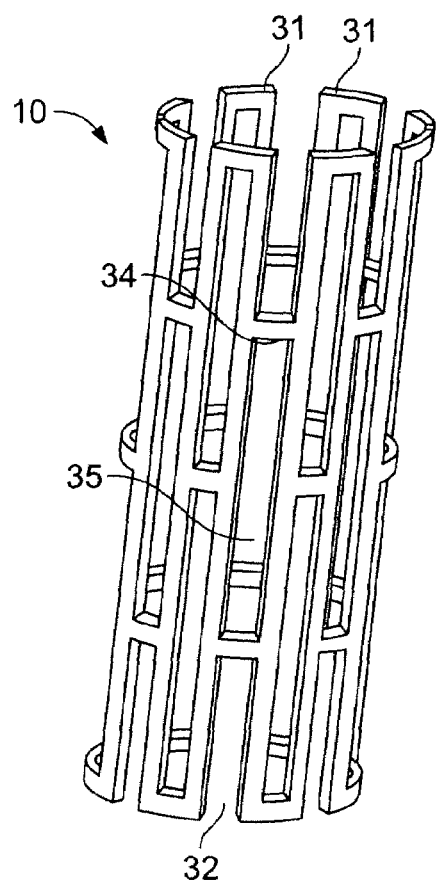
Figure 1F:
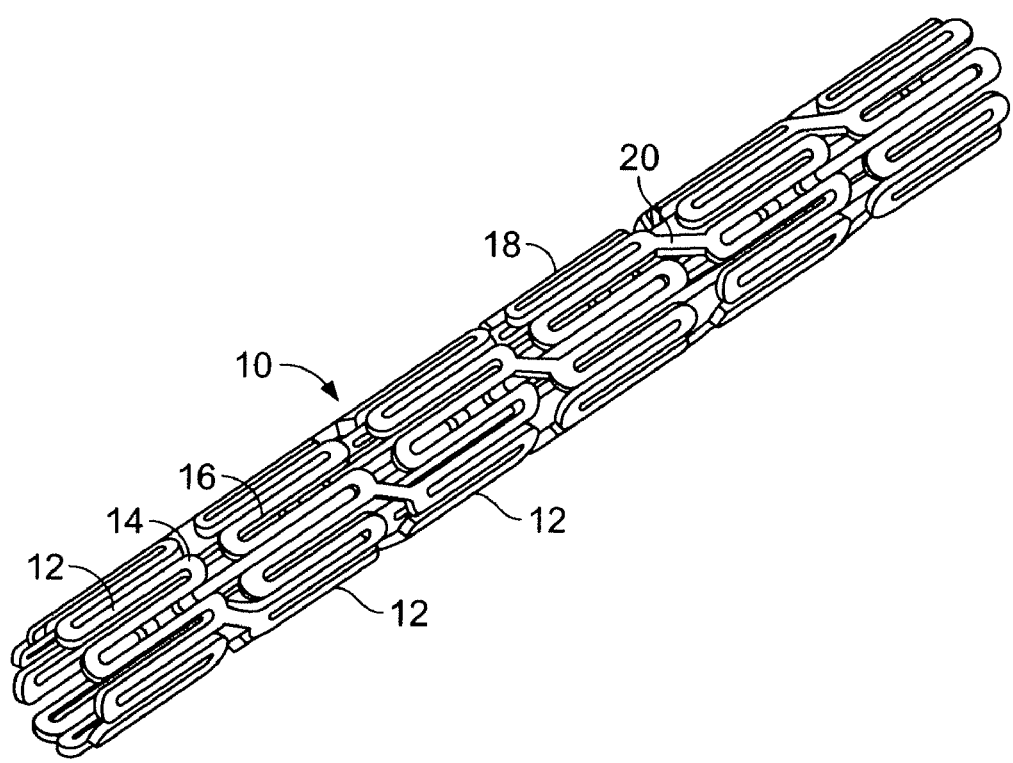
Figure 1G:
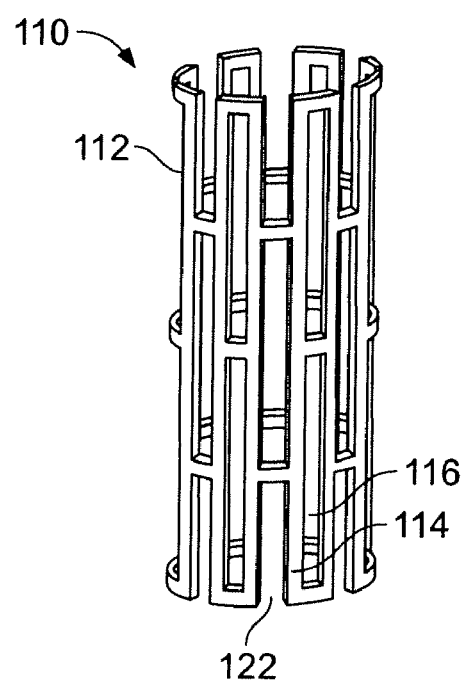
Figure 1H:
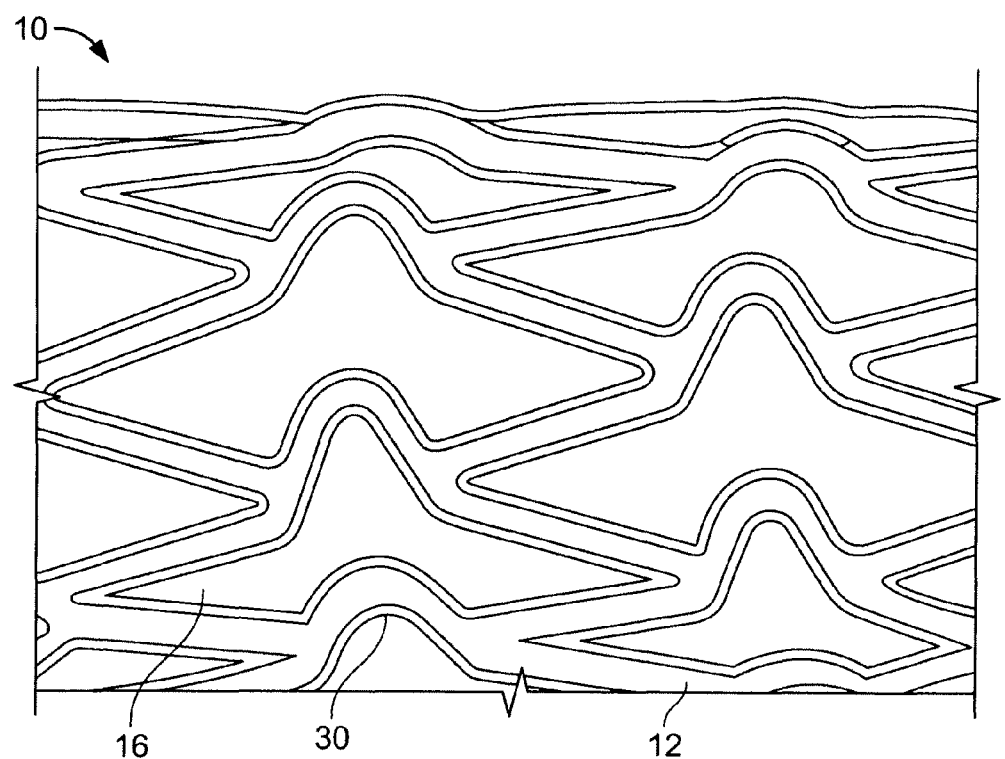
Figure 1J:
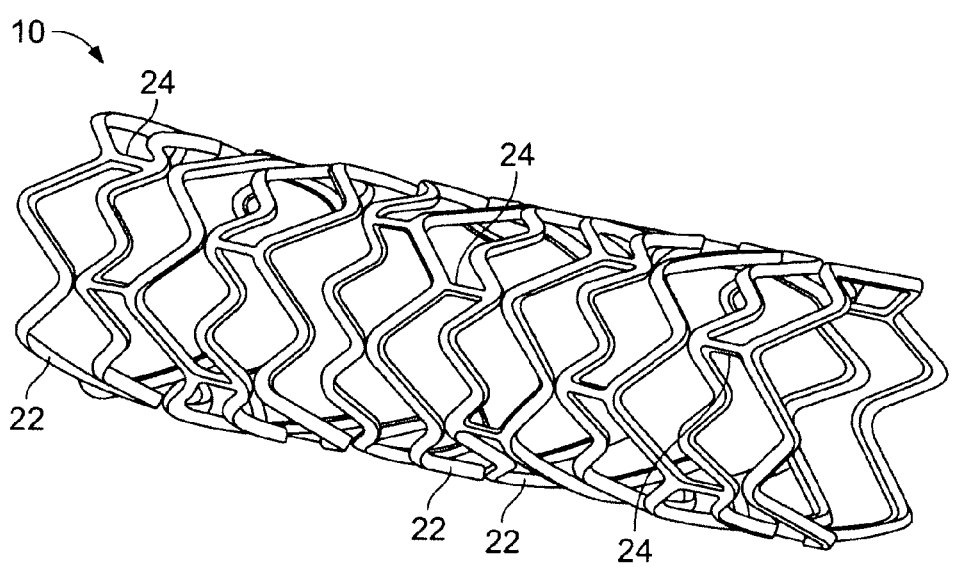

In FIG. 1A, 12 is a control wire used while coating stent 10. Preferred configurations for the stent of FIG. 1D are described in U.S. Patent Application Publication No. 2004/0181278, Sep. 16, 2004. FIG. 1E shows an expandable and deformable tubular stent, as described in U.S. Pat. No. 4,733,665. Longitudinal struts 31 are connected to one another by one or more tabs 34, which serve to define one or more slots 32, and spaces 35. In FIG. 1F, stent 10 is constructed from wire-like members 12, bent into serpentine configurations 12, 14, 16, and connected to one another by interconnecting members 20, as further described in U.S. Patent Application Publication No. 2001/0032014, Oct. 18, 2001. In FIG. 1G, a further stent embodiment 110 has wire members 112, 114 configured into a rectangular mesh having gaps 122 at the ends, and enclosed spaces 116 in the middle. FIG. 1H shows a further embodiment of a stent in which wire members 12 are configured to enclose irregular shaped gaps 16, and where wire members 12 are coated with a polymer layer 30. In FIG. 1J, wires 22 are configured into a zig-zag arrangement, linked to one another with interconnecting members 24.

Figure 1K:
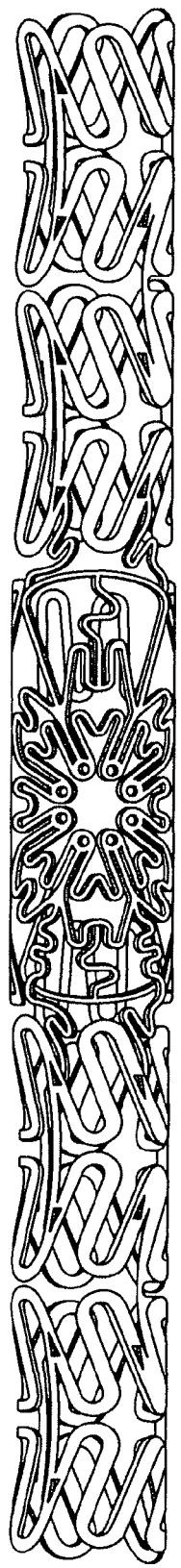
Figure 1L:
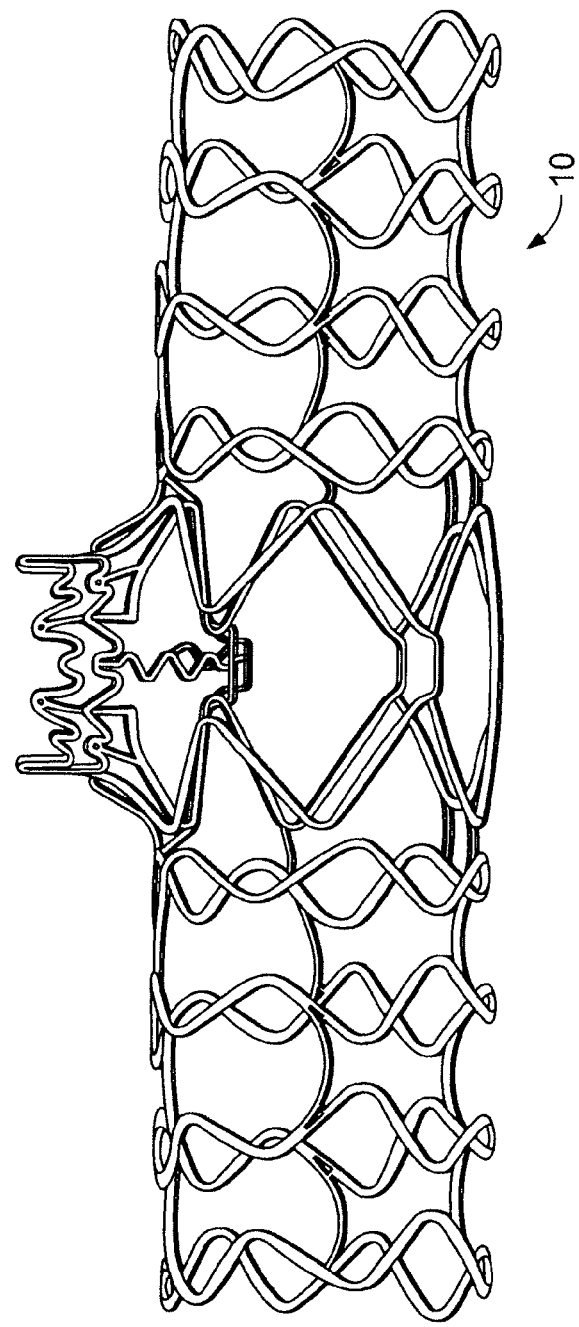

The devices of FIGS. 1K and 1L are designed to cover a region of a lumen having a side-branch.

As can be seen from all of the devices of FIGS. 1A-1H and 1J-1L, the structures are formed from a number of members, sometimes fused to one another. The various members, often called struts, are made from thin portions of material. The dimensions of a given strut are typically in the range 0.1-2.0 mm in width and thickness, and 1.0-5.0 mm in length.

Figure 2A:
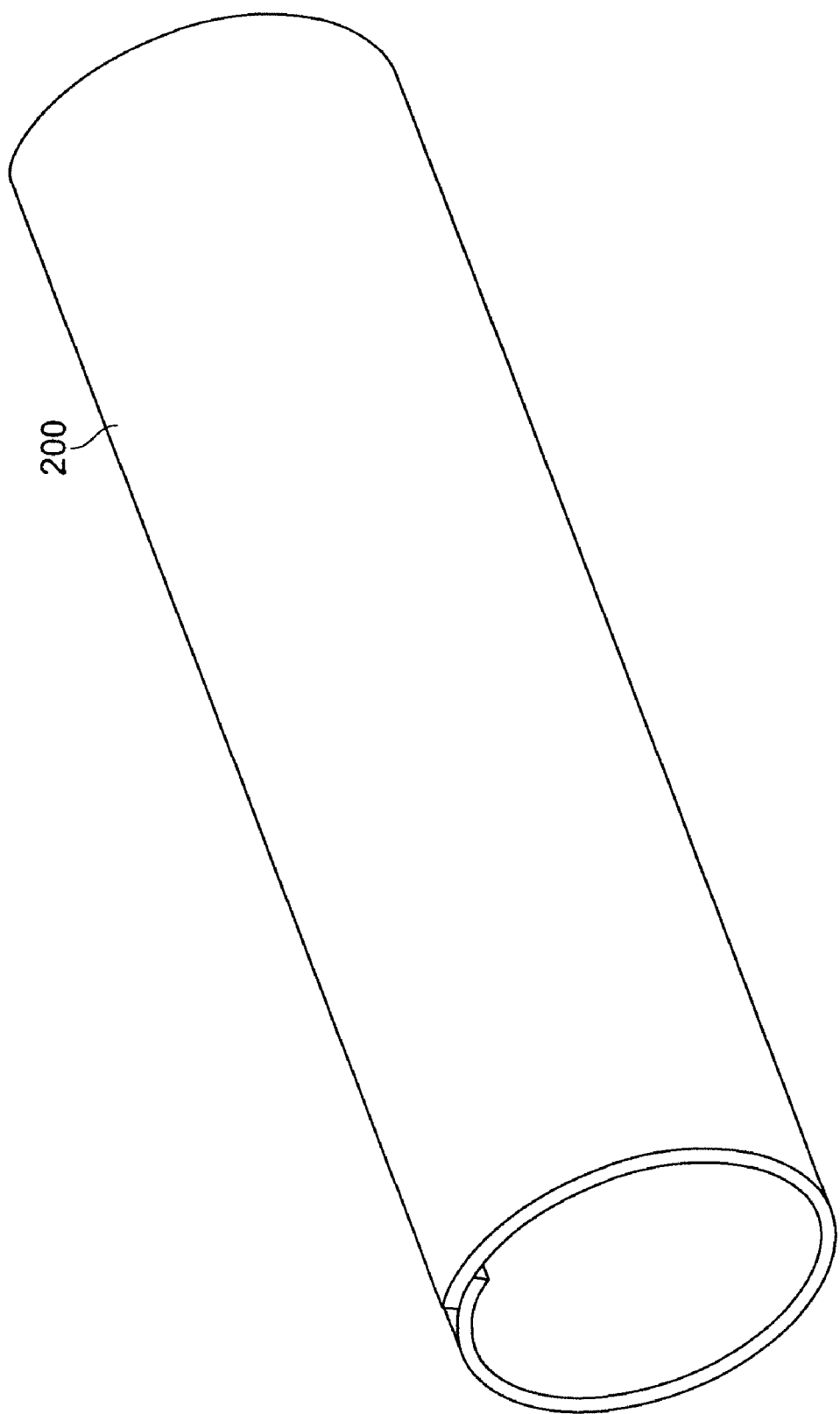
FIGS. 2A-2D are respectively, perspective views of other exemplary endoprostheses.
Figure 2B:
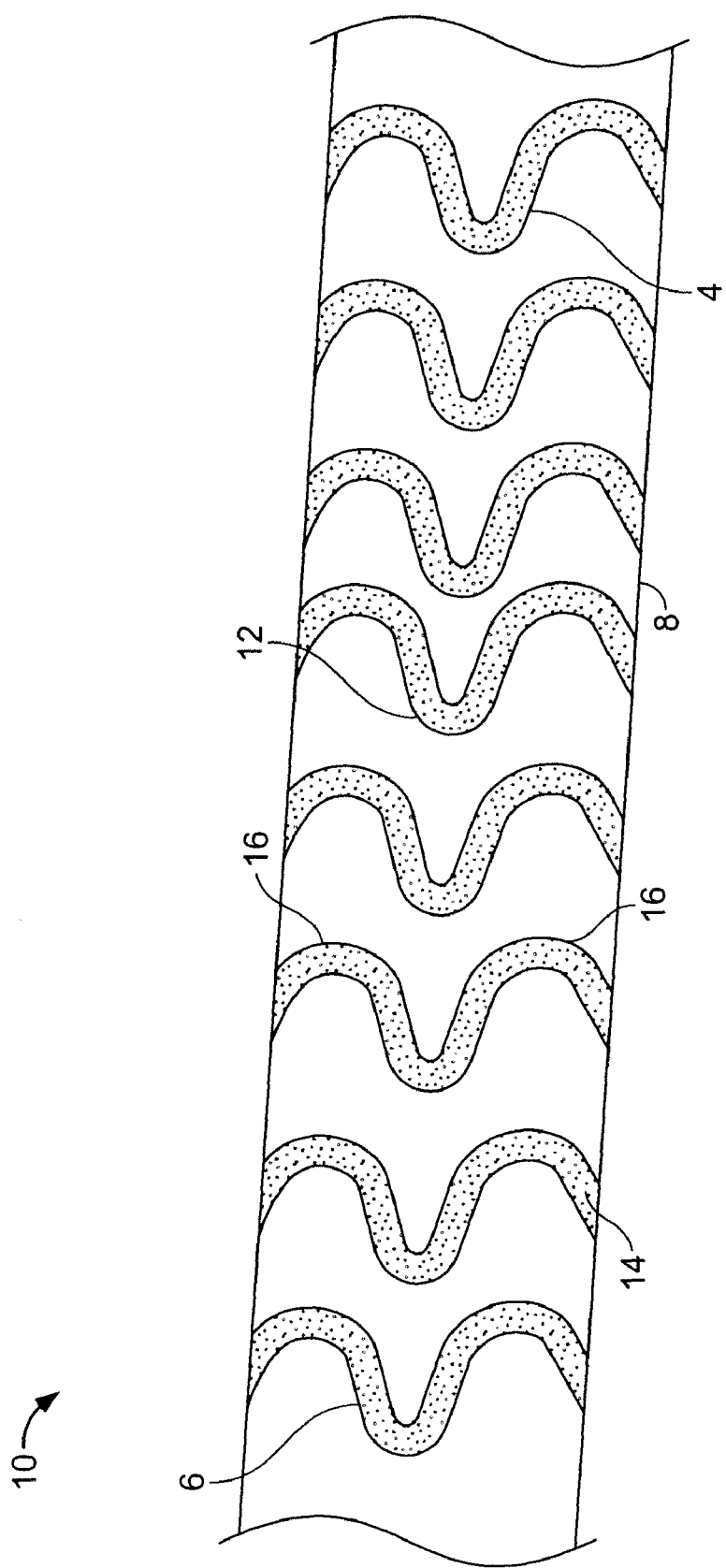
Figure 2C:
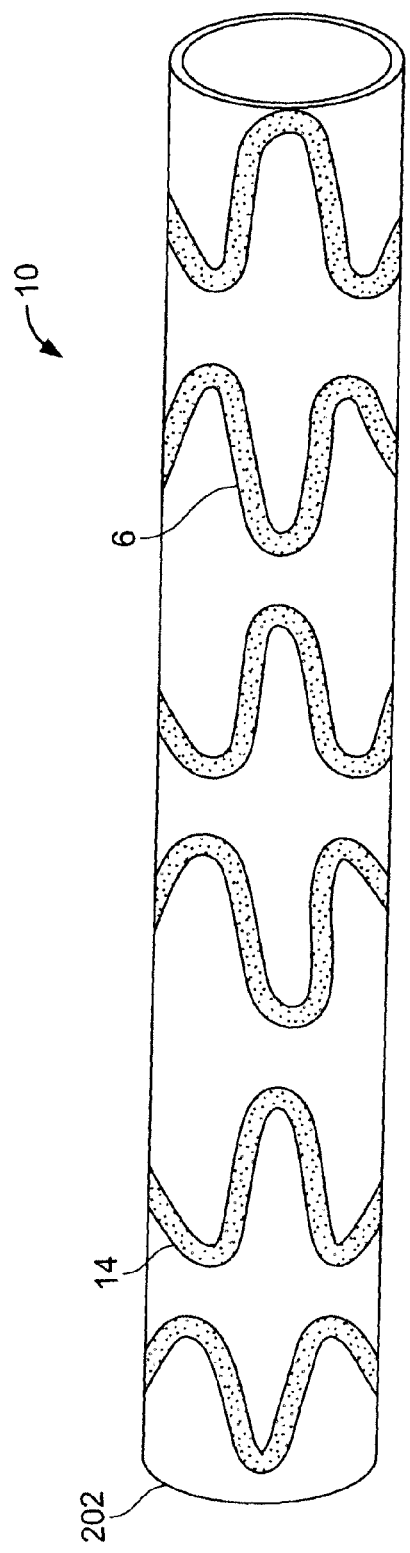
Figure 2D:
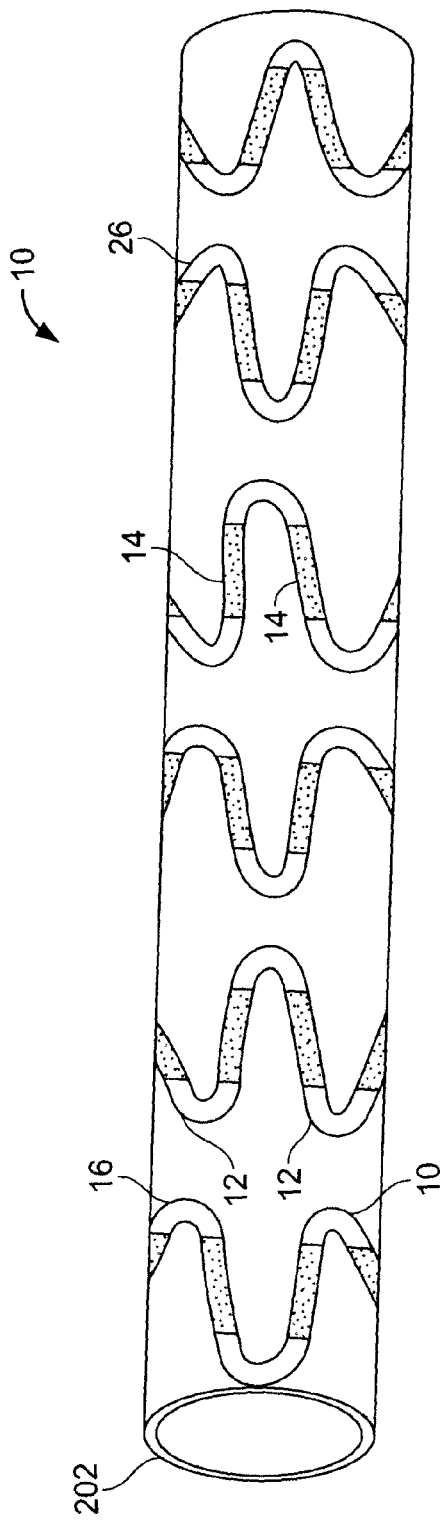

Still other exemplary endoprostheses are tubular grafts, as depicted in FIGS. 2A-2D. Such endoprostheses are made from cylindrical sheets, either extruded as a single tubular sheet 202, as in FIGS. 2B-2D, or extruded as a single sheet 200, open at its edges but configured such that it can expand or contract in radius to fit within a given lumen, as in FIG. 2A. Each of the devices in FIGS. 2A-2D can have one or more materials of a different composition attached to its surface, as shown in FIGS. 2B-2D. It is assumed that, as used in this regard, the term "attached" can mean "affixed", "grafted on", "deposited on", "engraved on", "embedded in", and other similar terms.

There are two principal aspects to controlling the disintegration rate of bio-disintegrable endoprostheses. First, as would be appreciated by one of ordinary skill in the art, a temporary delay of the onset of biodisintegration is helpful in maintaining the mechanical integrity of the device while it is being covered with endothelial cells. Second, there are situations in which it is desirable to be able to fully control the corrosion over the entire lifespan of the device, even if 80% of the material has already been removed. This latter scenario particularly applies where parts of a device will never be fully covered with endothelial cells (for example with a strut passing over a side-branch). In such circumstances, it is important that the exposed strut does not break until the very core of the support structure has degraded. A very slow final corrosion of the center of the strut would therefore be helpful in such a configuration.

The disintegration rate of a medical device can be delayed by various surface treatments or surface coatings as is known in the art. However, such approaches do not permit control over disintegration of the support structure once the surface coatings have dissipated.

The overall disintegration rate of the bulk support structure can be controlled by tailoring the material, e.g., an alloy, from which it is made. However, where the structure is made from a homogeneous composition, this leads only to a single degree of freedom in controlling rate of disintegration.

No method has yet been proposed which allows the disintegration rate to be designed truly in all three dimensions of a support structure. For example, where the disintegration rate is an increasing function towards the core so that a much slower rate is followed at the final inner core, the device is thereby permitted to become a thin durable skeleton that does not disintegrate too early in the life of the device.

Control of device disintegration rate in three dimensions is achieved by making the device from one or more of several processes, as further described herein. The first process is referred to as direct metal laser sintering (DMLS); a specific example is known as laser-engineered net shaping (LENS). These processes permit control of the composition and properties of the structure at various places therein, as it is being manufactured, for example by changing the composition of the metal as it is being build up. Thus, different layers or materials at different positions along the device have different powder compositions. A second process, excimer laser nitriding, permits introduction of variable quantities of nitrogen atoms into a layer of material as it is being deposited. Nitrogen mixed with certain metals can profoundly influence their electrical and mechanical properties according to its proportion. Furthermore, instead of, or in addition to, laser nitriding, an unfinished device can be treated by, for example dipping it into hydrofluoric acid, thereby converting magnesium into magnesium fluoride. The latter is much more resistant to corrosion than is magnesium. Combinations of the foregoing methods may be used. For example, as a LENS process is used to build up a device, layer after layer, any surface treating process described herein—or known to one of ordinary skill in the art—can be applied in between layers to the partly finished device.

DMLS

Direct metal laser sintering (DMLS), and Laser Engineered Net Shaping (LENS), make near-net-shaped (i.e., having a desired end-product shape) metal parts directly from three-dimensional computer-aided design (3D CAD) models. See, e.g., J. Hänninen, "Direct Metal Laser Sintering", *Advanced Materials & Processes,* 160:33-36, (2002), incorporated herein by reference. A strength of these technologies lies in the ability to fabricate fully-dense metal parts with good metallurgical properties at reasonable speeds. "Fully dense" means that the density of the metal part being made is as good as that of a structure being made, starting from bulk material, and that no voids or bubbles get incorporated into the produced material. Accordingly, the mechanical properties of the resulting part are virtually identical to conventionally made products. Material composition can be changed dynamically and continuously, leading to objects with properties that might not be possible using classical fabrication methods. DMLS has fewer limitations than selective laser sintering (SLS) in terms of available materials. DMLS has been widely deployed in the fabrication and repair of injection molding tools, and in the fabrication of large titanium and other exotic metal parts for aerospace applications. In short, objects fabricated with DMLS are near net shape, but generally will require finish machining. They are fully-dense with good grain structure, and have properties similar to, or even better than the intrinsic materials.

Figure 3A:
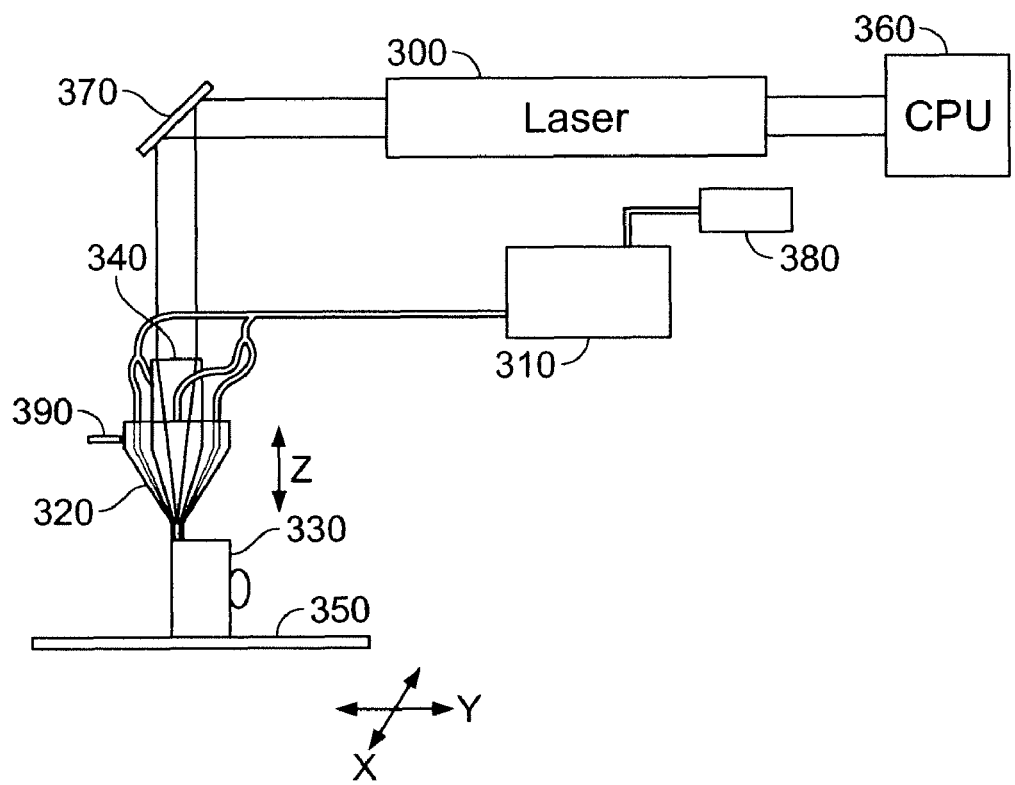
FIG. 3A shows a schematic diagram of a direct metal laser sintering apparatus.

A schematic view of an apparatus for carrying out LENS is shown in FIG. 3A. The apparatus is usually contained within a chamber, both to isolate the process from the ambient surroundings and to shield the operators from possible exposure to fine powders and the laser beam.

During operation of a LENS apparatus, a high power laser 300 is used to melt powder material 310 supplied coaxially to the focus of the laser beam through a deposition head 320. The laser power used varies greatly, from a few hundred watts to 20 kW or more, depending on the particular material, feed-rate and other parameters. The laser beam typically travels through the center of the head and is focused to a small spot on a substrate 330 by one or more lenses 340. Substrate 330 rests upon a X-Y table 350, which is moved, for example in raster fashion, to fabricate each layer of the object. Motions of table 350 are controlled by CPU 360, typically under instructions from a CAD program. Normally the head is moved up vertically, in the z-direction as depicted in FIG. 3A, as each layer is completed. A rotating axis can also be easily implemented, thereby allowing structures having tubular shapes to be processed. Layer thickness varies with the material being deposited, but the thickness is typically in the range 20-50 μm. In alternate embodiments, the head is stationary and the object on the table is moved in a vertical direction. By depositing a metal in a layer-by-layer process, LENS produces fully dense parts with material properties that are comparable to, or better than, those of wrought materials.

The laser beam may be delivered to the substrate by any convenient means. A simple right angle mirror 370 is shown in FIG. 3A, but fiber optics can also be used. Metal powders 310 are delivered and distributed around the circumference of the head either by gravity, or by using pressurized carrier gas 380. Typically carrier gas 380 is an inert gas such as helium, neon, krypton, argon, xenon, or a gas that does not react under the DMLS conditions, such as nitrogen, or carbon dioxide. Even in cases where a gas is not required for feeding, an inert shroud gas 390 is typically used to shield the melt pool from atmospheric oxygen for better control of properties, and to promote layer to layer adhesion by providing better surface wetting.

Most systems use powder feedstocks, but material provided as fine wires has also been used, in which case the material is fed off-axis to the beam.

Figure 3B:
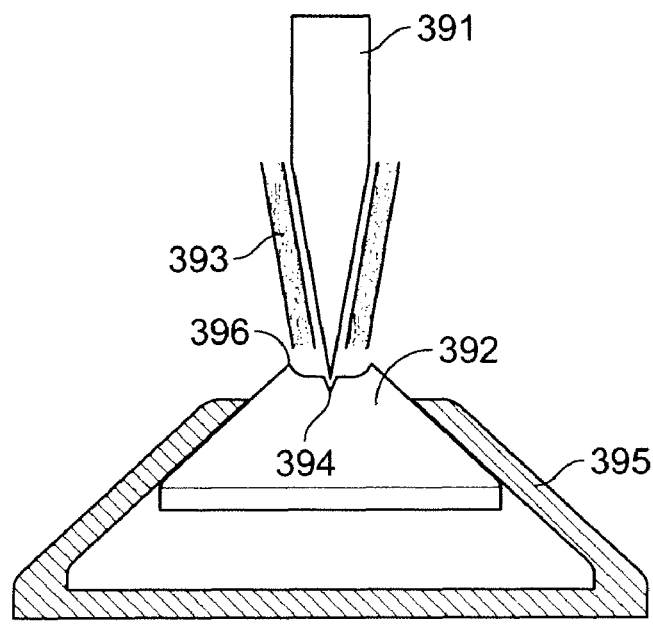
FIG. 3B shows the LENS apparatus.

In another variation of the method, as depicted in FIG. 3B, a high-powered, focused, Nd:YAG laser beam 391 first strikes a tiny spot on a deposition surface 394 on a metal substrate 392, thereby producing a molten pool. Other lasers, known in the art, are also capable of carrying out the method. A nearby powder delivery system 393 having a nozzle blows a precise amount of metal powder into the pool 396 to increase the material volume. The working head moves back-and-forth, line by line, overlapping each layer of metal on the substrate, under control of a computer processor. Repeating this process, layer by layer, produces a metal version of the CAD model. The substrate can be mounted on a stage 395 that undergoes X-Y motion.

An overview of DMSL is provided in: "Direct Metal Laser Sintering for Rapid Tooling: Processing and Characterization of EOS Parts", M. W. Khiang, et al., J. Materials Proc. Technol., 113, 269-272, (2001), incorporated herein by reference. Other variants of DMLS, suitable for use with the methods and devices described herein are found in: "Formation Method for New Corrosion-Resistance [sic] Magnesium Thin Film by CVD Method", M. H. Lee, et al, *Surface and Coatings Technology,* 169-170, 670-674, (2003), and "Thermal and Mechanical Finite Element Modeling of Laser Forming from Metal and Ceramic Powders", K. Dai and L. Shaw, *Acta Materialia,* 52, 69-80, (2004), both of which are incorporated herein by reference. Various methods of carrying out DMLS are described and compared in F. Erzincanh and M. Ermurat, "Comparison of the Direct Metal Laser Fabrication Technologies", 2nd International conference on Responsive Manufacturing, University of Gaziantep, Turkey, (2002), also incorporated herein by reference.

DMLS differs from LENS as depicted in FIG. 3A principally in that the powder is deposited as a layer over the substrate by a coating element, instead of through a concentric feed around the laser beam. In DMLS, then, the laser beam is directed through successive x-y motions across the substrate and, wherever it contacts the powder, melts the powder, fusing it to the layers below. Excess powder is removed, and successive layers are built up by recoating the immediately previous deposited layer with further layers of powder. By contrast, in LENS, the laser melts the stream of powdered metal as it is deposited.

DMLS and LENS increase a designer's choice of materials. A variety of materials, such as stainless steel, inconel, copper, and aluminum, can be used. Typically the powders are carefully tailored to balance the shrinkage that takes place during sintering by the expansion of the individual powder particles. Of particular interest are reactive or hard-to-machine materials such as titanium. Titanium poses few difficulties for DMLS because DMLS makes structures by depositing metal powders. Even multiple powders can be fused in different combinations to create parts that were once impractical, prohibitively expensive, or both. The process gradually transitions between different materials to reduce stress at the interface. The capabilities let designers specify different materials for different areas of a part, depending on the requirements of each.

Excimer Laser Nitriding

Excimer laser nitriding can be used to form nitrides of various metals, including iron, steel, aluminum, titanium, magnesium, and alloys thereof. For example, magnesium-nitride can be created in the surface of a magnesium target by irradiating the substrate with an excimer laser in a molecular nitrogen environment. The laser pulse melts the magnesium target on contact, and creates nitrogen ions in the plasma just above the substrate. These ions react with the magnesium molten by the laser pulse. Magnesium nitride is an excellent protector against corrosion. Exemplary conditions for excimer laser nitriding are described in Soto, G., et al., "Amorphous magnesium nitride films produced by reactive pulsed laser deposition", *J. Non-Crystalline Solids*, 342:65-69, (2004).

Representative excimer lasers for use in excimer nitriding include, but are not limited to, the XeCl, KrF and ArF excimer lasers. The layer thicknesses that can be constructed in this way are in the range 1-10 μm, and preferably 2-7 μm, and even more preferably 3-5 μm.

Figure 4:
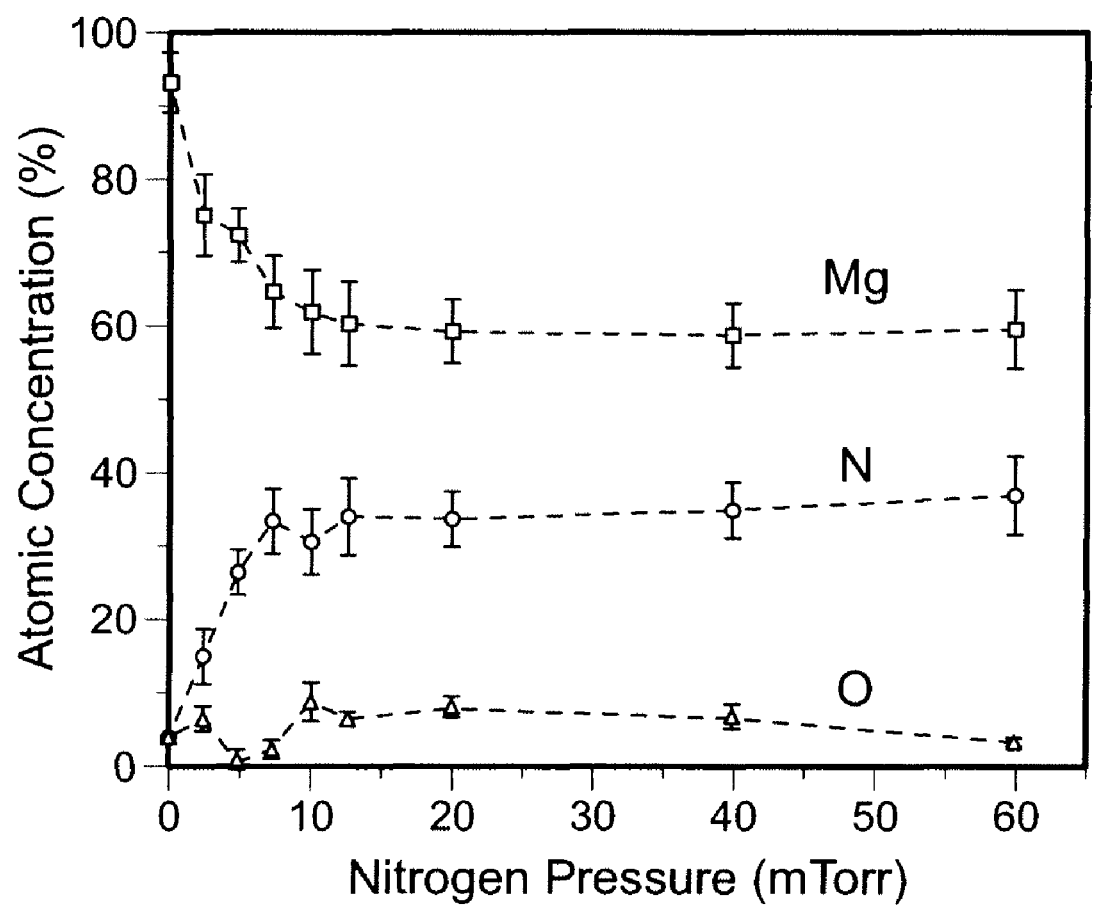
FIG. 4 is a graph of nitrogen content vs. nitrogen partial pressure, as employed in excimer nitriding.

The nitrogen content of magnesium nitride formed by excimer nitriding, given by $x=[N]/[Mg]$ (where square brackets denote atomic concentrations), changes between 0 and 0.73 for a corresponding variation in nitrogen pressure of $4\times10^{-10}$ Torr to 60 mTorr. By this method it is possible to achieve sub-, over- and stoichiometric films at different nitrogen pressures. FIG. 4 shows a graph of nitrogen content (atomic concentration determined by XPS with error bars) vs. nitrogen partial pressure, as employed in excimer nitriding. The graph demonstrates the ability to tailor the nitriding level by adjusting the gas pressure. Ablation was accomplished by means of a KrF excimer laser ($\lambda=248$ nm) focused on the target at 50° off the surface normal. Laser energy, number of pulses and pulse repetition rate were fixed at 400 mJ, 3800 pulses and 2 Hz, respectively, with a laser energy density at target surface of 5 J cm$^{-2}$. The results show that the amorphous matrix keeps its metallic character for $x<0.45$; $x=0.4$ is a critical composition at which the material starts developing ionic characteristics; at $x=0.66$ the solid is totally ionic.

It has been observed that the metallic nature of magnesium disappears when the nitrogen content, $x=[N]/[Mg]$, gets above $x>0.4$. In other words, building a 3D structure utilizing both the layer-by-layer DMSL process with alternating excimer nitriding steps, producing $x>0.4$ throughout the entire strut will create non-metallic struts. So, building in a couple of small sections throughout the circumference of the support structure will result in a stent that allows structure internal to it to be visible in an MRI scan, which is desirable for medical imaging.

The atomic concentration can also be influenced by the number of laser pulses used in the excimer nitriding process, and their duration. As the depth of the nitriding effect depends on the diffusion length during the molten state of the magnesium, pulse length and number does permit this property to be adjusted. Excimer lasers can of course be programmed to deliver exact amount of pulses in controllable energy fluence per pulse. Factors affecting the efficacy of laser nitriding are described in: M. Han, "Laser nitriding of metals", Ph.D. thesis, University of Göttingen, (2001), incorporated herein by reference.

Methods of Manufacture

Medical devices of the present invention can be made by processes that alternate the layer by layer DMSL build up of a metallic structure of, e.g., magnesium or iron, with excimer laser treatment to build in a certain nitride level in the layer deposited immediately previously. Metallic structures may also incorporate other metals. For example, if only part of a stent is supposed to disappear, then noble metals such as titanium, tantalum, or gold can be combined as one or more of the layers in the same device with erodible metals such as magnesium or iron. A totally non-bioerodible device can therefore be made with this technology by integrating heavily nitrided sections within the metal structure. The resulting structure can be, e.g., a MRI-compatible stent. A schematic of the process is shown in FIG. 5. The laser nitriding is optional for each layer. It is also not necessary to treat the whole cross-section of the layer by the nitriding process as the laser beam can be focused onto a much smaller portion (as shown in FIG. 5). Such precision permits tailoring of disintegration rates of different parts of the devices.

Figure 5A:
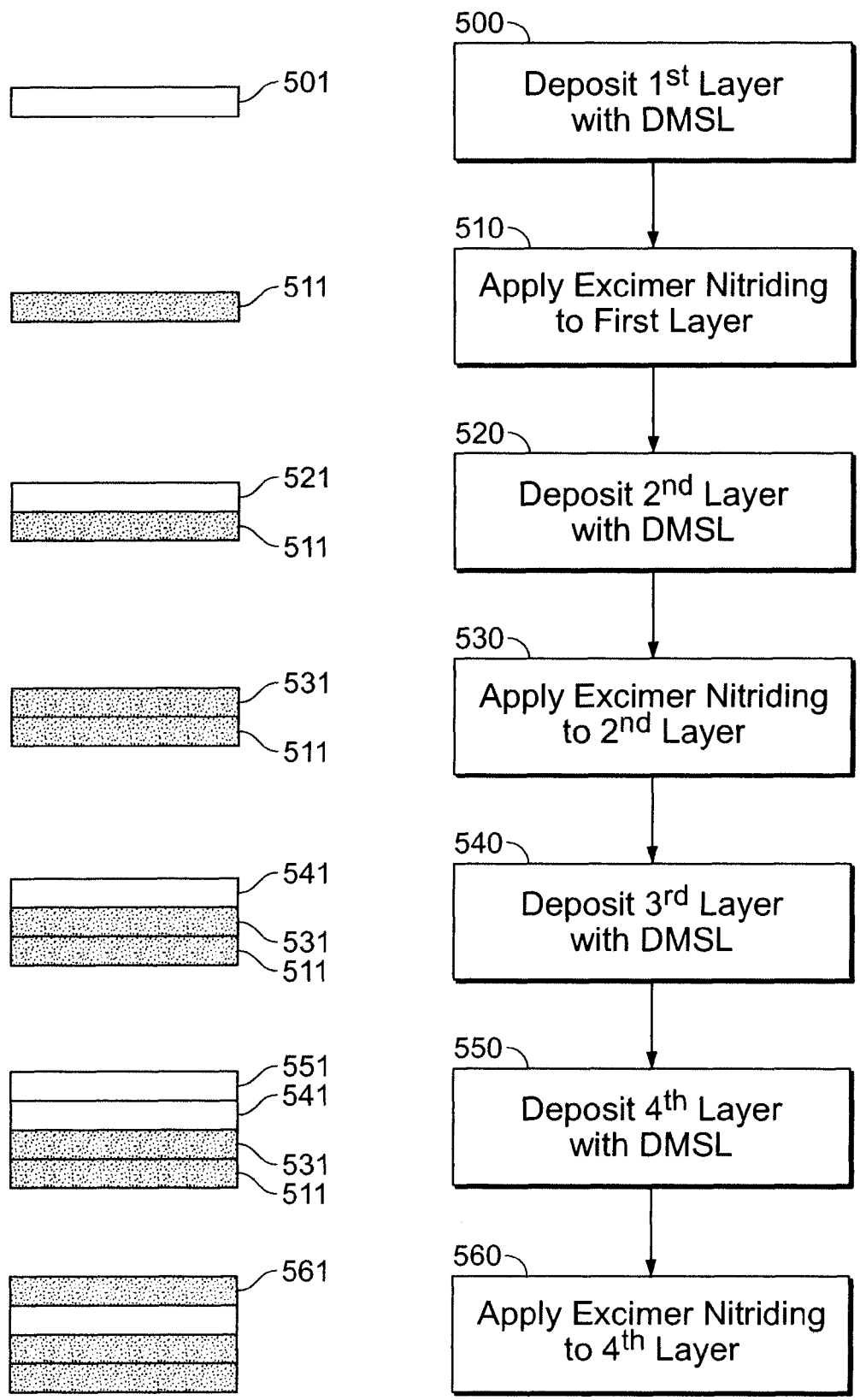
FIGS. 5A and 5B show a sequence of method steps in which layers of material are built up to form a support structure.

FIG. 5A shows a flow-chart of steps associated with build-up of multiple layers of material, and corresponding schematic representation of the layers. At step 500, a first layer 501 is deposited with a DMSL technique such as LENS. Since the shape in which the first layer is deposited will determine the overall shape of the device, it is desirable to control the shape of the first layer. Several ways of defining a shape for the first layer are available. By starting with a flat substrate, a first structure, such as a thin tube in the shape of a stent, can be built perpendicular to the surface. Subsequently, if the structure is a thin tube, it can be rotated by 90 degrees so that its axis lies parallel to the substrate, and the further layers can be deposited as further described hereinbelow while rotating the tube about its axis. Although this manner of defining a first layer creates a solid tube without any pattern as is normally found in, e.g., a stent, after cutting the tube from the substrate a stent pattern can easily be laser cut into the tube, according to methods known to one of ordinary skill in the art. In an alternative embodiment of defining a shape on which a first layer is deposited, a silica base shape (e.g., a wire) can be used. Silica is an effective choice because it can withstand temperatures of up to around 1000° C. as are encountered during, e.g., DMLS or excimer nitriding and so a molten metal can be deposited directly on the silica base shape. After the device has been completed, the silica can be dissolved in hydrofluoric acid. Although hydrofluoric acid will also react with any magnesium in the structure, this reaction only forms a MgF$_2$ layer on the outer surface of the magnesium.

Subsequently, step 510 excimer nitriding is applied to first layer 500, to create a first nitride layer 511, having a first nitrogen content. A second layer 521 is deposited on the first nitride layer 511, in step 520, using a DMSL technique. It is preferable, though not necessary, to use the same DMSL technique for the second and subsequent layers as for the first layer. It is also preferable that the material used in the second and subsequent layers is the same as the material used in the first layer, though this does not necessarily have to be the case, particularly where a graduation of properties is desired to be achieved in a manner other than by introducing nitrogen content in various layers. In step 530, excimer nitriding is applied to second layer 521 to create a second nitride layer 531 having a second nitrogen content. It is to be understood that step 530 can be omitted so that the second layer is given no nitride content. The second nitride content need not be the same as the first nitride content in the first nitride layer. In a further step 540, a third layer 541 is deposited with DMSL on top of the second nitride layer. As shown in FIG. 5, the third layer is not given any nitride content by excimer nitriding, though as would be understood by one of ordinary skill in the art, the third layer could receive a third nitride content as desired. In step 550, a fourth layer 551 is deposited on the third layer. In step 560 excimer nitriding is applied to layer 551 to produce a nitride layer 561. The steps 500-560 can be repeated to cause build up of multiple layers, either consecutively having nitride content, or in some sequences, alternating layers having nitride content with layers having no nitride content.

Figure 5B:
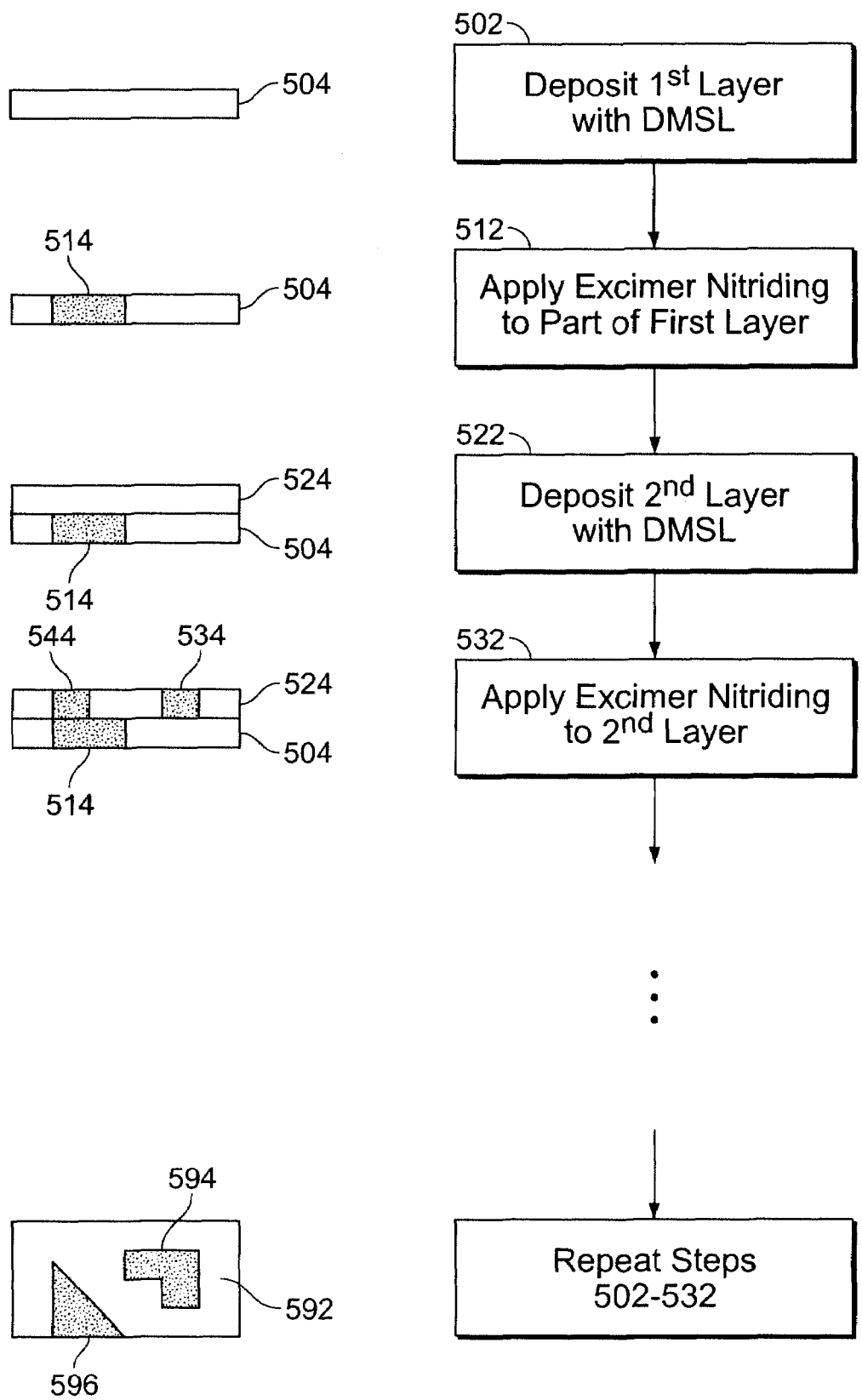

FIG. 5B shows a flow-chart analogous to that shown in FIG. 5A but illustrating how nitrogen content can be selectively introduced into parts of various layers. Step 502, in which a first layer of material 504 is deposited by a DMSL method such as LENS, is analogous to step 500 of FIG. 5B. In step 512, however, excimer nitriding is applied only to a part of first layer 504, thereby creating a region 514 having a desired first nitrogen content. The region may be defined by applying a removable mask, or by other methods familiar to one of ordinary skill in the art of deposition technologies. In step 522, a second layer 524 is deposited over the first layer 504 by a DMSL method. In step 532, excimer nitriding is applied to second layer 524 to create, in the instance shown, two regions 534, 544 having nitrogen content. Steps 502-532 can be repeated to build up a structure of desired shape and cross-section 592, as shown, in which regions 594 and 596 have nitrogen content, that need not be identical to one another. Such a construct can be used to make structures such as stent struts which, if desired, can have different properties from the rest of the device around them.

Layers of the multi-layer structure made in this way may have the same thickness as one another or different thicknesses. In some embodiments, an individual layer and/or an individual layer may have a thickness of at least about 1.0 micron (e.g., at least about 5.0 microns, at least about 10 microns, at least about 50 microns, at least about 100 microns, at least about 300 microns), and/or at most about 500 microns (e.g., at most about 300 microns, at most about 100 microns, at most about 50 microns, at most about 10 microns, or at most about five microns). For example the commercially available EOS 270 M permits a minimum layer thickness of 20 micrometer. Another commercially available piece of equipment, the M 250, can create layers as small as 50 micrometer.

Figure 6:
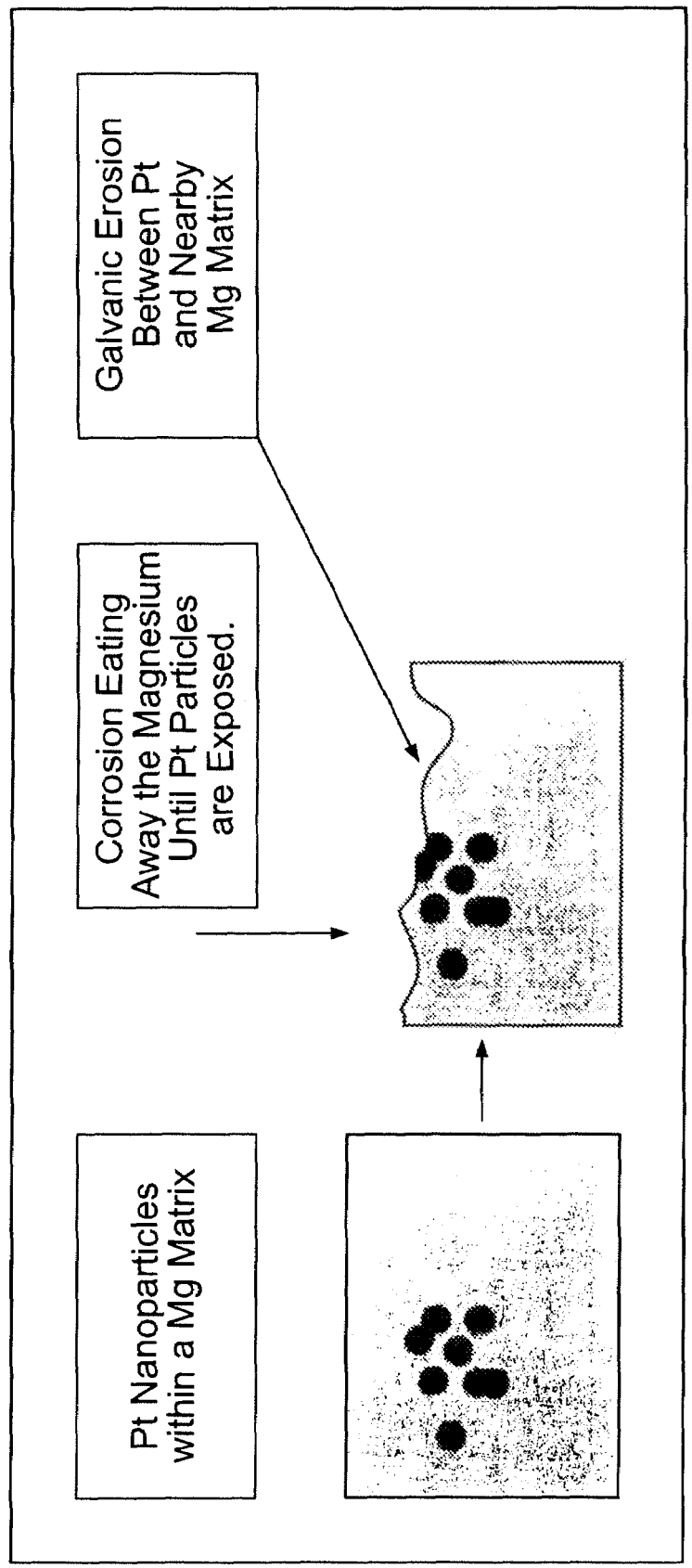
FIG. 6 shows a layer having platinum nanoparticles.

One can build a structure with the DMSL process in which it is possible to change metal composition in any of three orthogonal directions (e.g., as represented by a cartesian x, y and z axis system) just by choosing an appropriate mixture of metal powders at each instant. It is also possible to provide an additional controlled nitriding treatment throughout the complete bulk by using excimer nitriding. Different powders can be applied simultaneously and it is important to note that not all of the powders have to melt to create a structure. It is possible to, for example, blend in platinum (or iron) nano-particles with a very high melting point in a magnesium matrix by feeding both materials at the same time into the laser focus, as shown in FIG. 6. The magnesium will melt, thereby fusing with the bulk and incorporating the platinum nano-particles during the solidification. Incorporation of, e.g., platinum, nanoparticles will locally allow acceleration of the disintegration rate by means of a galvanic cell which is created once the platinum particle is exposed to a saline environment.

This thereby demonstrates that it is possible to both accelerate as well as delay the disintegration rate of the support structure by varying the application of the DMSL and the excimer laser process.

Furthermore, it is possible to start with a structure such as a semi-stent, i.e., an unfinished stent such as one that has not been finished with electro-polishing, made by a different technology (such as cutting a pattern in a tube by laser) and to add to this structure material by means of the DMSL process. It is also possible to apply the LENS processes described herein to a finished stent, thereby permitting build up of additional layers. Such approaches might be advantageous to speed up the overall production process because it thereby avoids using a sacrificial, dissolvable, mandrel. An option is to start with a very thin stainless steel skeleton, plate a first magnesium layer on top of this, e.g., by magnetron sputtering (see, e.g., M. H. Lee, et al., *Surface and Coatings Technology*, 169-170, 670-674, (2003)) and build up further layers by means of DMSL. This also permits intermediate layers between the LENS made layers to be created, and sputtering permits deposition of layers whose thicknesses are in the submicron range.

This approach described herein also makes it possible to join different structures together by building an axial connector that erodes after placement in vivo. For example, a stent for placement in a limb such as a leg, where very high repetitive binding of the arteries occurs, consists of a series of nitinol rings connected by magnesium axial connectors, in order to make sure that disintegration starts in the middle of the connectors and works towards the nitinol rings, it is sufficient to refine the excimer nitriding process to deliver a low number of pulses in the middle, gradually increasing to a high number of pulses near the nitinol rings. In this embodiment, the magnesium connectors support the stent during the first few weeks of placement to keep the vessel open, but once the stent is endothelized, less support is needed and the rings are sufficient, allowing the artery to bend much better.

Many embodiments of a medical device having different numbers of layers in one portion from another portion are possible. By "portion" is meant some non-vanishing part that is less than the whole. Thus, in some embodiments, one portion of a medical device comprises a multi-layered structure with at least 5 layers (e.g., at least 10 layers, at least 20 layers, at least 30 layers, or at least 40 layers), and another portion of a medical device includes a multi-layered structure with at least 20 layers (e.g., at least 30 layers, at least 40 layers, or at least 50 layers). For example, one portion of a medical device may include a multi-layered structure with 10 layers and another portion of the medical device may include a multi-layered structure with 40 layers. In certain embodiments, a multi-layered structure in one portion of a medical device can include from five to 50 layers (e.g., from 10 to 30 layers) more than a multi-layered structure in another portion of the medical device.

In some embodiments, the biodisintegrable material in a portion of the underlying structure that is made up from a relatively large number of layers may begin to disintegrate after, and/or more slowly than, the biodisintegrable material in a portion that includes a relatively small number of layers. Thus, the numbers of layers of a support structure may be used to provide different disintegration rates of biodisintegrable material in different regions of the medical device. In some embodiments, an endoprosthesis can include an arrangement of layers that causes one or both of the ends of the endoprosthesis to start disintegrating before the middle of the endoprosthesis. This may limit the likelihood of the medical device breaking apart into two or more pieces during disintegration.

In some embodiments, one or more portions of a medical device are not constructed, layer-by-layer at all.

Delivery of Therapeutic Agents

In some embodiments, the device is further configured to deliver one or more therapeutic agents. As an example, one or more therapeutic agents can be disposed on or within the multi-layered structure that coats the device, thereby giving the medical device a drug releasing function upon implantation. Therapeutic agents may be used singly or in combination. It is also possible, for example, to make a porous outer layer of a stent from magnesium and then to dip the stent into a solution containing the therapeutic agent in order to load the drug into the pores. An example of such a pore structure is given in M. H. Lee, et al., *Surface and Coatings Technology*, 169-170, 670-674, (2003), at FIG. 1.

Examples of therapeutic agents can be found at cols. 4-6 of U.S. Pat. No. 6,899,731 to Li et al., and at cols. 5-8 of U.S. Pat. No. 6,923,996 to Epstein et al., the disclosures of which are incorporated by reference in their entirety. It is to be understood that the therapeutic agents that can be used are not limited to those found herein.

Examples of therapeutic agents and methods of incorporating such agents into a multi-layer structure are described in U.S. patent application Ser. No. 10/849,742, filed May 20, 2004. U.S. Pat. No. 5,733,925, to Kunz et al., also provides general guidance for incorporating therapeutic agents into layers.

The multi-layer structure may instead or additionally be used to deliver an antimicrobial agent, such as for the purpose of preventing or limiting local infection in the vicinity of the device. Exemplary antimicrobial agents have broad-spectrum activity and include triclosan, chlorhexidine, silver sulfadiazine, silver ions, benzalkonium chloride, and zinc pyrithione, as well as broad-spectrum antibiotics such as quinolones, fluoroquinolones, aminoglycosides and sulfonamides. Antiseptics such as iodine, methenamine, nitrofurantoin, validixic acid and other acidifying agents, including acids extracted from cranberry juice may also be used.

The therapeutic agent can be charged, either because it is itself a charged molecule or because it becomes charged upon, for example, a change in ambient pH or upon association with a charged species. Examples of charged therapeutic agents include small molecule and polymeric therapeutic agents containing ionically dissociable groups. In some embodiments in which the therapeutic agent does not possess one or more charged groups, it can nevertheless be provided with a charge, for example, through non-covalent association with a charged species. Examples of non-covalent associations include hydrogen bonding, electrostatic, van der Waals, and hydrophobic/lipophilic interactions. For instance, a therapeutic agent can be associated with an ionic amphiphilic substance.

A wide range of therapeutic agent loadings can be used. The amount of such loading can be readily determined by those of ordinary skill in the art, and will ultimately depend upon the condition to be treated, the nature of the therapeutic agent itself, the avenue by which the therapeutic-agent-loaded layer-by-layer structure is administered to the intended subject, and so forth. The loaded multi-layered structure, may comprise, for example, from about 1 wt. % to about 70 wt. % therapeutic agent.

The amount of the therapeutic agent may be limited by the propensity of such agent to cause an undesirable localized or systemic toxic reaction and by the impairment of mechanical properties necessary for proper functioning of the device.

In still other embodiments, the therapeutic agent can be provided within charged nanocapsules, which are formed, for example, using methods such as those described in U.S. Patent Application Publication No. 2005-0129727, entitled "Localized Drug Delivery Using Drug-Loaded Nanocapsules". In such embodiments, one or more layers of charged nanocapsules can be deposited during the course of assembling the multi-layer coating.

In still other embodiments, the multi-layer structure is loaded with a therapeutic agent subsequent to its formation. For example, the porosity, and thus the penneability, of the multi-layer structure can be modified by adjusting the pH exposed to the structure, as described, for example, in Antipov, A. A., et al., "Polyelectrolyte multilayer capsule permeability control," *Colloids and Surfaces A: Physicochemical and Engineering Aspects*, 198-200, 535-541, (2002). A porous layer can absorb a therapeutic agent after the layer is in place.

Device Materials

The support structure of the medical device of the present invention is, in some embodiments, formed of a biocompatible material, such as the materials described herein. Specific examples of biocompatible materials from which the underlying structure can be formed are described in U.S. patent application Ser. No. 10/440,063, filed May 15, 2003; and U.S. Patent Application Publication Nos. 2003-0018380, 2002-0144757, and 2003-0077200. Still further examples of biocompatible materials are described, for example, in Weber et al., U.S. Patent Application Publication No. 2004/0230290 A1, published on Nov. 18, 2004; Craig et al., U.S. Patent Application Publication No. 2003/0018380 A1, published on Jan. 23, 2003; Craig et al., U.S. Patent Application Publication No. US 2002/0144757 A1, published on Oct. 10, 2002; and Craig et al., U.S. Patent Application Publication No. 2003/0077200 A1, published on Apr. 24, 2003. Preferred materials suitable for DMLS/laser nitriding are materials that can be molten. Into a molten pool of material can be sprayed both metallic or ceramic powders or even a combination thereof. It is also possible to spray a mixture of magnesium and magnesium-nitride powders to achieve a similar effect to the laser nitriding process.

The biocompatible material can be suitable for use in, for example, a balloon-expandable stent, a self-expandable stent, or a combination of both (see e.g., U.S. Pat. No. 5,366,504). A self-expandable stent can be formed of a continuous solid mass of a relatively elastic biocompatible material, such as a superelastic or pseudo-elastic metal alloy, for example, a Nitinol (e.g., 55% nickel, 45% titanium). A self-expanding stent has a mechanical memory such that it can return to a preformed shape after it has been compressed or deformed. The stent is initially configured in its final desired shape and is then contracted by deforming or constraining it using any of several methods known in the art. It remains in a contracted state until it is delivered to the target site where it is allowed to expand to its initial state. Examples of materials that can be used for a balloon-expandable stent include noble metals, radiopaque materials, stainless steel, and alloys comprising stainless steel and one or more radiopaque materials.

The support structure can be formed of a biodisintegrable material, such as a biodisintegrable metal, or a biodisintegrable metal alloy. Biodisintegrable materials are described, for example, in U.S. Pat. No. 6,287,332 to Bolz; U.S. Patent Application Publication No. US 2002/0004060 A1 to Heublein; U.S. Pat. Nos. 5,587,507 and 6,475,477 to Kohn et al. Examples of biodisintegrable metals for use with the support structure include alkali metals, alkaline earth metals (e.g., magnesium), iron, zinc, and aluminum. Examples of biodisintegrable metal alloys include alkali metal alloys, alkaline earth metal alloys (e.g., magnesium alloys), iron alloys (e.g., alloys including iron and up to seven percent carbon), zinc alloys, and aluminum alloys.

In some embodiments, a biodisintegrable material from which the underlying structure is formed, can include at least one metallic component and at least one non-metallic component, or at least two different metallic components. In some embodiments, a biodisintegrable material can include at least one of the following: manganese, cobalt, nickel, chromium, copper, cadmium, lead, tin, thorium, zirconium, silver, gold, palladium, platinum, rhenium, silicon, calcium, lithium, aluminum, zinc, iron, carbon, and sulfur. In certain embodiments, a biodisintegrable material can include at least two of the following metals in proportions by weight of greater than about 1%: magnesium, titanium, zirconium, niobium, tantalum, zinc, or silicon, and lithium, sodium, potassium, calcium, iron, or manganese. In certain embodiments, the biodisintegrable material can include a first component selected from the group consisting of: magnesium, titanium, zirconium, niobium, tantalum, zinc, silicon, and another, different, component selected from the group consisting of: lithium, sodium, potassium, calcium, iron, manganese.

The properties of the support structure depend upon the material from which it is formed. Magnesium, for example, has a relatively low mass attenuation factor, and the CT visibility of the region (e.g., a body lumen) in which a magnesium structure is located can be relatively high.

Metallic materials from which the underlying structure is made may be made into filaments and then woven so that the underlying structure forms a regular network of metal mesh. If the network is made of metal, the intersection between different filaments may formed by welding, twisting, bending, gluing, tying (with suture), heat sealing, or by any other manner known in the art.

As another example, the support structure of a medical device can include one or more biostable materials in addition to including one or more biodisintegrable materials. One or more polymers may be used (as described herein) to control the disintegration of one or more of the biodisintegrable regions of the stent. The polymers may be in the form of layers over the biodisintegrable and/or biostable regions of the stent or a fiber meshwork similarly disposed. Examples of biostable materials include stainless steel, tantalum, nickel-chrome, cobalt-chromium alloys such as Elgiloy® and Phynox®, Nitinol (e.g., 55% nickel, 45% titanium), and other alloys based on titanium, including nickel titanium alloys, thermo-memory alloy materials. Stents including biostable and biodisintegrable regions are described, for example, in U.S. patent application Ser. No. 11/004,009, filed on Dec. 3, 2004, and entitled "Medical Devices and Methods of Making the Same".

Stents/Devices

The embodiments described herein may be used in conjunction with various medical devices, in particular endoprostheses. Exemplary medical devices are implantable or insertable medical devices, including catheters (for example, urinary catheters or vascular catheters such as balloon catheters), guide wires, balloons, filters (e.g., vena cava filters), stents of any desired shape and size (including coronary vascular stents, aortic stents, cerebral stents, urology stents such as urethral stents and ureteral stents, biliary stents, tracheal stents, gastrointestinal stents, peripheral vascular stents, neurology stents and esophageal stents), grafts such as stent grafts and vascular grafts, cerebral aneurysm filler coils (including GDC—Guglilmi detachable coils—and metal coils), filters, myocardial plugs, patches, pacemakers and pacemaker leads, heart valves, and biopsy devices. Indeed, embodiments herein can be suitably used with any metallic support structure which is designed for use in a patient, either for procedural use or as an implant.

The medical devices may further include drug delivery medical devices for systemic treatment, or for treatment of any mammalian tissue or organ. Subjects can be mammalian subjects, such as human subjects. Non-limiting examples of tissues and organs for treatment include the heart, coronary or peripheral vascular system, lungs, trachea, esophagus, brain, liver, kidney, bladder, urethra and ureters, eye, intestines, stomach, colon, pancreas, ovary, prostate, gastrointestinal tract, biliary tract, urinary tract, skeletal muscle, smooth muscle, breast, cartilage, and bone.

In some embodiments, the medical device is used to temporarily treat a subject without permanently remaining in the body of the subject. For example, in some embodiments, the medical device can be used for a certain period of time (e.g., to support a lumen of a subject), and then can disintegrate after that period of time.

Depending on specific application, stents can have a diameter of between, for example, 1 mm and 46 mm. In certain embodiments, a coronary stent can have an expanded diameter of from about 2 mm to about 6 mm. In some embodiments, a peripheral stent can have an expanded diameter of from about 4 mm to about 24 mm. In certain embodiments, a gastrointestinal and/or urology stent can have an expanded diameter of from about 6 mm to about 30 mm. In some embodiments, a neurology stent can have an expanded diameter of from about 1 mm to about 12 mm. An abdominal aortic aneurysm (AAA) stent and a thoracic aortic aneurysm (TAA) stent can have a diameter from about 20 mm to about 46 mm.

Stents can also be a part of a stent-graft or a covered stent. In other embodiments, stents can include and/or be attached to a biocompatible, non-porous or semi-porous polymer matrix made of polytetrafluoroethylene (PTFE), expanded PTFE, polyethylene, urethane, or polypropylene.

EXAMPLES

Example 1

Magnesium Rod With Layer Structure

In this example, laser sintering is performed on the EOSINT M 270 (available from EOS GmbH Electro Optical Systems, Munich, Germany) is used. The Nitrogen purge is replaced by Argon in order to prevent a reaction of the molten magnesium with the nitrogen.

Starting with a flat magnesium rod (99.9% purity, Sigma Aldrich, Cat. #299405), a vertical solid rod is made (length 15 mm, diameter 2 mm) by injecting magnesium powder (magnesium, ReagentPlus™, ≧99% purity, powder, particle size −50 mesh, Sigma Aldrich Cat. #253987). The finished rod is cut from the original rod.

In a second step, the outer surface of the as-made magnesium rod is nitrided by exposing the surface to a 248 nm laser operating at 30 ns pulses (lamba Physic SX 200K), and by focusing the beam to a rectangular area of 1 mm by 16 mm long along the central axis of the rod. This results in an energy fluence of 4 J/cm$^2$. Ten pulses are given at each position after which the tube is rotated 60 degrees. Nitrogen gas is flushed over the tube during the laser treating. The process is carried out at room temperature and at atmospheric pressure.

In a third step, an additional layer of magnesium is added to the outer surface of the magnesium rod by mounting the rod sideways in the EOSINT M 270, which allows deposit of a 20 micrometer thick layer of magnesium by spiraling the rod underneath the laser beam/powder feeder.

This cycle of nitriding and adding a 20 micrometer thick layer is repeated 6 times. The as made rod consists of a core of magnesium and 7 layers of pure magnesium and intermediate layers of $Mg_2N_3$ alloy. This rod is removed from the laser processing station and a central hole (diameter 2 mm) is drilled along the central axis of the rod. A stent pattern is made out of this tube by cutting a pattern using a femtosecond laser.

All non-patent literature publications, patent applications, patent application publications, and patents, referred to in the instant application are incorporated herein by reference in their entirety.

Other embodiments are to be found within the appended claims.

What is claimed is:

1. A method of making a biodisintegrable endoprosthesis, the method comprising:
    forming a first layer of biodisintegrable metal on a support structure by direct metal laser sintering a metal powder, wherein the first layer is biodisintegrable; and
    introducing a first nitrogen content into a first part of the first layer by excimer laser nitriding.

2. The method of claim 1, wherein the endoprosthesis is a stent.

3. The method of claim 1, further comprising:
    constructing a second layer of a second material, upon the first layer, by direct metal laser sintering.

4. The method of claim 3, further comprising:
    introducing a second nitrogen content into a second part of the second layer by excimer laser nitriding.

5. The method of claim 3, further comprising:
    constructing a third layer of a third material, upon the second layer, by direct metal laser sintering.

6. The method of claim 5, further comprising:
    introducing a third nitrogen content into a third part of the third layer by excimer laser nitriding.

7. The method of claim 5, further comprising:
    constructing further alternating layers on the third layer, wherein the alternating layers comprise, in sequence, a direct metal laser sintered layer, and a direct metal laser sintered layer having a nitrogen content introduced by excimer laser nitriding.

8. The method of claim 1 wherein the biodisintegrable metal is a metal selected from the group consisting of: alkali metals, alkaline earth metals, iron, zinc, and aluminum.

9. The method of claim 8 wherein the biodisintegrable metal is magnesium.

10. The method of claim 3 wherein the biodisintegrable metal is iron.

11. The method of claim 1, wherein the biodisintegrable metal is a metal alloy.

12. The method of claim 1 wherein the endoprosthesis has a shape, and wherein the shape is generally tubular.

13. The method of claim 1 wherein the first part of the first layer is the entirety of the first layer.

14. The method of claim 1 wherein the first material comprises platinum nanoparticles within a matrix of the biodisintegrable metal.

15. The method of claim 10 wherein the second material is magnesium.

16. A method of making a support structure for a medical device, the method comprising:
    constructing, on the support structure, a first layer of iron by direct metal laser sintering;
    introducing a first nitrogen content into a first part of the first layer by excimer laser nitriding;
    constructing a second layer of magnesium, upon the first layer, by direct metal laser sintering, wherein, after excimer nitriding, the second layer has a ratio of nitrogen to magnesium of less than 0.45.

17. A method of making a support structure for a medical device, the method comprising:
    constructing, on the support structure, a first layer of iron by direct metal laser sintering;
    introducing a first nitrogen content into a first part of the first layer by excimer laser nitriding;
    constructing a second layer of magnesium, upon the first layer, by direct metal laser sintering, wherein, after excimer nitriding, the second layer has a ratio of nitrogen to magnesium of greater than 0.45.

18. The method of claim 1 wherein the direct metal laser sintering is laser-engineered net shaping.

* * * * *

UNITED STATES PATENT AND TRADEMARK OFFICE
CERTIFICATE OF CORRECTION

PATENT NO. : 8,052,743 B2
APPLICATION NO. : 11/833211
DATED : November 8, 2011
INVENTOR(S) : Jan Weber et al.

Page 1 of 1

It is certified that error appears in the above-identified patent and that said Letters Patent is hereby corrected as shown below:

1.) Cover Page; Section (56) References Cited - Other Publications; Line 1:
delete "Amporphous" and insert --Amorphous--.

2.) Cover Page; Section (56) References Cited - Other Publications; Line 5:
delete "60/8269,002" and insert --60/826,002--.

Signed and Sealed this
Sixth Day of March, 2012

David J. Kappos
*Director of the United States Patent and Trademark Office*